(12) United States Patent
Sinelnikov et al.

(10) Patent No.: US 7,837,676 B2
(45) Date of Patent: Nov. 23, 2010

(54) CARDIAC ABLATION DEVICES

(75) Inventors: Yegor Sinelnikov, Port Jefferson, NY (US); Yong Zou, S. Setauket, NY (US); Reinhard Warnking, Setauket, NY (US); James Savage, Farmingville, NY (US); Robert C. Pacheco, Commack, NY (US); Jaime Merino, Elmont, NY (US); Patrick David Lopath, Durham, NC (US); John Hotmer, Sound Beach, NY (US); Todd Fjield, Laguna Hills, CA (US)

(73) Assignee: Recor Medical, Inc., Ronkonkoma, NY (US)

( * ) Notice: Subject to any disclaimer, the term of this patent is extended or adjusted under 35 U.S.C. 154(b) by 532 days.

(21) Appl. No.: 10/783,310

(22) Filed: Feb. 20, 2004

(65) Prior Publication Data

US 2004/0176757 A1 Sep. 9, 2004

Related U.S. Application Data

(60) Provisional application No. 60/448,804, filed on Feb. 20, 2003.

(51) Int. Cl.
*A61B 18/04* (2006.01)
(52) U.S. Cl. .......................... 606/27; 606/41
(58) Field of Classification Search ............. 606/27–28, 606/41, 45–50; 607/101, 102, 116, 122, 607/27
See application file for complete search history.

(56) References Cited

U.S. PATENT DOCUMENTS 3,168,659 A 2/1965 Bayre et al.
4,084,582 A 4/1978 Nigam (Continued)

FOREIGN PATENT DOCUMENTS

EP 1042990 10/2000

(Continued)

OTHER PUBLICATIONS

Chen, Shih-Ann, M.D., "Initiation of Atrial Fibrillation by Ectopic Beats Originating From the Pulmonary Veins," Circulation 100(18):1879-86, 1999.

(Continued)

*Primary Examiner*—Michael Peffley
(74) *Attorney, Agent, or Firm*—Jones Day; Nicola A. Pisano; Christopher C. Bolten

(57) ABSTRACT

A cardiac ablation device treats atrial fibrillation by directing and focusing ultrasonic waves into a ring-like ablation region (A). The device desirably is steerable and can be moved between a normal disposition, in which the ablation region lies parallel to the wall of the heart for ablating a loop-like lesion, and a canted disposition, in which the ring-like focal region is tilted relative to the wall of the heart, to ablate only a short, substantially linear lesion. The ablation device desirably includes a balloon reflector structure (18, 1310) and an ultrasonic emitter assembly (23, 1326), and can be steered and positioned without reference to engagement between the device and the pulmonary vein or ostium. A contrast medium (C) can be injected through the ablation device to facilitate imaging, so that the device can be positioned based on observation of the images.

13 Claims, 27 Drawing Sheets

U.S. PATENT DOCUMENTS

| | | |
|---|---|---|
| 4,185,501 A | 1/1980 | Proudian et al. |
| 4,194,510 A | 3/1980 | Proudian |
| 4,338,942 A | 7/1982 | Fogarty |
| 4,387,720 A | 6/1983 | Miller |
| 4,391,281 A | 7/1983 | Green |
| 4,403,612 A | 9/1983 | Fogarty |
| 4,433,692 A | 2/1984 | Baba |
| 4,672,961 A | 6/1987 | Davies |
| 4,680,499 A | 7/1987 | Umemura et al. |
| 4,685,334 A | 8/1987 | Latimer |
| 4,691,714 A | 9/1987 | Wong et al. |
| 4,722,347 A | 2/1988 | Abrams et al. |
| 4,800,316 A | 1/1989 | Ju-Zhen |
| 4,841,977 A | 6/1989 | Griffith et al. |
| 4,869,263 A | 9/1989 | Segal et al. |
| 4,914,510 A | 4/1990 | Brennesholtz et al. |
| 4,945,912 A | 8/1990 | Langberg |
| 4,972,826 A | 11/1990 | Koehler et al. |
| 5,104,393 A | 4/1992 | Isner |
| 5,105,116 A | 4/1992 | Okamoto et al. |
| 5,117,831 A | 6/1992 | Jang et al. |
| 5,135,001 A | 8/1992 | Sinofsky et al. |
| 5,140,987 A | 8/1992 | Schuger |
| 5,167,233 A | 12/1992 | Eberle et al. |
| 5,209,299 A | 5/1993 | Ayres |
| 5,217,454 A | 6/1993 | Khoury |
| 5,226,421 A | 7/1993 | Frisbie et al. |
| 5,226,430 A | 7/1993 | Spears |
| 5,240,005 A | 8/1993 | Viebach |
| 5,242,438 A | 9/1993 | Saadatmanesh et al. |
| 5,242,441 A | 9/1993 | Avitall |
| 5,246,438 A | 9/1993 | Langberg |
| 5,281,213 A | 1/1994 | Milder et al. |
| 5,281,218 A | 1/1994 | Imran |
| 5,293,868 A | 3/1994 | Nardella |
| 5,295,484 A | 3/1994 | Marcus et al. |
| 5,305,731 A | 4/1994 | Buchholtz |
| 5,305,755 A | 4/1994 | Nakao |
| 5,338,295 A | 8/1994 | Cornelius et al. |
| 5,364,388 A | 11/1994 | Koziol |
| 5,385,148 A | 1/1995 | Lesh et al. |
| 5,415,654 A | 5/1995 | Daikuzono |
| 5,419,335 A | 5/1995 | Hartmann et al. |
| 5,421,338 A | 6/1995 | Crowley et al. |
| 5,423,319 A | 6/1995 | Seyed-Bolorforosh |
| 5,423,807 A | 6/1995 | Milder |
| 5,454,782 A | 10/1995 | Perkins |
| 5,468,239 A | 11/1995 | Tanner |
| 5,471,988 A | 12/1995 | Fuijo |
| 5,477,736 A | 12/1995 | Lorraine |
| 5,488,955 A | 2/1996 | Dias |
| 5,513,639 A | 5/1996 | Satomi et al. |
| 5,571,088 A * | 11/1996 | Lennox et al. ........... 604/96.01 |
| 5,575,766 A | 11/1996 | Swartz et al. |
| 5,575,787 A | 11/1996 | Abela |
| 5,582,609 A | 12/1996 | Swanson et al. |
| 5,596,989 A | 1/1997 | Morita |
| 5,606,974 A | 3/1997 | Castellano |
| 5,620,479 A | 4/1997 | Diedrich |
| 5,630,837 A | 5/1997 | Crowley |
| 5,643,279 A | 7/1997 | Trotta |
| 5,655,539 A | 8/1997 | Wang et al. |
| 5,669,932 A | 9/1997 | Fischell et al. |
| 5,676,692 A | 10/1997 | Sanghui |
| 5,767,692 A | 10/1997 | Sanghui |
| 5,693,043 A | 12/1997 | Kittrell |
| 5,704,361 A | 1/1998 | Seward et al. |
| 5,720,287 A | 2/1998 | Chapelon et al. |
| 5,762,066 A | 6/1998 | Law et al. |
| 5,776,141 A | 7/1998 | Klein et al. |
| 5,800,392 A | 9/1998 | Racchini |
| 5,817,018 A | 10/1998 | Ohtomo |
| 5,840,031 A | 11/1998 | Crowley |
| 5,848,969 A | 12/1998 | Panescu et al. |
| 5,860,974 A | 1/1999 | Abele |
| 5,868,708 A | 2/1999 | Hart et al. |
| 5,868,779 A | 2/1999 | Ruiz |
| 5,916,170 A | 6/1999 | Kolz et al. |
| 5,916,213 A | 6/1999 | Haissaguerre et al. |
| 5,921,982 A | 7/1999 | Lesh et al. |
| 5,931,811 A | 8/1999 | Haissaguerre |
| 5,938,660 A | 8/1999 | Swartz et al. |
| 5,964,751 A | 10/1999 | Amplatz |
| 5,971,968 A * | 10/1999 | Tu et al. ..................... 604/264 |
| 5,971,983 A | 10/1999 | Lesh |
| 6,002,955 A | 12/1999 | Willems |
| 6,004,269 A | 12/1999 | Crowley et al. |
| 6,011,995 A | 1/2000 | Guglielmi et al. |
| 6,012,457 A | 1/2000 | Lesh |
| 6,013,053 A | 1/2000 | Bower et al. |
| 6,017,274 A | 1/2000 | Sherman et al. |
| 6,022,319 A | 2/2000 | Willard |
| 6,024,740 A | 2/2000 | Lesh et al. |
| 6,055,859 A | 5/2000 | Kozuka et al. |
| 6,064,902 A | 5/2000 | Haissaguerre |
| 6,068,629 A | 5/2000 | Haissaguerre et al. |
| 6,094,988 A | 8/2000 | Aindow |
| 6,096,054 A | 8/2000 | Wyzgala et al. |
| 6,102,908 A | 8/2000 | Tu et al. |
| 6,106,474 A | 8/2000 | Koger et al. |
| 6,117,101 A | 9/2000 | Diederich et al. |
| 6,146,379 A * | 11/2000 | Fleischman et al. ........... 606/41 |
| 6,152,144 A | 11/2000 | Lesh et al. |
| 6,152,920 A | 11/2000 | Thompson |
| 6,161,543 A | 12/2000 | Cox et al. |
| 6,163,716 A | 12/2000 | Edwards |
| 6,164,283 A | 12/2000 | Lesh |
| 6,183,492 B1 | 2/2001 | Hart et al. |
| 6,190,382 B1 | 2/2001 | Ormsby et al. |
| 6,193,713 B1 | 2/2001 | Geistert et al. |
| 6,196,059 B1 | 3/2001 | Kosslinger et al. |
| 6,197,023 B1 | 3/2001 | Muntermann |
| 6,200,269 B1 | 3/2001 | Lin et al. |
| 6,200,315 B1 | 3/2001 | Gaiser et al. |
| 6,203,525 B1 | 3/2001 | Whayne |
| 6,203,531 B1 | 3/2001 | Ockuly et al. |
| 6,206,831 B1 | 3/2001 | Suorsa |
| 6,212,426 B1 | 4/2001 | Swanson |
| 6,217,576 B1 * | 4/2001 | Tu et al. ....................... 606/41 |
| 6,231,561 B1 | 5/2001 | Frazier |
| 6,235,025 B1 | 5/2001 | Swartz et al. |
| 6,237,605 B1 | 5/2001 | Vaska et al. |
| 6,241,754 B1 | 6/2001 | Swanson et al. |
| 6,245,064 B1 | 6/2001 | Lesh et al. |
| 6,251,109 B1 | 6/2001 | Hassett et al. |
| 6,254,599 B1 | 7/2001 | Lesh et al. |
| 6,280,402 B1 | 8/2001 | Ishibashi et al. |
| 6,282,949 B1 | 9/2001 | Axelsson |
| 6,283,127 B1 | 9/2001 | Sterman et al. |
| 6,290,674 B1 | 9/2001 | Roue et al. |
| 6,305,378 B1 | 10/2001 | Lesh |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,778 B1 | 11/2001 | Gambale et al. |
| 6,330,473 B1 | 12/2001 | Swanson et al. |
| 6,332,880 B1 | 12/2001 | Yang et al. |
| 6,355,051 B1 | 3/2002 | Sisskind et al. |
| 6,383,151 B1 | 5/2002 | Diederich et al. |
| 6,398,792 B1 | 6/2002 | O'connor |
| 6,461,314 B1 | 10/2002 | Pant et al. |
| 6,491,710 B2 | 12/2002 | Satake |
| 6,492,762 B1 | 12/2002 | Pant et al. |
| 6,500,174 B1 | 12/2002 | Maguire et al. |

| | | | |
|---|---|---|---|
| 6,513,385 | B1 | 2/2003 | Han et al. |
| 6,514,246 | B1 * | 2/2003 | Swanson et al. ............ 606/41 |
| 6,517,536 | B2 | 2/2003 | Hooven et al. |
| 5,840,066 | A1 | 3/2003 | Test |
| 6,123,456 | A1 | 3/2003 | Test |
| 6,540,744 | B2 * | 4/2003 | Hassett et al. ............ 606/45 |
| 6,543,274 | B1 | 4/2003 | Herrmann et al. |
| 6,589,274 | B2 | 7/2003 | Stiger et al. |
| 6,607,476 | B1 | 8/2003 | Barnhart |
| 6,626,861 | B1 | 9/2003 | Hart et al. |
| 6,635,054 | B2 * | 10/2003 | Fjield et al. ............ 606/27 |
| 6,642,515 | B1 | 11/2003 | Yamaguchi |
| 6,652,515 | B1 | 11/2003 | Maguire et al. |
| 6,764,486 | B2 * | 7/2004 | Natale ............ 606/41 |
| 6,808,524 | B2 | 10/2004 | Lopath et al. |
| 6,837,886 | B2 * | 1/2005 | Collins et al. ............ 606/41 |
| 7,189,229 | B2 | 3/2007 | Lopath et al. |
| 2002/0065512 | A1 * | 5/2002 | Fjield et al. ............ 606/27 |
| 2003/0013968 | A1 | 1/2003 | Fjield et al. |
| 2003/0050637 | A1 | 3/2003 | Maguire et al. |
| 2004/0054362 | A1 | 3/2004 | Lopath et al. |
| 2004/0068257 | A1 | 4/2004 | Lopath et al. |

FOREIGN PATENT DOCUMENTS

| | | |
|---|---|---|
| JP | 07-178173 | 7/1995 |
| JP | 2002-078809 | 3/2002 |
| WO | WO-90/00420 | 1/1990 |
| WO | WO-98/41178 | 9/1998 |
| WO | WO-98/49957 | 11/1998 |
| WO | WO-98/52465 | 11/1998 |
| WO | WO-99/02096 | 1/1999 |
| WO | WO-99/44519 | 9/1999 |
| WO | WO 99/44523 | 9/1999 |
| WO | WO-99/52423 | 10/1999 |
| WO | WO-99/56812 | 11/1999 |
| WO | WO-00/16850 | 3/2000 |
| WO | WO-00/27292 | 5/2000 |
| WO | WO-00/42934 | 7/2000 |
| WO | WO-00/51511 | 9/2000 |
| WO | WO-00/51683 | 9/2000 |
| WO | WO-00/56237 | 9/2000 |
| WO | WO-00/67648 | 11/2000 |
| WO | WO-00/67656 | 11/2000 |
| WO | WO-00/67830 | 11/2000 |
| WO | WO-00/67832 | 11/2000 |
| WO | WO 01/82814 A2 | 11/2001 |
| WO | WO 02/05868 A2 | 1/2002 |
| WO | WO 02/083196 A2 | 10/2002 |
| WO | WO-2004/023978 A2 | 3/2004 |

OTHER PUBLICATIONS

Chinitz, Larry A., "Mapping Reentry Around Atriotomy Scars Using Double Potentials," 1996.

Cosio, Francisco G., "Atrial Flutter Mapping and Ablation II," Pacing & Clin. Electrophysiol. 19(6):965-75, 1996.

Feld, Gregory K., "Radiofrequency Catheter Ablation for the Treatment of Human Type I Atrial Flutter," 1992.

Fjield, et al., U.S. Appl. No. 60/218,641, filed Jul. 13, 2000.

Gallagher, John J., "Wolff-Parkinson-White Syndrome: Surgery to Radiofrequency Catheter Ablation," 1997.

Haissaguerre, Michel, "Electrophysiological End Point for Catheter Ablation of Atrial Fibrillation Initiated From Multiple Venous Foci," 1999.

Haissaguerre, Michel, M.D., "Predominant Origin of Atrial Panarythmic Triggers in the Pulmonary Veins: A Distinct Electrophysiologic Entity," 1997.

Haissaguerre, Michel, M.D., "Radiofrequency Catheter Ablation in Unusual Mechanisms of Atrial Fibrillation," 1994.

Haissaguerre, Michel, M.D., "Right and Left Atrial Radiofrequency Catheter Therapy of Paroxysmal Atrial Fibrillation," 1996.

Haissaguerre, Michel, M.D., "Spontaneous Initiation of Atrial Fibrillation by Ectopic Beats Originating in the Pulmonary Veins," 1998.

Hatala, Robert, "Radiofrequency Catheter Ablation of Left Atrial Tachycardia Originating Within the Pulmonary Vein in a Patient with Dextrocardia," 1996.

Hocini, Meleze, "Concealed Left Pulmonary Vein Potentials Unmasked by Left Atrial Stimulation," 2000.

Hocini, Meleze, "Multiple Sources Initating Atrial Fibrillation from a Single Pulmonary Vein Identified by a Circumferential Catheter," 2000.

Hsieh, Ming-Hsiung, M.D., "Double Multielectrode Mapping Catheters Facilitate Radiofrequency Catheter Ablation of Focal Atrial Fibrillation Originating from Pulmonary Veins," 1998.

Jais, Pierre, M.D., "A Focal Source of Atrial Fibrillation Treated by Discrete Radiofrequency Ablation," 1996.

Kay, G. Neal, "Radiofrequency Ablation for Treatment of Primary Atrial Tachycardia," 1993.

Krimholtz et al., "New Equivalent Circuits for Elementary Piezoelectric Transducers," Electronics Lettres, vol. 6, No. 13, pp. 398-399, Jun. 25, 1970.

Kumagai, Koichiro, "Treatment of Mixed Atrial Fibrillation and Typical Atrial Flutter by Hybrid Catheter Ablation," 2000.

Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.

Lesh, Michael D., M.D., "Radiofrequency Catheter Ablation of Atrial Arrhythmias," 1994.

Liem, L. Bing, "In Vitro and In Vivo Results of Transcatheter Microwave Ablation Using Forward-Firing Tip Antenna Design," 1996.

Lin, Wei-Shiang, M.D., "Pulmonary Vein Morphology in Patients with Paroxysmal Atrial Fibrillation Initiated by Ectopic Beats Originating From the Pulmonary Veins," Circulation 101(11):1274-81, 2000.

Mallavarapu, Christopher, "Radiofrequency Catheter Ablation of Atrial Tachycardia with Unusual Left Atrial Sites of Origin," 1996.

Montenero, Sandro, Annibale, "Electrograms for Identification of the Atrial Ablation Site During Catheter Ablation of Accessory Pathways," 1996.

Moubarak, Jean B., "Pulmonary Veins-Left Atrial Junction: Anatomic and Histological Study," Pacing & Clin. Electrophys. 23(11 Pt. 2):1836-8, 2000.

O'Connor, Brian K., "Radiofrequency Ablation of a Posteroseptal Accessory Pathway Via the Middle Cardia Vein in a Six-Year Old Child," 1997.

Prager, Nelson, A., "Long Term Effectiveness of Surgical Treatment of Ectopic Atrial Tachycardia," 1993.

Reuter, David, M.D., "Future Directions of Electrotherapy for Atrial Fibrillation," 1997.

Robbins, Ivan, M.D., "Pulmonary Vein Stenosis Alter Catheter Ablation of Atrial Fibrillation," 1998.

Scheinman, Melvin M., "NASPE Survey on Catheter Ablation," 1995.

Swartz, John F., "A Catheter-based Curative Approach to Atrial Fibrillation in Humans," 1994.

Swartz, John F., M.D., "Radiofrequency Endocardial Catheter Ablation of Accessory Atrioventricular Pathway Atrial Insertion Sites," 1993.

Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.

Van Hare, George F., "Radiofrequency Catheter Ablation of Supraventricular Arrhythmias in Patients With Congenital Heart Disease: Results and Technical Considerations," J. of the Amer. College of Cardiol. 22(3):883-90, 1993.

Volkmer, Marius, M.D., "Focal Atrial Tachycardia from Deep Inside the Pulmonary Veins," 1997.

Walsh, Edward P., M.D., "Transcatheter Ablation of Ectopic Atrial Tachycardia in Young Patients Using Radiofrequency Current," 1992.

Zipes, Douglas P., M.D., "Catheter Ablation of Arrhythmias," 1994.

Tanaka et al., "A new radiofrequency thermal balloon catheter for pulmonary vein isolation," Journal of the American College of Cardiology 38(7): 2079-86, Dec. 2001.

Zhang et al., "The development of a RF electrical pole catheter for heart ablation," China Academic Journal Electronic Publishing House 23(5): 279-80, Sep. 1999.

* cited by examiner

CARDIAC ABLATION DEVICES

CROSS-REFERENCE TO RELATED APPLICATIONS

The present application claims benefit of U.S. Provisional Patent Application Ser. No. 60/448,804, filed Feb. 20, 2003, the disclosure of which is hereby incorporated by reference herein.

BACKGROUND OF THE INVENTION

The present invention relates to ablation apparatus and methods and to steerable devices, including those used in cardiac ablation Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue along a path crossing a route of abnormal conduction, either by surgically cutting the tissue or applying energy or chemicals to the tissue, so as to form scar. The scar blocks the abnormal conduction. For example, in treatment of AF it has been proposed to ablate tissue in a partial or complete loop around a pulmonary vein within the vein itself near the ostium of the vein; within the ostium; or within the wall of the heart surrounding the ostium. It would be desirable to perform such ablation using a catheter-based device which can be advanced into the heart through the patient's circulatory system.

As described in co-pending, commonly assigned U.S. Patent Application Ser. No. 09/905,227, published as US/2002/0065512-A1 (the "'512 publication") and granted as U.S. Pat. No. 6,635,054, the disclosures of which are hereby incorporated by reference herein, an expansible structure is used as a reflector for directing and focusing ultrasonic waves from an ultrasonic transducer into a region of tissue to be ablated. As further described in the '512 publication, certain preferred embodiments according to that disclosure include an expansible structure incorporating a structural balloon which is inflated with a liquid and a reflector balloon inflated with a gas. The balloons share a common wall. The balloons are configured so that the common wall has a generally parabolic shape. Because the liquid in the structural balloon and the gas in the reflector balloon have substantially different acoustic impedances, the interface between the balloons at the common wall is a nearly perfect reflector for ultrasonic waves. Ultrasonic waves are emitted from a small transducer within the structural balloon and passes radially outwardly from the emitter to the reflector. The reflector redirects the ultrasonic waves and focuses it into a ring-like ablation region encircling the central axis of the emitter and balloons. This ablation region is just forward of the structural balloon. Thus, the ultrasonic waves will ablate tissue in a region encircling the central axis or forward-to-rearward axis of the balloon structure.

This arrangement can be used, for example, to treat atrial fibrillation by ablating a circular region of myocardial tissue encircling the ostium of a pulmonary vein. The ablated tissue forms a barrier to abnormal electrical impulses which can be transmitted along the pulmonary veins and, thus, isolates the myocardial tissue of the atrium from the abnormal impulses. To provide effective treatment in this mode of operation, the ring-like focal region should encircle the ostium and should lie in a plane which is parallel or nearly parallel with the inner surface of the heart. In some embodiments disclosed in the '512 publication, the structural balloon is provided with a forwardly projecting tip at its central or forward-to-rearward axis, so that by engaging the tip in the lumen of the pulmonary vein, the forward-to-rearward axis of the balloon structure can be placed at the center of the ostium. A guide wire can be threaded into the pulmonary vein. The balloon is then advanced along the guide wire until the tip lodges in the ostium in the pulmonary vein. Where the particular pulmonary vein being treated has a main trunk which extends generally perpendicular to the interior surface of the heart wall, and where the ostium has the expected configuration, this arrangement works properly.

However, there is significant variability in the anatomy of the pulmonary veins and their ostia. For example, that portion of the pulmonary vein adjacent the ostium may lie at an oblique angle to the interior surface of the heart wall. In order to engage the tip of the structural balloon in such an ostium, the forward-to-rearward axis of the balloon must be tilted at a comparable angle, so that the ablation region is unintentionally tilted relative to the interior surface of the heart wall. Also, two or more pulmonary veins may join one another close to a common opening or ostium or may be enlarged or shaped so that it is difficult to engage the tip in the ostium. Moreover, even where the patient has the desired, nominal anatomy, it has been difficult to confirm proper placement of the balloon assembly. Thus, still further improvements would be desirable.

The delicate tissues within the pulmonary vein can be damaged by forcibly engaging structures with these tissues and by moving the engaged structures while the structures are forcibly engaged with the tissues. It would be desirable to provide an improved system and method which does not rely on such forcible engagement to orient the balloon or other ablation device in the desired disposition. Further, it is often necessary or desirable to move an ablation device to several different dispositions within the heart chamber. For example, the treatment plan may require formation of loop-like lesions around the individual ostium of each of several pulmonary veins. It would be desirable to provide apparatus and methods which facilitate such repositioning.

Further, it has been proposed that more effective treatment can be provided by ablated generally linear lesions along the heart wall in conjunction with loop-like lesions. However, heretofore it has been proposed to form the linear lesions using specialized devices as, for example, catheters equipped with a point energy source such as a single pair of electrodes for applying RF energy, so that the linear lesion can be traced by moving the catheter so as to move the single point source along the heart wall or, alternatively, by catheters equipped with numerous energy emitters such as numerous RF electrodes disposed along the length of the catheter. Such a catheter may be provided as a separate device which must be separately introduced into the heart, thus complicating and prolonging the procedure. Alternatively, it has been proposed to provide such a catheter as a portion of a catheter carrying a device for forming a loop-like lesion. Although this approach theoretically simplifies the task of positioning the needed devices within the heart, in fact, it substantially complicates the construction of the device and also complicates the tasks of positioning each individual device. Thus, further improvement in this regard would also be desirable.

Moreover, further improvements in construction of expansible ablation devices, including balloon-based ablation devices, would be helpful. In particular, it would be desirable to provide improved structures which facilitate cooling of a piezoelectric ultrasonic emitter, and structures which can reinforce the expansible device when the same is in an expanded condition. It would also be desirable to provide a back-up system which would minimize the consequences in the unlikely event of a structural failure in one or more components of the device. It would be desirable to provide these improvements without substantially increasing the diameter of the expansible ablation device when the same is in a collapsed condition.

SUMMARY OF THE INVENTION

The various aspects of the present invention address these needs.

One aspect of the present invention provides apparatus for performing cardiac ablation in a mammalian subject. Apparatus according to this aspect of the invention includes an insertable structure which incorporates a catheter having proximal and distal ends, as well as an ablation device mounted to the catheter adjacent the distal end thereof. The ablation device is adapted for placement within a chamber of the heart of the subject and is adapted to ablate a region of the cardiac structure bounding the chamber when the ablation device is in an operative configuration. The insertable structure also defines an outlet port open to a distal side of the ablation device, i.e., that side of the ablation device furthest from the proximal end, and further defines a continuous passageway extending from adjacent the proximal end of the catheter. Most preferably, the apparatus according to this aspect of the invention further includes a source of a contrast medium adapted for connection to the passageway adjacent the proximal end of the catheter. The source of contrast medium is operative to pass contrast medium through the passageway and into the subject through the outlet port while the ablation device is in its operative condition.

Most preferably, the ablation device includes an expansible structure which may be, for example, a balloon structure as discussed above. The expansible structure has a collapsed, inoperative state and an expanded state. The ablation device is in the operative condition when the expansible structure is in its expanded state.

A method according to a related aspect of the invention includes the step of providing an ablation device in a chamber of the heart of a mammalian subject, such that the device is in an operative configuration with a distal side of the device facing toward a region of the cardiac structure to be ablated, and, while the ablation device is in its operative configuration, injecting a contrast medium into the chamber on the distal side of the ablation device. The method most desirably further includes obtaining one or more images depicting the contrast medium in at least a portion of the cardiac structure as, for example, by x-ray or fluoroscopic imaging. Methods according to this aspect of the invention allow the physician to confirm placement of the device while the device is in its operative condition as, for example, while a balloon or other expansible structure is in its expanded state. Most preferably, the methods according to this aspect of the invention are performed without introducing a separate catheter to carry the contrast medium, as by using the continuous passageway discussed above in connection with the apparatus. The methods according to this aspect of the invention may further include the step of adjusting the position of the ablation device, based in part or entirely on the relationship between the ablation device and the cardiac structure observed in the imaging step. These methods allow the physician to position the device during the procedure, without relying on a predetermined mechanical relationship between the device and the cardiac structure.

Apparatus according to a further embodiment of the invention includes a catheter and an ultrasonic device having a forward-to-rearward axis. The ultrasonic device is arranged to emit ultrasonic waves so that the emitted ultrasonic waves are directed into at least a portion of a ring-like region surrounding the forward-to-rearward axis. The ablation device is mounted to the catheter. Apparatus according to this aspect of the invention includes a steering system adapted to selectively vary the disposition of the ablation device and, in particular, the disposition of the forward-to-rearward axis of the ablation device relative to the heart of the subject, while the ultrasonic ablation device is disposed in a chamber of the heart of the subject. Here again, the ultrasonic ablation device most preferably includes an expansible structure such as a balloon structure having a collapsed, inoperative state and an expanded state. The steering system preferably is operative to selectively vary the disposition of the ablation device while the expansible structure is in its expanded state as, for example, while a balloon-based expanded structure is in an inflated condition. Most preferably, the steering system is arranged to selectively vary the disposition of the ultrasonic ablation device independently of engagement between the cardiac structure and any element of the apparatus distal to the ultrasonic ablation device. Most preferably, the catheter has a bendable section located proximally or rearwardly of the forward end of the ablation device, and the steering system is arranged to selectively bend this bendable section of the catheter under the control of the physician. In a particularly preferred arrangement, the expansible structure includes an internal reinforcing structure having a distal end linked to the expansible structure adjacent the forward end of the expansible structure, and having a proximal end mechanically linked to the expansible structure adjacent the rearward end thereof. The reinforcing structure may include an ultrasonic emitter assembly, as well as an extensible structure. Preferably, the reinforcing structure becomes relatively flexible when the expansible structure is in a collapsed condition and becomes more rigid when the expansible structure is in its expanded condition. As further discussed below, this arrangement allows the reinforcing structure to maintain the shape of the expansible structure in its expanded or inflated condition, but facilitates threading of the device through the body to the heart.

The steering system most desirably includes at least one pull wire mechanically connected to the reinforcing structure, typically adjacent the proximal end thereof. As further discussed below, steering by pulling on the internal reinforcing structure within the expansible structure tends to bend the catheter in such a way that the expansible structure turns about a pivot axis relatively close to the forward end of the expansible structure. This makes it easier to maneuver the expanded structure within the confines of a heart chamber.

A method of cardiac ablation according to a related aspect of the present invention includes the steps of advancing apparatus including a catheter bearing an ultrasonic ablation device into the subject until the ultrasonic ablation device is within a chamber of the heart and positioning the ultrasonic ablation device in a first disposition within the chamber by selectively varying the disposition of the forward-to-rearward axis of the ultrasonic ablation device relative to the catheter, and then while the ultrasonic ablation device is in this first disposition, ablating the heart wall to form a first lesion by actuating the ablation device to direct ultrasonic waves into at least a portion of a ring-like region surrounding the forwardto-rearward axis of the device. The method also includes the step of removing the ultrasonic ablation device from the subject. Most preferably, the method further includes the step of repositioning the ultrasonic ablation device from the first disposition to a different, second disposition within the chamber by further selectively varying the disposition of the forward-to-rearward axis relative to the catheter, and, while the device is in the second disposition, ablating the heart wall to form a second lesion, again by actuating the ablation device to direct ultrasonic waves into the ring-like region. Most desirably, the repositioning and additional ablation steps are performed prior to removal of the device. The device remains within the chamber, and most preferably remains in an expanded, operative condition, while it is repositioned. Additional repositioning and actuating steps may be employed as well, so as to form further lesions.

Desirably, at least one of the dispositions of the ablation device is a so-called "normal" disposition in which the forward-to-rearward axis of the device lies approximately perpendicular to a wall of the heart with at least a major portion of the ring-like ablation region disposed within or in close proximity to the wall of the heart. Ablation in this disposition forms a lesion in the form of at least a substantial portion of a loop. Alternatively or additionally, at least one of the dispositions may be a canted disposition in which the forward-to-rearward axis of the device lies at a substantially non-perpendicular angle to the wall of the heart, so that only a minor portion of the ring-like region is disposed within or in close proximity to the wall of the heart. Ablation in this disposition forms a lesion in the form of only a small portion of a loop, approximating a linear lesion. Thus, the same tool can be used to form both loop-like lesions and substantially linear lesions. Most desirably, the ablation device is arranged to focus the ultrasonic waves into the ring-like ablation region, so that the ultrasonic waves have intensity which increases in the direction of propagation of the energy from the device to the ablation region and decreases in the same direction, beyond the ablation region. Typically, the ultrasonic waves are directed indiscriminately into the entire ablation region. In the normal disposition, all or almost all of this energy performs the desirable function of ablating the loop-like lesion. However, in the canted disposition, only a portion of the ablation region is disposed where ablation is desired. Other portions of the ablation region typically are disposed remote from a heart wall to be ablated. However, ultrasonic waves directed into those remote portions of the ablation region will pass through the ablation region and will dissipate, typically without damaging other structures.

Yet another aspect of the invention provides an ultrasonic ablation device including an ultrasonic emitter assembly which has proximal and distal ends. The emitter assembly includes a tubular piezoelectric element having proximal and distal ends and a tube, referred to herein as the "inside tube," extending within the tubular piezoelectric element, so that the inside tube and the piezoelectric element cooperatively define an annular passageway extending between the proximal and distal ends of the piezoelectric element. The apparatus desirably further includes a balloon having an interior space. The annular passageway inside the piezoelectric element communicates with the interior of the balloon adjacent the distal end of the emitter assembly. The apparatus most preferably further includes a catheter having proximal and distal ends. The catheter has a first lumen, referred to herein as a principal lumen, most typically disposed adjacent the center of the catheter, and also has first and second additional lumens. The principal lumen communicates with the bore of the inside tube. The first additional lumen communicates with the proximal end of the annular passageway, and the second additional lumen communicates with the interior of the balloon adjacent the proximal end of the emitter assembly. The emitter assembly may include a proximal mounting structure disposed at least partially between the distal end of the catheter and the proximal end of the tubular piezoelectric element. The proximal mounting structure desirably defines a first channel which connects the first additional lumen of the catheter with the annular passageway, a second channel communicating with the second additional lumen of the catheter and a port communicating with the second channel and with the interior of the balloon, so that the second additional lumen communicates with the interior of the balloon through the port.

In the preferred apparatus according to this aspect of the invention, the piezoelectric element can be cooled by directing liquid through the first additional lumen of the catheter and through the annular channel inside the piezoelectric element. The liquid passes from the annular channel into the interior of the balloon, passes through the interior of the balloon back through the port and into the second additional lumen of the catheter. The principal lumen of the catheter and the bore of the inside tube desirably define a portion of the continuous passageway discussed above. Because the principal lumen is not employed in circulation of the cooling liquid, it remains free for purposes such as introduction of a contrast medium. The emitter assembly may also include a distal mounting element mounted to the distal end of the piezoelectric element. The mounting elements may be electrically conductive and may serve as electrical pathways to the piezoelectric element. Moreover, a pull wire may be connected to one of the mounting structures, typically to the proximal mounting structure, so as to provide the desired bending action as discussed above. The apparatus may further include an extensible element. As further discussed below, the extensible reinforcing element may include elements which cooperate with the distal mounting structure.

Still other aspects of the invention provide alternative structures and methods.

DETAILED DESCRIPTION

Figure 1:
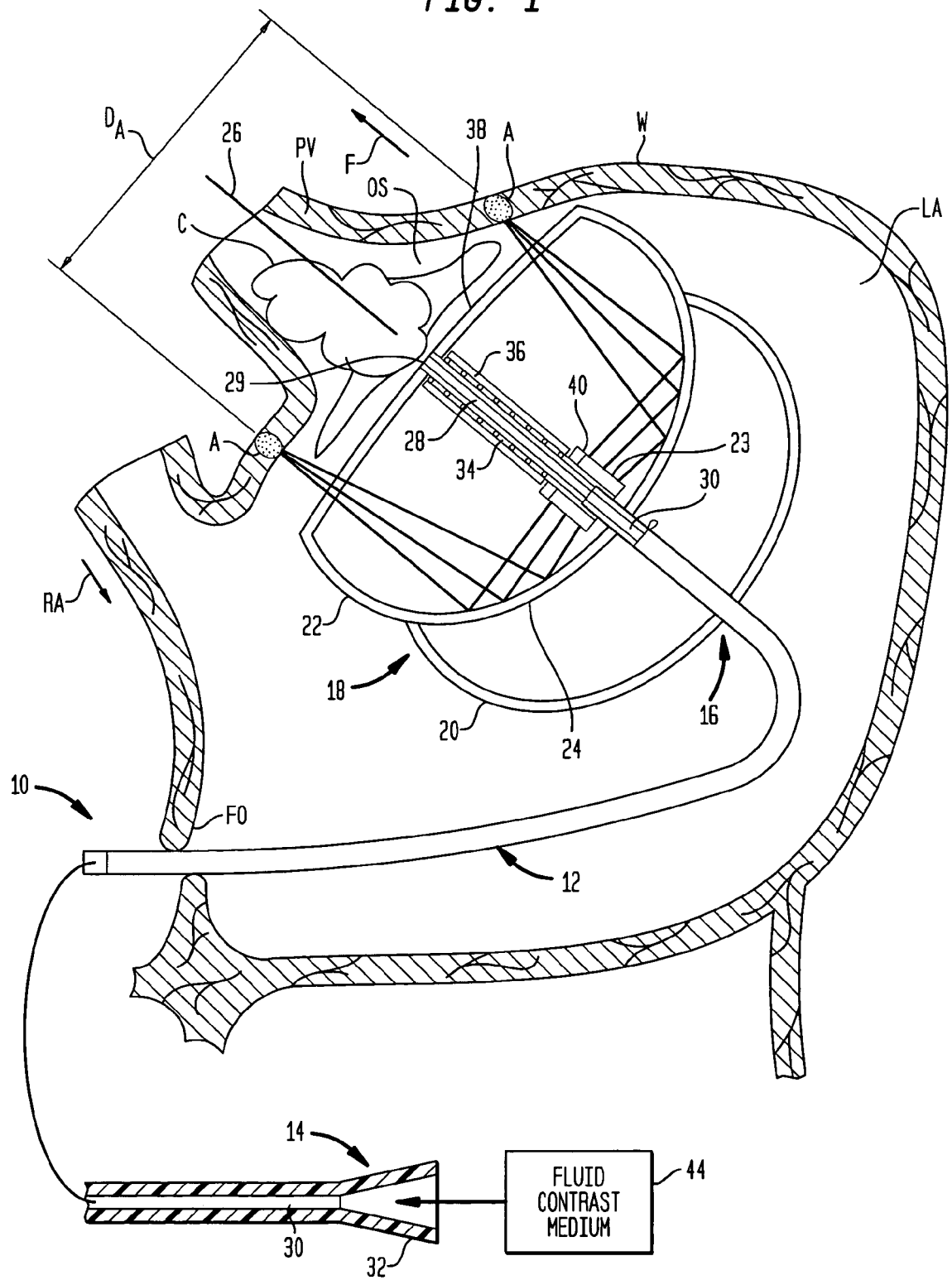
FIG. 1 is a diagrammatic view depicting a catheter and ablation device in accordance with one embodiment of the invention, in conjunction with certain features of a heart.

As seen in FIG. 1, apparatus according to one embodiment of the invention includes an insertable structure 10 incorporating an elongated catheter 12 having a proximal end 14, which remains outside of the body, and a distal end 16 adapted for insertion into the body of the subject. As used in this disclosure with reference to structures which are advanced into the body of a subject, the "distal" end of such a structure should be taken as the end which is inserted first into the body and which penetrates to the greatest depth within the body, whereas the proximal end is the end of the structure opposite to the distal end. The insertable structure 10 also includes an ablation unit 18 mounted to the catheter adjacent distal end 16. Ablation unit 18 incorporates a reflector balloon 20 and a structural balloon 22 having a common wall 24. Reflector balloon 20 is linked to an inflation lumen (not shown) in catheter 10, which extends to the proximal end of the catheter and which is connected, during use, to a source of a gas under pressure, such as air or, more preferably, carbon dioxide, as, for example, to a gas-filled hypodermic syringe, so that the reflector balloon can be inflated with a gas. Structural balloon 22 is connected through a separate inflation lumen (also not shown) to a source of a liquid such as isotonic saline solution, so that structural balloon 22 can be inflated with the liquid. A cylindrical ultrasonic emitter 23 is mounted within the structural balloon. Balloons 20 and 22, and particularly the common wall 24 separating the balloons, are designed so that in their inflated, operative condition illustrated in FIG. 1, the balloons are in the form of bodies of revolution about a central or forward-to-rearward axis 26. Emitter 23 is cylindrical and is coaxial with the balloons.

A tube 28 extends through the structural balloon at the central axis 26. Tube 28 defines a port 29 on or forward of the forward wall 38 of the structural balloon. Tube 28 communicates with a lumen 30 within catheter 12. Lumen 30 extends to the proximal end 14 of the catheter and is provided with a suitable fluid connection such as a Luer hub. The bore of tube 28 and lumen 30 of catheter 16 form a continuous passageway extending from the outlet port 29, just distal to the ablation device back to the proximal end 14 of the catheter. As further described in co-pending, commonly assigned U.S. patent application Ser. No. 10/244,271, filed Sep. 16, 2002, published as US/2004/0068257-A1 ("the '257 application") the disclosure of which is incorporated by reference herein, tube 28 may be formed from a material such as an expanded polymer of the type commonly used in vascular grafts, so that the interior bore of the tube remains patent when the tube is stretched. As also disclosed in the '257 application, a coil spring 34 may be provided within the structural balloon, such that the coil spring surrounds tube 28. A reinforcing structure which may include one or more rigid tubes of metal or a rigid polymer such as polyether ether ketone ("PEEK") 36 desirably surrounds tube 28 and spring 34. As described in greater detail in the '257 application, the spring is compressed when the balloons are in the inflated, operative state. When the balloon is deflated, the spring expands and moves the forward wall 38 of the structural balloon in the forward or distal direction F (up and to the left, as seen in FIG. 1) relative to the rearward or proximal end of the balloon and relative to the catheter 12, thereby collapsing the balloon in a radial direction, and also twists the balloons about axis 26 to facilitate radial collapse and formation of a small, radially compact unit for withdrawal from the patient. However, when the balloons are inflated, the spring is compressed and reinforcing element 36 engages a rigid mounting 40 attached to the distal end 16 of the catheter, which mounting also holds ultrasonic emitter 23. This assures that the axis 26 of the balloon structure is precisely aligned with the axis of the emitter and reinforces the balloon against deflection transverse to the axis 26.

In the arrangement depicted in FIG. 1, the tubular reinforcing element 36 abuts the distal end of the mounting 40. In a variant, the mounting is telescopically received within the tubular reinforcing element. Thus, as the balloons are inflated, the tubular reinforcing element 36 moves proximally or rearwardly so that the distal end of the mounting 40 enters into the tubular reinforcing element before the balloons are fully inflated. In the fully-inflated condition, the tubular reinforcing element remains slightly distal or forward of the transducer 23 or else abuts the distal end of the transducer. Telescopic engagement between the mounting and the reinforcing element helps prevent kinking or displacement of the structure transverse to axis 26 when the structure is in a partially-inflated or fully-inflated condition.

As discussed in the '257 application and in the '512 publication, the common wall 24 separating the balloons forms an active, reflective interface. This active interface desirably has the form of a surface of revolution of a parabolic section around the central axis 26. When the balloons are in their inflated, operative configuration shown in FIG. 1, ultrasonic waves emitted by emitter 23 are directed radially outwardly away from axis 26 and impinge on the parabolic active interface 24, where it is reflected forwardly and slightly outwardly away from axis 26 and focused so that the ultrasonic waves emitted along various paths mutually reinforces within a ring-like ablation region A, just forward of the forward wall 38 of the structural balloon encircling axis 26. The focused ultrasonic waves in this region can effectively ablate myocardial tissue and form a substantial conduction block extending through the heart wall in a relatively short time, typically about a minute or less.

In a method according to one aspect of the present invention, the apparatus is positioned within a chamber of the heart as, for example, within the left atrium LA of a subject to be treated. A guide sheath (not shown) is advanced through the venous system into the right atrium and through the septum separating the right atrium and left atrium, so that the guide sheath provides access to the left atrium. Typically, the apparatus is advanced through the guide sheath with the balloons in a deflated condition. The threading operation may be performed by first threading a guide wire (not shown) into the heart, then advancing the guide sheath (not shown) over the guide wire, and then advancing the insertable structure 10, with the balloons in a deflated condition, over the guide wire, and through the guide sheath. In this operation, the guide wire passes through tube 28 and through lumen 30. When the apparatus is positioned within the heart so as to place the ablation zone A within the heart wall W and around the ostium OS of a pulmonary vein, the ultrasonic emitter 23 is activated.

According to one aspect of the present invention, the correct positioning of the ablation device can be verified by the use of a contrast medium such as an x-ray contrast medium. After threading, the guide wire may be removed and lumen 30 may be connected, as by Luer fitting 32 to a source 44 of an x-ray contrast medium as, for example, a hypodermic syringe filled with the contrast medium. To verify proper placement of the ablation device, the contrast medium is injected through lumen 30 and passes through the bore of tube 28 and out through port 29 at the forward wall 38 of the structural balloon. The injected contrast medium C has sufficient velocity to carry it distally, into the ostium and into the pulmonary vein. The blood flow in the pulmonary vein PV, directed back toward the ostium and into the left atrium LA, carries the contrast medium back into the left atrium and around the ablation device.

While the contrast medium is injected and during spread of the contrast medium into the left atrium, the patient is imaged using an x-ray imaging modality, most preferably a fluoroscope. This allows the physician to immediately visualize the shape and size of the contrast medium and the position of the ablation device relative to the ostium and relative to the heart wall W. Provided that the positioning is satisfactory, the physician actuates the ultrasonic emitter 23 to emit the ultrasonic waves and ablate the tissue of the heart wall.

In a variant of the procedure discussed above, a thin, tubular stylet 50 (FIG. 2) having an outlet port at its distal end 52 is threaded through the continuous passageway defined by lumen 30 and by the bore of tube 28, so that the distal end 52 of the stylet projects forwardly to the distal end of the balloon. Preferably, the distal end of the stylet does not project substantially beyond the distal end of the balloon, and hence cannot extend substantially into the pulmonary vein. Therefore the stylet cannot damage the lining of the pulmonary vein. The proximal end 54 of the tubular stylet is equipped with a connection such as a hub 56 which, in turn, is connected to the contrast medium source 44. Stylet 50 may serve as the guide wire used in threading the assembly into the patient. Thus, stylet 50 may be placed prior to catheter 12 and ablation device 18. In this case, the connection at proximal end 54 may incorporate a removable hub so that the catheter and ablation device assembly may be threaded over the stylet and then, after the catheter is in place, hub 56 may be added to the proximal end of the stylet. Alternatively, the assembly may be threaded using a conventional guide wire which is then removed and replaced by the stylet. The stylet 50 may be relatively stiff, so that the stylet positions the ablation device relative to the pulmonary vein and relative to the heart. Positioning the balloon at the PV ostium with a stylet is advantageous if there is no clear PV main trunk or the axis of the trunk of the PV is not substantially perpendicular to the wall of the atrium. The distal end 52 of the tubular stylet 50 defines an outlet port for the contrast medium or the distal side of the ablation device. Here again, the contrast medium introduced through the port. When the contrast medium C is introduced into the patient through this port, it permits visualization of the ablation device 18, pulmonary vein PV, ostium OS and heart wall W, in the manner discussed above, thereby allowing the physician to confirm proper position of the device.

In a further variant, a guide wire having an outside diameter smaller than the inside diameter of the catheter lumen 30 and smaller than tube 28 may be left in place while contrast medium is introduced through the continuous passageway defined by the lumen and tube. Because the guide wire does not completely occlude the passageway, the contrast medium can flow through the passageway and pass out of the port 29 in the manner discussed above with reference to FIG. 1.

In yet another variant of the procedures discussed above, the ablation device 18 may be positioned so that the distal wall 38 abuts the heart wall W in the vicinity of the pulmonary vein ostium and thus substantially occludes and thus substantially blocks flow between the pulmonary vein PV and the heart chamber itself. Contrast medium is injected through port 29 of the ablation device itself as discussed with reference to FIG. 1, or through the port 52 of a hollow style as discussed with reference to FIG. 2, while the ablation device is in this blocking position. This increases the concentration of the contrast medium within the pulmonary vein and ostium, and thus facilitates imaging of pulmonary vein and ostium and adjacent structures with a minimal amount of contrast medium. Optionally, the catheter and ablation device may be retracted after acquiring an image of the ostium and vein, allowing the contrast medium to flow into the atrium, and further images may be acquired.

A significant advantage of the procedures discussed above with reference to FIGS. 1 and 2 is that disposition of the ablation device relative to anatomical structures can be verified while the ablation device is in its inflated, operative condition. Such verification can be performed immediately before, during or after application of ultrasonic waves. The ultrasonic waves will propagate effectively through typical liquid x-ray contrast media, inasmuch as the media have acoustic impedance similar to that of other aqueous liquids. There is no need to move any portion of the ablation device or catheter during introduction of the contrast medium and visualization.

Figure 2:
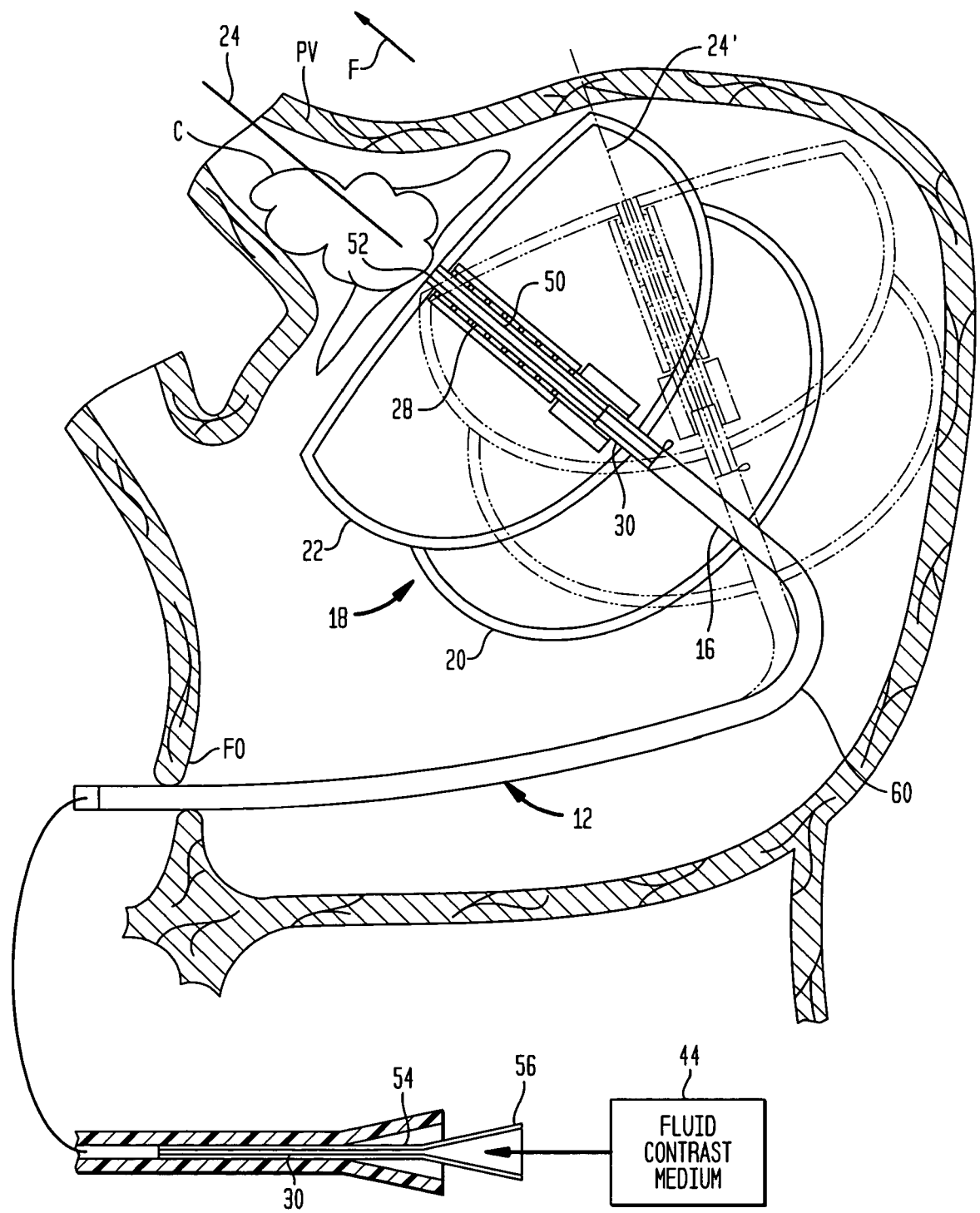
FIG. 2 is a view similar to FIG. 1 depicting apparatus in accordance with another embodiment of the invention.

As also shown in FIG. 2, positioning of the ablation device within the heart desirably includes selectively controlling the disposition of the forward-to-rearward axis 26 of the device relative to the patient's heart. That is, the position of the forward-to-rearward axis desirably can be controlled by the physician to at least some degree. For example, the device may be arranged so that the physician can selectively reorient the forward-to-rearward axis 24 of the ablation device through a range of motion as, for example, through the range between disposition indicated in solid lines by axis 24 and the disposition indicated in broken lines by axis 24'. To that end, the assembly can be provided with one or more devices for selectively varying the curvature of a bendable region 60 of the catheter just proximal to the ablation device.

Figure 3:
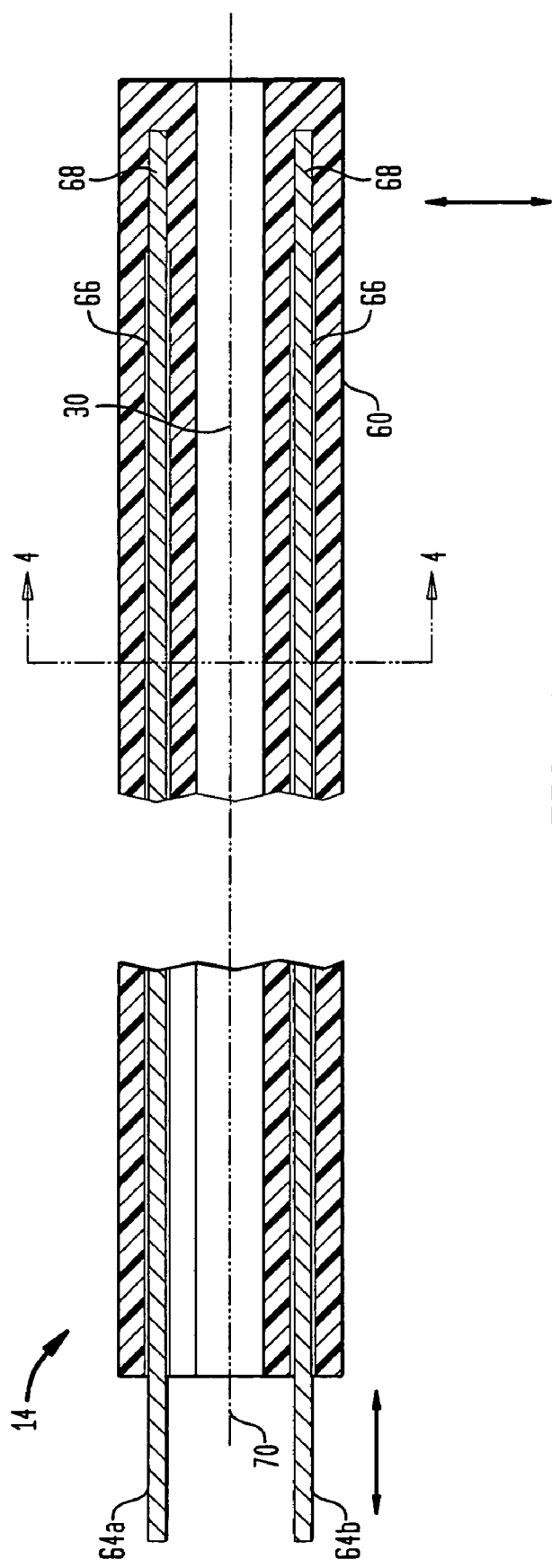
FIG. 3 is a diagrammatic sectional view depicting a portion of a catheter according to one embodiment of the invention.
Figure 4:
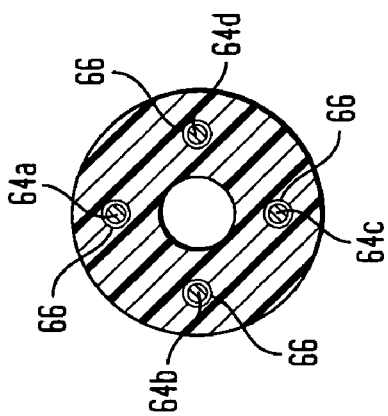
FIG. 4 is a sectional view taken along line 3-3 in FIG. 3.
Figure 5:
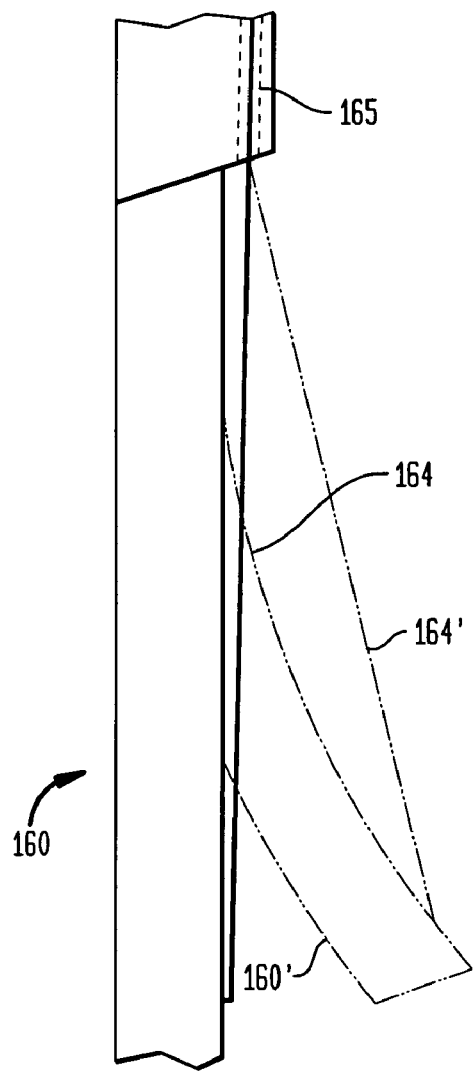
FIG. 5 is a fragmentary, diagrammatic elevational view depicting a portion of an apparatus according to yet another embodiment of the present invention.

In one embodiment, shown schematically in FIGS. 3 and 4, the catheter is provided with one or more pull wires 64. Each such pull wire extends from the proximal end 14 of the catheter in a bore or lumen 66 dimensioned to provide a free-running fit for the pull wire. Each pull wire has a distal end 68 fastened to the catheter wall. The distal ends of the pull wires are disposed at or distal to the bendable region 60. By pulling on a particular wire 64, the bendable region 60 can be bent in the direction toward that particular pull wire. As best seen in FIG. 4, the particular embodiment illustrated has four pull wires disposed in two sets lying in orthogonal planes. The first set includes pull wires 64A and 64B, whereas the second set includes pull wires 64C and 64D. This permits bending of the bendable region in substantially any direction by selectively pulling two of the wires. However, a lesser number of pull wires can be used. For example, a version with three pull wires also permits selective bending in any direction, whereas a version with two diametrically opposite pull wires permits selective bending in either of two opposite directions in a single plane. In an even simpler arrangement, only a single pull wire is provided to provide bending in only a single direction. The catheter itself, or at least the bendable region 60, may be resilient so that it tends to return to a predetermined configuration, such as a straight configuration, when the single pull wire is released. Even a version which permits bending of region 60 in only a single plane provides considerable ability to position the ablation device. For example, the catheter may be "torqueable" or arranged to transmit rotation in the direction around the central axis 70 of the catheter itself. In such an arrangement, combined bending of region 60 and rotation of the catheter about it own axis 70 allows movement of the forward-to-rearward axis of the ablation device towards essentially any desired disposition.

The lumens 66 containing the pull wires 64 may be provided with coil springs (not shown) lining the lumens, so that each pull wire extends though the interior of one such coil spring. The turns of each coil spring form a low-friction liner within the associated lumen. Moreover, the coil springs can provide additional structural reinforcement and resilience to the catheter.

In a variant of this approach, the bendable section 160 of the catheter is attached to one or more pull wires 164 which extend outside of the catheter at the bendable section itself. Each such pull wire may extend through a bore 165 in the catheter proximal to the bendable section. By pulling on wire 164, the bendable section can be deformed to the bent configuration shown in broken lines at 160'. In this configuration, the pull wire 164 extends as a chord 164' across the arc formed by the bendable section. Here again, two or more pull wires may be provided to permit selective deformation in multiple directions, or else a single pull wire can be used in conjunction with a torqueable catheter which can be rotated about its own axis by turning the proximal end of the catheter. In a further variant, the pull wires may extend entirely outside of the catheter. For example, where a guide sheath surrounds the catheter proximal to the bendable section, pull wires may extend within the guide sheath. In a further embodiment, the distal ends of the pull wires can be attached to the ablation device itself, rather than to the catheter. In yet another variant, the pull wires may serve as electrical conductors for energizing the ultrasonic element or for other purposes as, for example, conducting signals to or from sensors used to detect electrical potentials in the heart, electromagnetic position detection devices, ultrasonic or other imaging devices and other electronic components mounted on or near the distal end of the catheter.

Figure 6:
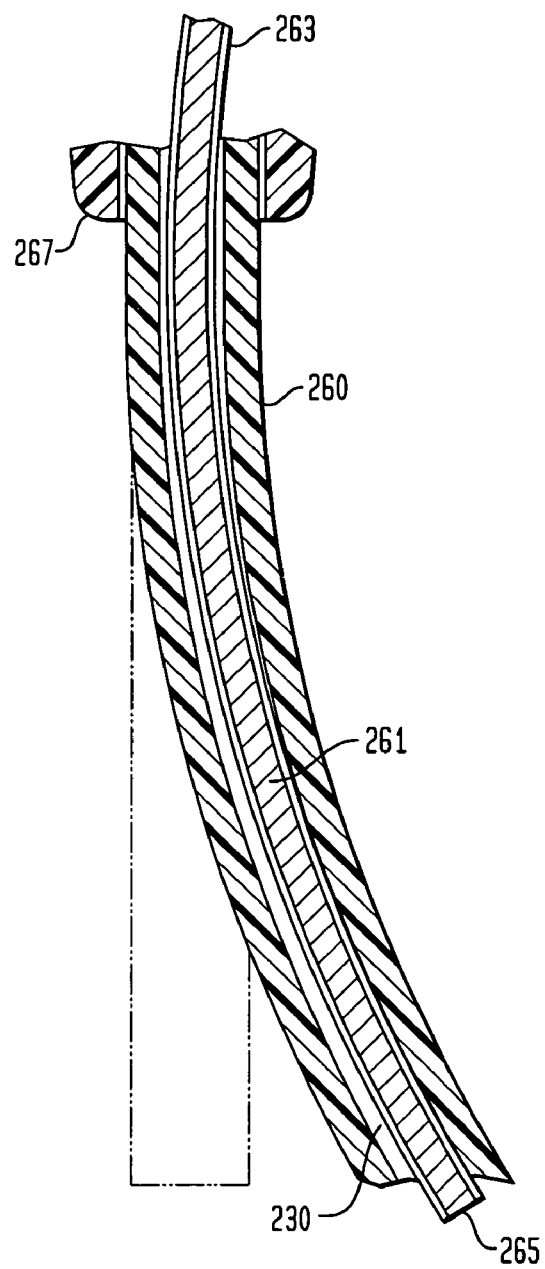
FIG. 6 is a fragmentary sectional view depicting a portion of apparatus according to a further embodiment of the invention.
Figure 7:
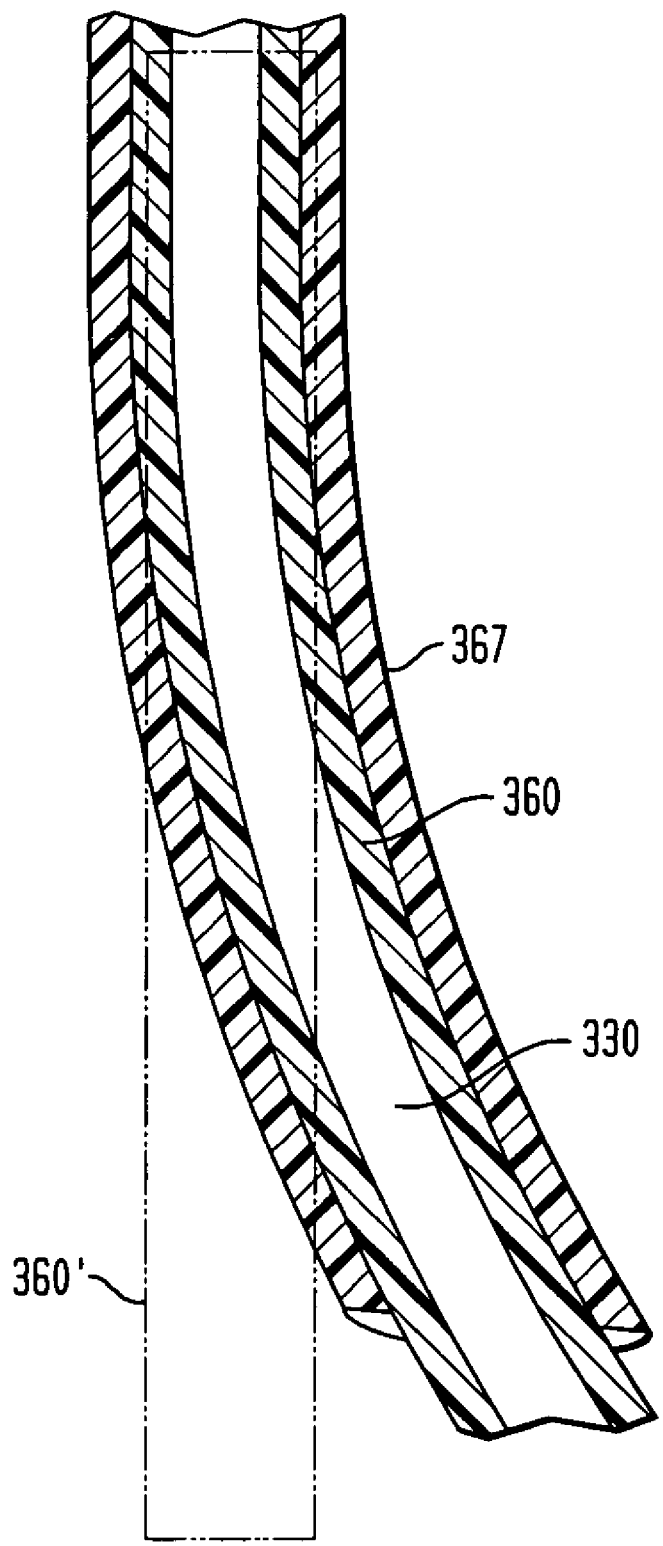
FIG. 7 is a view similar to FIG. 6, but depicting apparatus according to another embodiment of the invention.

As seen in FIG. 6, the bendable section 260 of the catheter may be selectively deformed to the curved shape illustrated in solid lines by advancing a stylet 261 having a predetermined curvature through the lumen 230 of the catheter. The stylet may be formed from a metal or plastic and may be solid or, preferably, hollow, so as to leave a space for introduction of the contrast medium as described above through lumen 230. The stylet may have different properties at different points along its length. Thus, the curved section 261 may be carried by a more flexible section 263 proximal to the curved section and a further, more flexible section 265 may be provided distal to the curved section. Such a stylet may be used as the contrast medium introducing stylet 50 discussed above with reference to FIG. 2. The stylet is positioned so that the curved section 261 is located in the bendable region of the catheter. Prior to introduction of the stylet, the physician may deform curved section 261 to provide a selected degree of curvature. For example, the ablation device may be brought to its expanded, operative condition within the heart and imaged using contrast medium as discussed above, so that the physician can estimate the amount of curvature required in the bendable section to align the device properly with the heart, and the stylet may be curved accordingly and introduced into the catheter. Following introduction of the stylet, the imaging procedure can be repeated to check for proper placement. Desirably, the curved section 261 of the stylet has at least some resilience so that the curved section can be partially or completely straightened during threading, as the curved section is advanced from the proximal end of the catheter to the bendable section. Those sections of the catheter proximal to the bendable section desirably are more rigid than the bendable section. Thus, the bendable section may have a lesser wall thickness or be formed from a more flexible material than the proximal portions of the catheter. Also, the proximal portions of the catheter may be encased in a guide sheath 267, which terminates proximal to the bendable section.

In a further variant, a guide sheath 367 having a selected curvature is advanced over the bendable section 360 of the catheter so as to deform the bendable section from a straight or other configuration 360', shown in broken lines, to a curved configuration, as shown in solid lines, having the selected curvature matching the curvature of the sheath. Sheath 367 extends to the proximal end of the catheter (not shown) so that the sheath can be manipulated while the device is in place. Thus, by advancing or retracting the sheath, the physician can control the degree of curvature of bendable section 360. In another embodiment, the bendable section of the catheter may be resilient and may be curved when in its normal or un-stressed condition, without external loads applied. The bendable section can be straightened during threading through the guide sheath. As the catheter is advanced so that the bendable section protrudes beyond the guide sheath, the bendable section returns to its normal condition. The amount of curvature can be increased by advancing the catheter distally relative to the guide sheath, or decreased by retracting the catheter. The catheter or guide wire also may incorporate a shape memory alloy such as Nitinol (trademark) which tends to assume a predetermined shape when heated to body temperature.

In yet another variant, a sheath may include features which permit steering of the sheath. Such a steerable sheath can be bent in a desired direction and used to bend the catheter in a desired direction. A steerable sheath may be used in conjunction with a steerable catheter. For example, a steerable, torqueable sheath may be used in conjunction with a steerable catheter having a bendable section which is constrained by the sheath and having a further bendable section projecting distally beyond the sheath. Such an arrangement provides a compound steering action, so that two independent bends can be imparted to the catheter. These bends may be in the same plane or in two different planes. In the embodiments discussed above, the catheter is formed separately from the guide sheath used to introduce the catheter into the left atrium. However, this is not essential; the functions of the catheter and the guide sheath may be combined. In such an arrangement, the combined guide sheath and catheter desirably has a distal portion bearing the ablation device and a proximal portion arranged so that the distal portion and the ablation device, including the balloon structure, can be moved between a retracted position in which the ablation device is contained within the proximal portion and an extended position in which the ablation device protrudes from the retracted portion. Where the ablation device incorporates an expansible structure such as the balloon structures discussed above, the expansible structure is in a collapsed condition, and is located near the distal end of the proximal portion, when the distal portion is in the retracted position. The proximal portion desirably has the strength and physical properties required for threading through the vascular system and through the fossa ovalis. The combined structure avoids the need to advance the expansible structure through the entire length of the guide sheath during the procedure.

Figure 8:
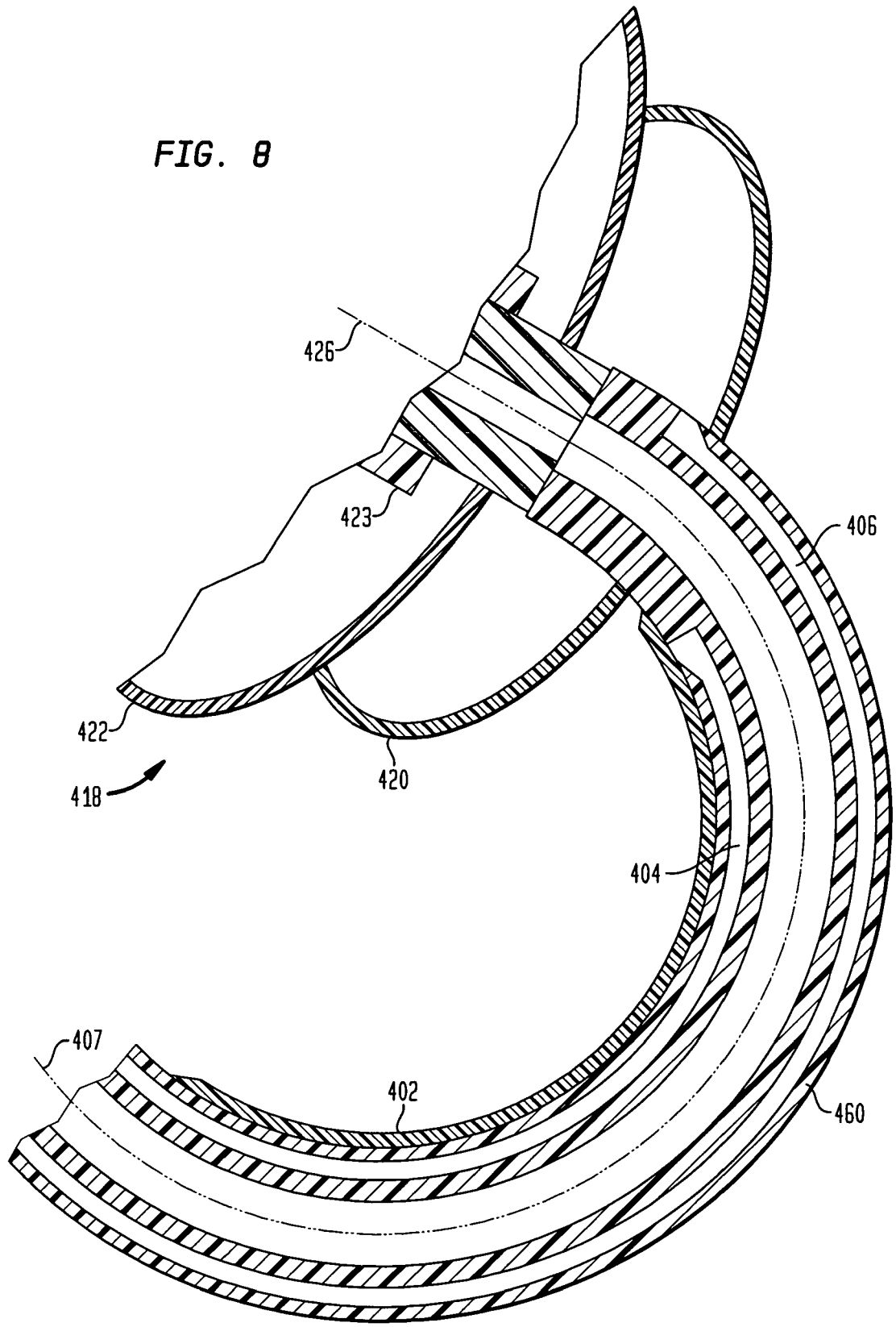
FIG. 8 is a fragmentary sectional view depicting apparatus according to a still further embodiment of the invention.

Apparatus according to a further embodiment of the invention incorporates a catheter having a bendable section 460 which desirably is resilient. The ablation device 418 in this embodiment also includes a structural balloon 422 and reflector balloon 420, and an emitter 423 similar to those discussed above with reference to FIG. 1. An additional inflatable structure 402 is mounted to the bendable section proximal to the ablation device. Inflatable structure 402 is connected to an inflation lumen 404 extending within the catheter to the proximal end thereof. This inflation lumen is separate from the inflation lumen 406 used to inflate the reflector balloon 420 and separate from the inflation lumen (not shown) used to inflate structural balloon 422. With structure 402 deflated, bendable section 460 has a curved configuration as seen in FIG. 8, such that the forward-to-rearward axis 426 of the ablation device lies at an arbitrary angle to the axis 407 of the catheter proximal to the bendable section. However, by inflating structure 402 to the inflated condition 402' (FIG. 9), the bendable section 460 can be straightened so as to substantially align the forward-to-rearward axis 426' of the ablation device 418 with the axis 407 of the catheter proximal to the bendable section. Structure 402 can be inflated using a gas or a liquid. Also, structure 402 need not be fully inflated; by varying the degree of inflation, the physician can control the orientation of the ablation device relative to the heart. To permit selective inflation and deflation of structure 402', the associated inflation lumen 404 extends to the proximal end of the catheter and is connected to a controllable fluid source as, for example, a syringe or other pumping device, or a tank containing fluid under pressure linked to the inflation lumen through a controllable pressure regulator. Bendable section 460 may be resilient so that it tends to assume a curved shape, as seen in FIG. 8, when structure 402 is deflated. Alternatively, the curvature of the bendable section with inflatable structure 402 deflated may be caused by anatomical structures bearing on the ablation device, on the catheter, or both. In either case, inflation of structure 402 will tend to straighten the bendable section and swing the forward-to-rearward axis of the ablation device. In a variant of this approach, the bendable section may be straight when not subjected to external forces and may be deformed to a curved shape by inflation of structure 402.

In a further variant, the separate inflatable structure 402 may be omitted, and pressure differentials within the lumens of the catheter, such as lumens 404 and 406 (FIG. 8) may act to bend or straighten the catheter. For example, if the gas pressure in lumen 404 is less than the gas pressure in lumen 406, the catheter will tend to bend into a curve as depicted in FIG. 8. The reverse pressure differential (higher pressure in lumen 404 than in lumen 406) will tend to straighten the catheter or bend it in a curve opposite to that depicted in FIG. 8. To provide a high differential pressure, one of the lumens may be connected to a vacuum pump whereas another lumen may be connected to a source of a gas or liquid under super-atmospheric pressure.

Figure 10:
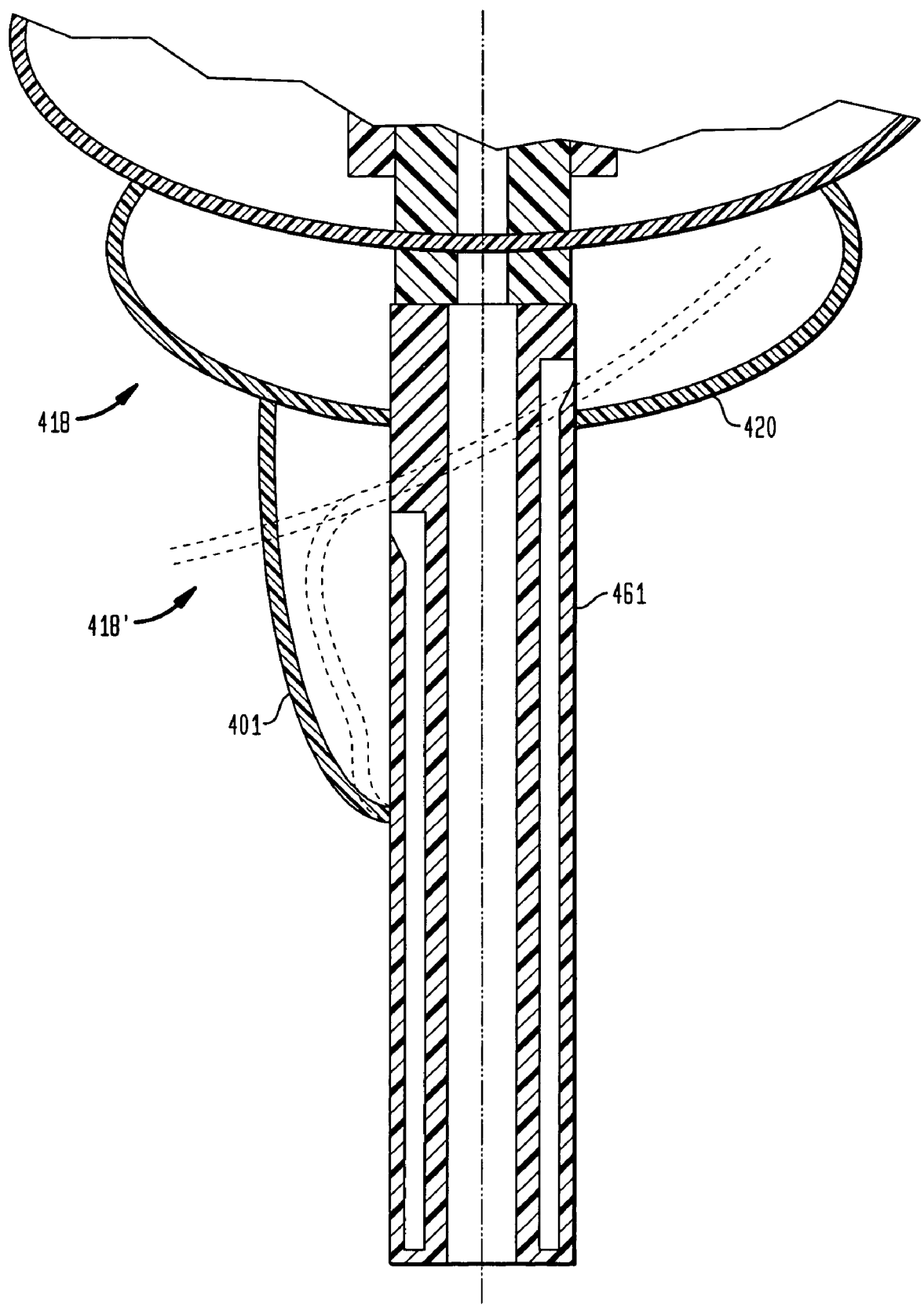
FIGS. 10 and 11 are views similar to FIG. 9, but depicting apparatus according to yet another embodiment of the invention in two operating conditions.

In a further modification, (FIG. 10), an inflatable structure 401 is mechanically connected between catheter section 461 proximal to the ablation device 418 and the ablation device itself as, for example, between the catheter and the proximal wall of reflector balloon 420. Thus, when inflatable structure 401 is deflated, the ablation device may be tilted relative to the catheter, as indicated in broken lines at 418'. However, when the inflatable structure 401 is inflated, as seen in solid lines, the ablation device is brought to the condition depicted in solid lines, as by bending of the catheter adjacent the ablation device. Here again, inflation or deflation of the inflatable structure turns the forward-to-rearward axis of the ablation device relative to the proximal regions of the catheter and also relative to the heart and surrounding structures.

Figure 11:
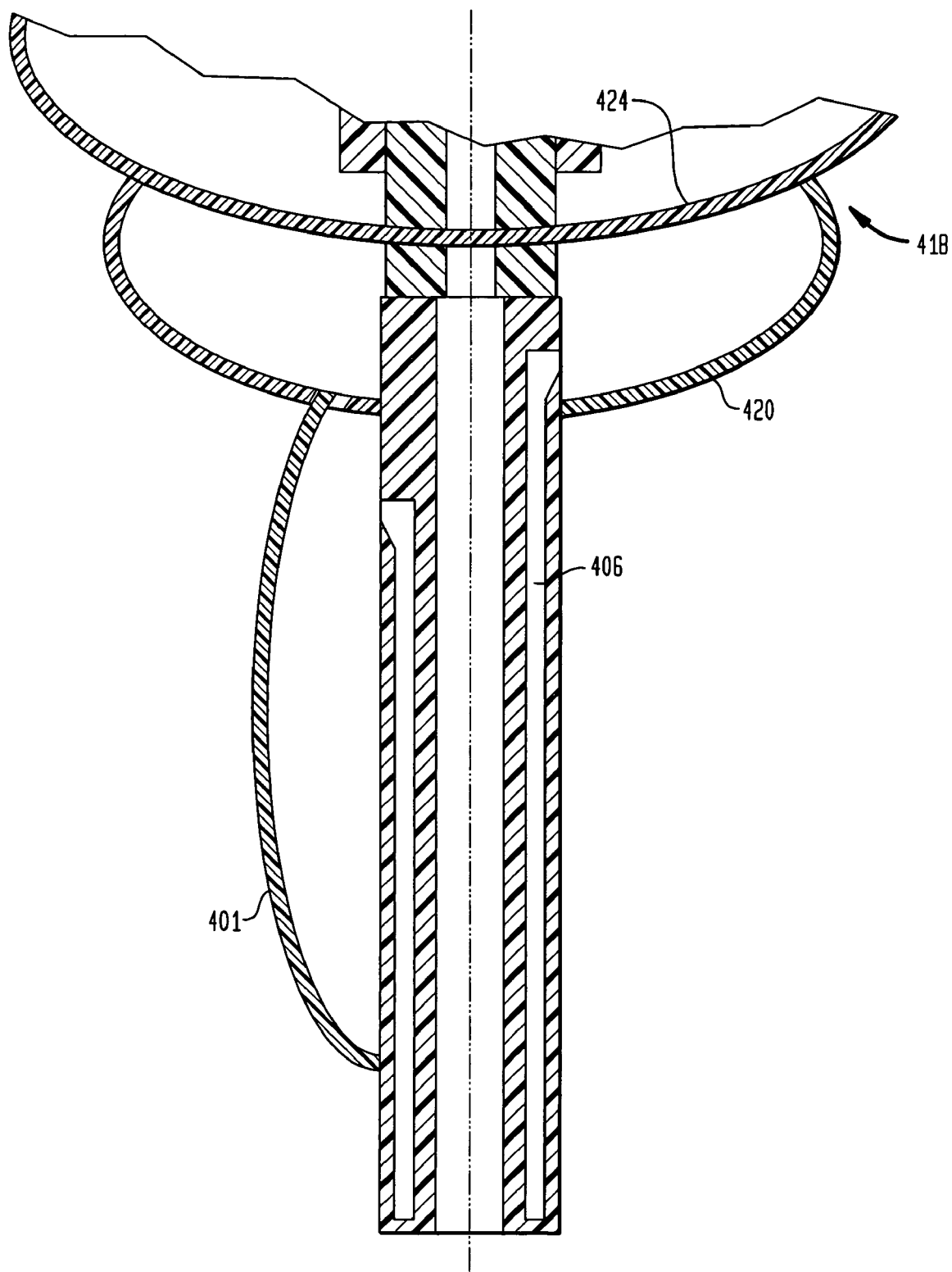

In a further variant (FIG. 11), the interior space within inflatable structure 401 communicates with the interior space of reflector balloon 420. Thus, the degree of inflation of structure 401 and, hence, the disposition of the ablation device, can be controlled by varying the pressure within reflector balloon 420. Thus, the position of the catheter can be varied by varying the gas pressure applied to the reflector balloon inflation lumen 406. In this regard, operation of the ablation device itself does not vary significantly with gas pressure inside reflector balloon 420; provided that the gas pressure within the reflector balloon is sufficient to move the wall of reflector balloon 420 away from the common wall or active interface 424 separating the reflector balloon and the structural balloon, the active interface will provide the desired ultrasonic reflective interface.

In a further variant, inflatable structure 401 may have a wall structure different from the wall of the reflector balloon, so that the inflatable structure will only inflate to a substantial degree after the gas pressure inside reflector balloon reaches a certain threshold value.

In yet another variant, the inflatable structure 401 may be formed as an extension of the reflector balloon along one side of the catheter.

Figure 9:
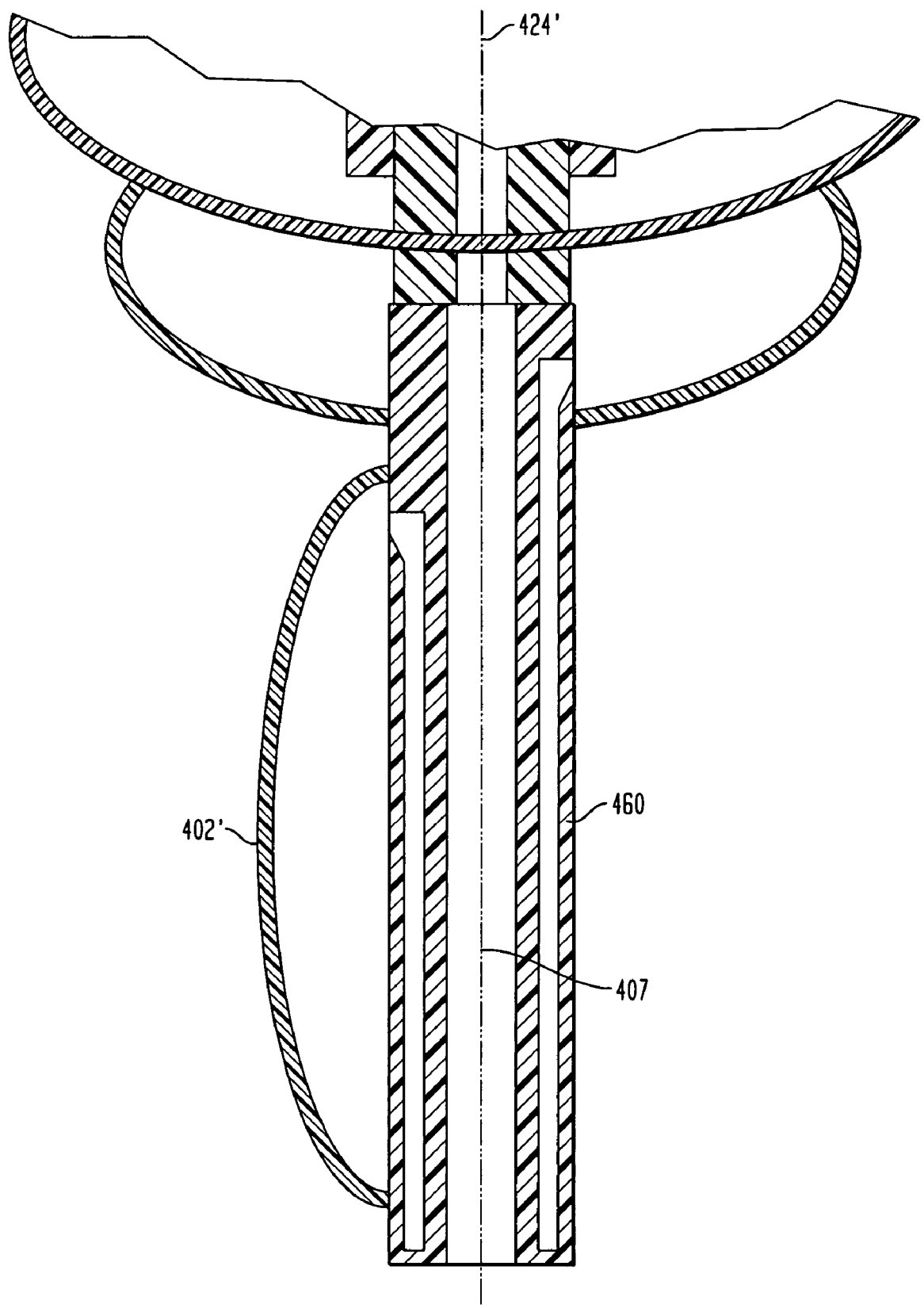
FIG. 9 is a view similar to FIG. 8 depicting the apparatus of FIG. 8 in another operating condition.
Figure 12:
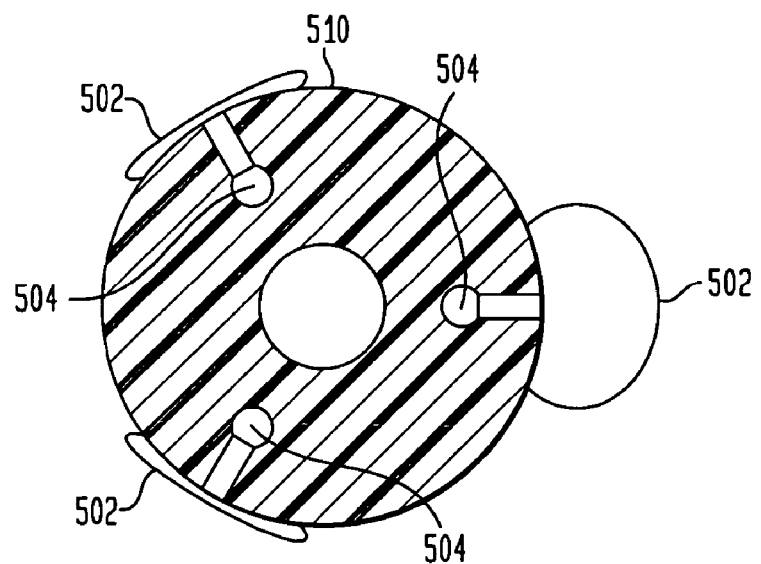
FIG. 12 is a diagrammatic sectional view depicting a portion of apparatus according to yet another embodiment of the invention.

In a further variant, seen in sectional view facing axially along the catheter at FIG. 12, plural inflatable structures 502 are provided around the circumference of the catheter 560, and the separate inflatable structures are provided with separate inflation lumens 504. This allows selective bending in multiple directions by controlling the gas pressures within the various inflation structures. Here again, each of these structures may bear on the proximal side of the ablation device, which may be configured as shown in FIGS. 8 and 9, so that each structure extends only along the bendable portion of the catheter.

Figure 13:
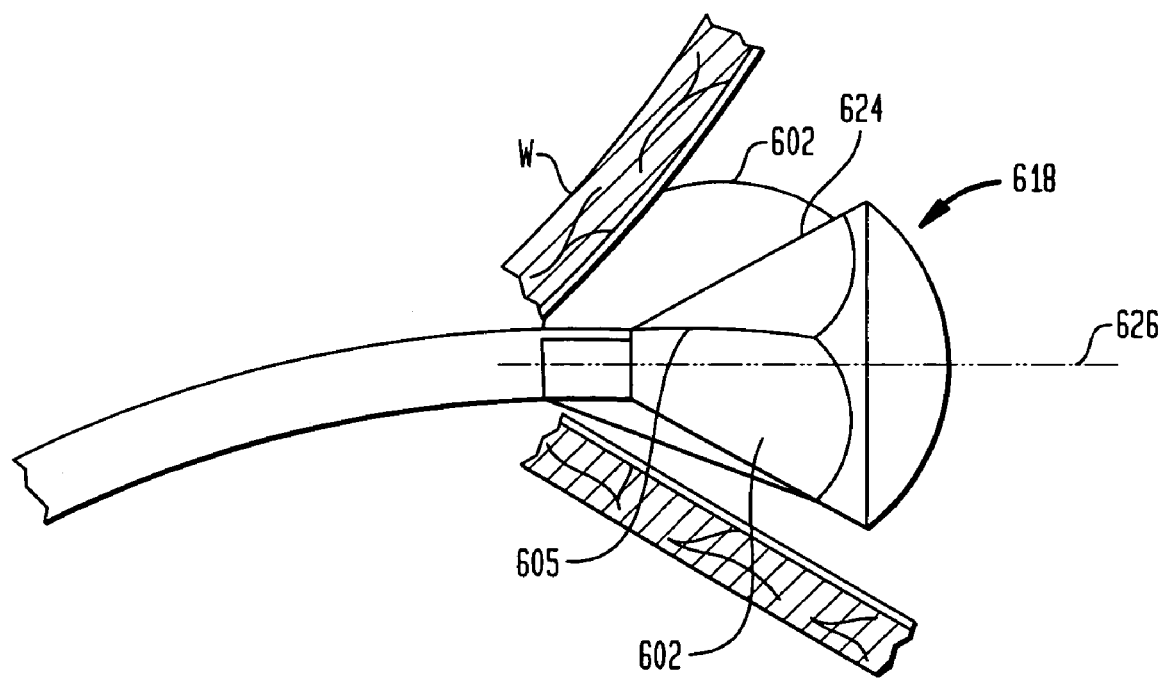
FIG. 13 is a fragmentary elevational view depicting apparatus according to a still further embodiment of the invention.

In yet another variant (FIG. 13), a plurality of inflatable structures 602 are provided around the circumference of the catheter and, hence, spaced around the axis 626 of the ablation device 618. These inflatable structures are arranged so that they bear on the heart wall W or other anatomical structure when inflated and, thus, move the ablation device 618 relative to the heart. Each inflatable structure 602 is independently inflatable or deflatable as, for example, by a separate inflation lumen (not shown) extending to the proximal end of the catheter.

Inflatable structures 602 optionally may serve as reflector balloons of the ablation device. Thus, two or more such structures cooperatively surround axis 626 at the proximal side of the structural balloon, and each such inflatable structure defines a common wall with the structural balloon. Separating walls 605 segregate the individual inflatable structures 602 from one another. Provided that all of the inflatable structures are inflated with a minimal gas pressure sufficient to provide gas at this common wall or interface 624, the structure will provide substantially the same ultrasonic reflecting action as the single reflector balloon discussed above. To the extent that any non-reflective regions at the separating walls 605 cause gaps in the ablation, this can be overcome by rotating the catheter so as to rotate the ablation device about axis 626 and repeating the ultrasonic application step. Alternatively, one or more of the inflatable structures 602 may be left entirely deflated, or may be inflated with a liquid, so as to render a portion of the interfacial wall 624 non-reflective to ultrasound. In this case, the emitted ultrasound is focused only on an arcuate portion of the ring-like focal region. This can be used, for example, where the anatomical structure of the patient makes it undesirable to ablate the entire ring.

Figure 20:
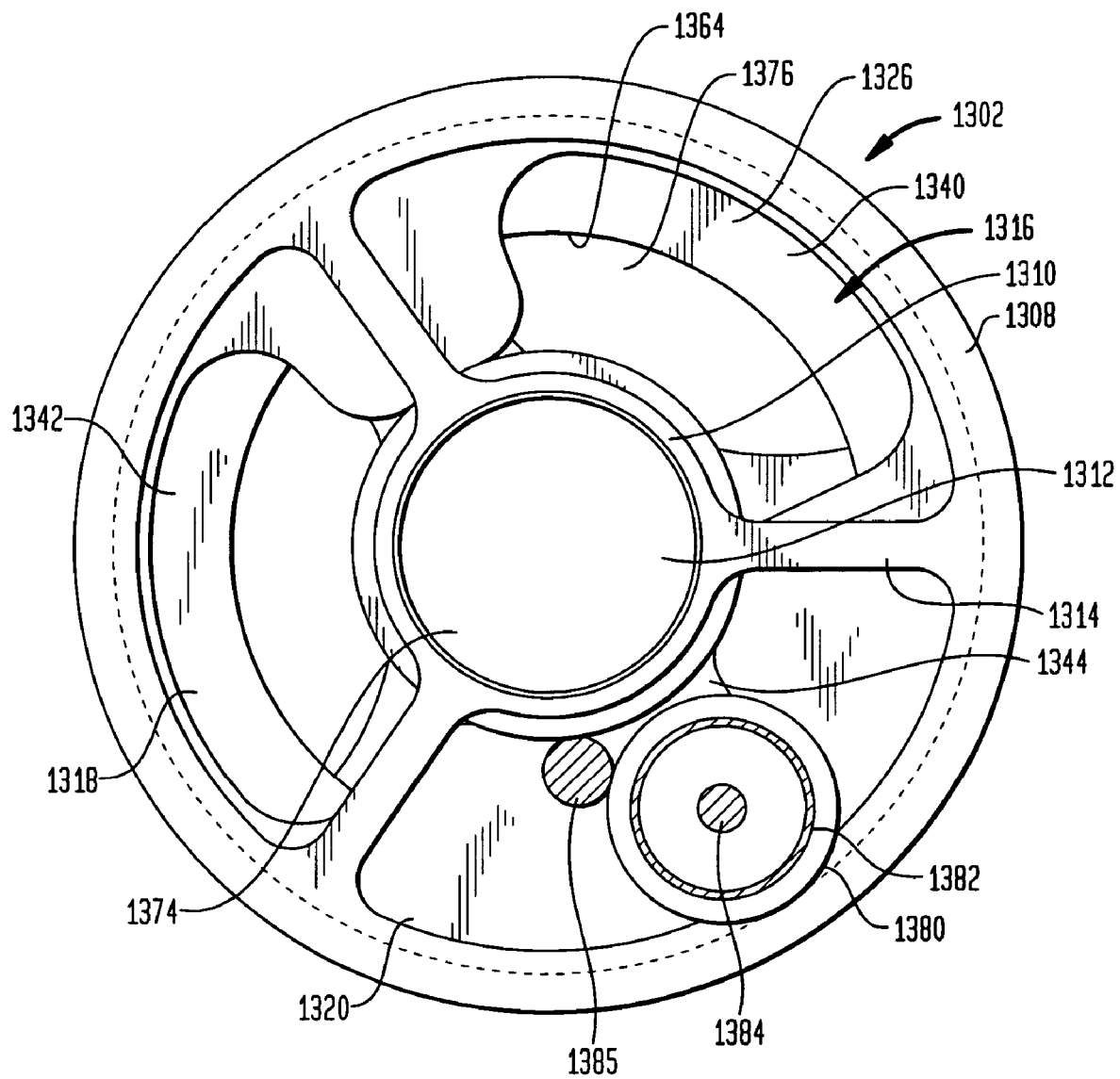
FIG. 20 is a sectional view taking along line 20-20 in FIG. 14.

Apparatus according to a further embodiment includes a catheter 1302 (FIG. 14) having a proximal end 1301, a distal end 1303, and an expansible structure including a reflector balloon 1304 and a structural balloon 1306 similar to those discussed above with reference to FIG. 1 attached to the distal end of the catheter. As seen in FIG. 20, catheter 1302, at least at its distal end, includes a circular outer wall 1308, a central tubular wall 1310 defining a principal or central lumen 1312 and a set of webs 1314 extending between the tubular wall 1310 and the other wall so that the tubular wall, outer wall, and webs cooperatively define a first additional lumen 1316, a second additional lumen 1318, and a third additional lumen 1320 disposed in the periphery of the catheter, around the central lumen. A reinforcing structure 1321 including an emitter assembly 1322 and an extensible structure 1392 (FIG. 14) is mounted to the distal end of the catheter. Emitter assembly 1322 includes a proximal mounting structure 1324, a hollow, tubular piezoelectric element 1326, and a distal mounting structure 1328. These features are shown on a greatly enlarged scale in the drawings; in actual practice, the catheter 1302 typically has an outside diameter on the order of 3-4 mm.

Figure 15:
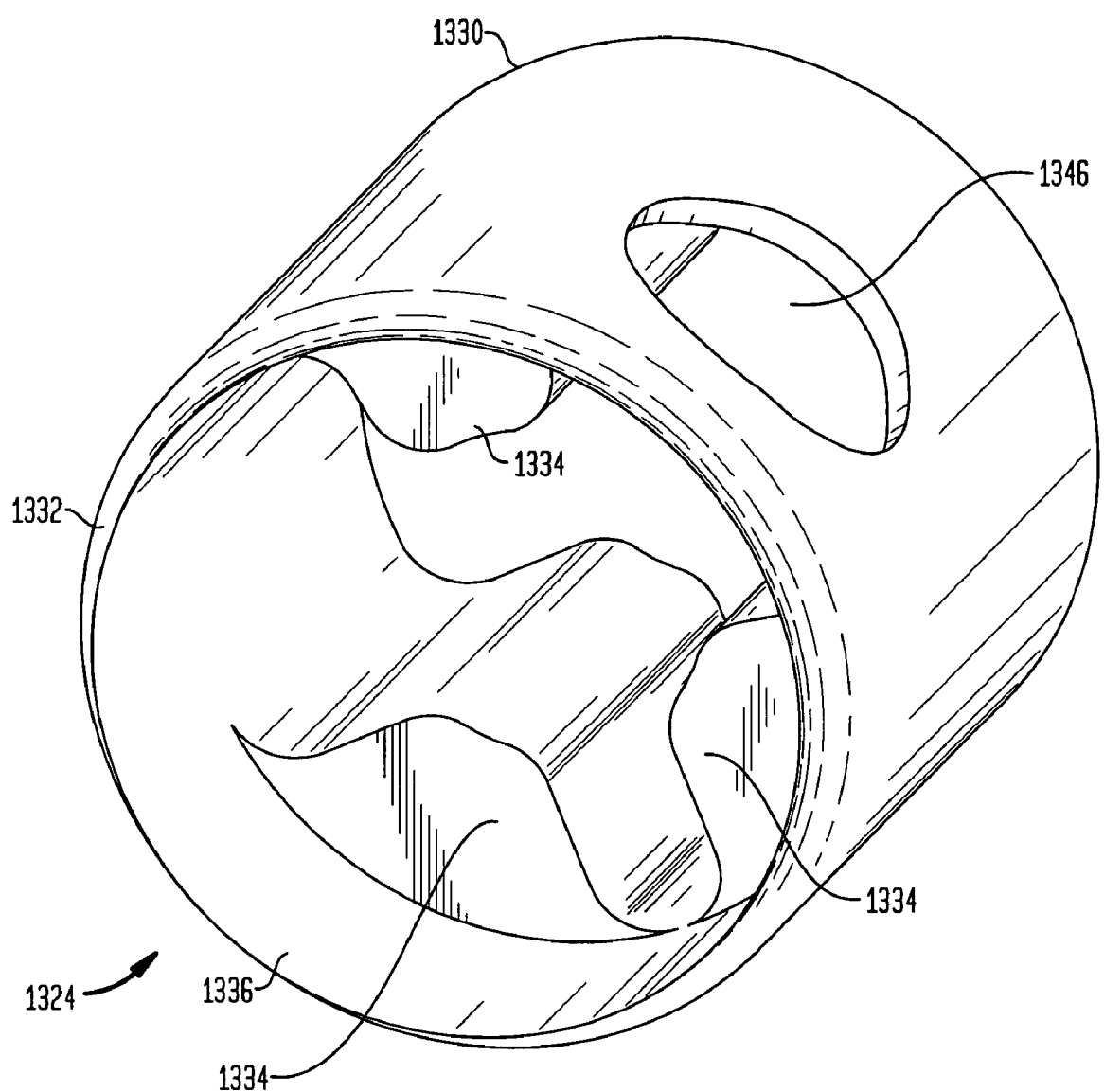
FIGS. 15 and 16 are perspective views depicting a structure used in the embodiment of FIG. 14.
Figure 16:
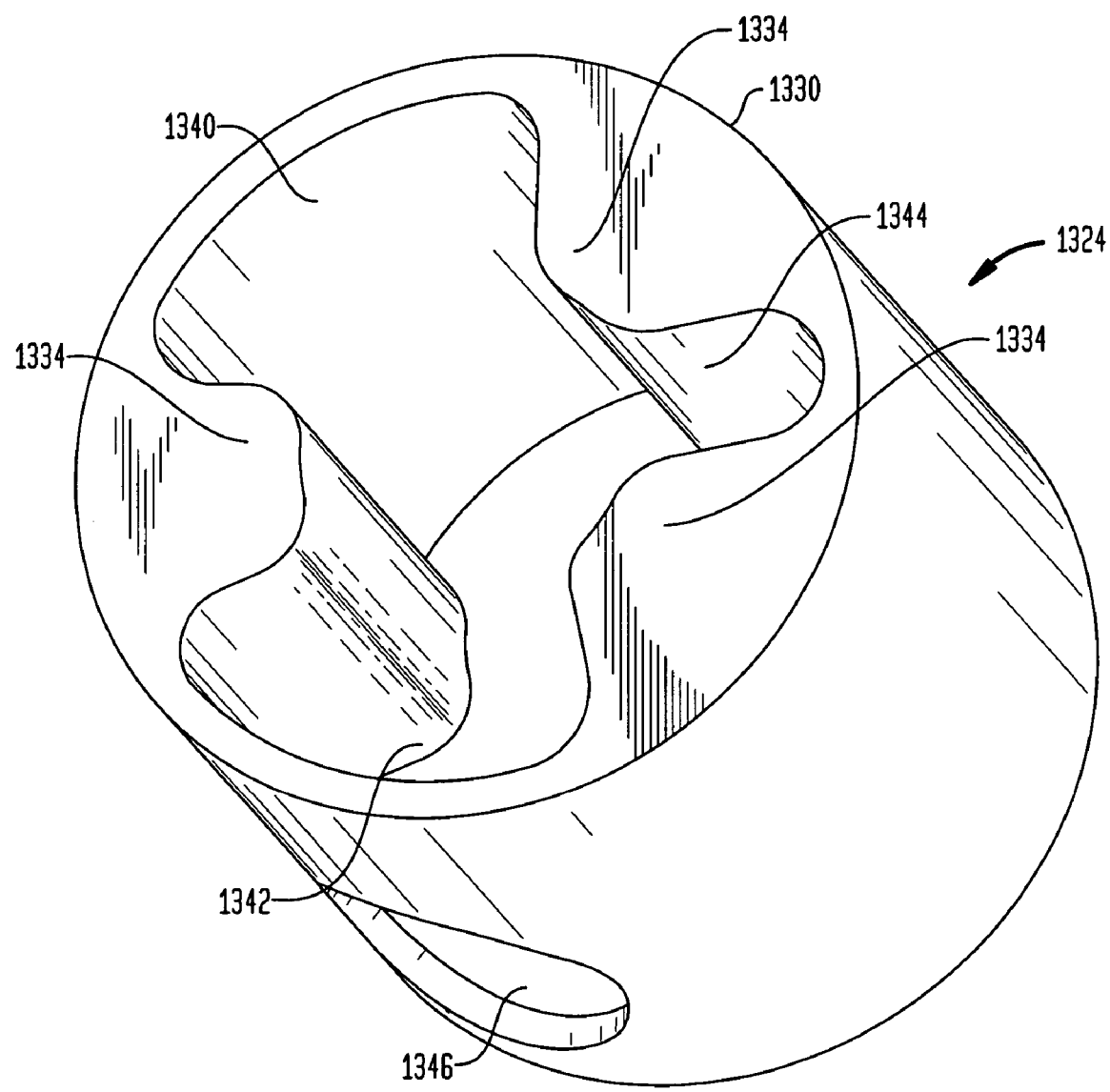

As best seen in FIGS. 15 and 16, the proximal mounting structure 1324 is formed as a generally cylindrical metallic shell having a proximal end 1330 and a distal end 1332. Three thick metallic ribs 1334 extend inwardly from the shell at the proximal end 1330 of the structure. These ribs terminate short of the distal end 1332 so as to leave a pocket 1336 adjacent the distal end of the structure. Ribs 1334 define a first side channel 1340, a second side channel 1342, and a slot 1344. A port 1346 extends through the outer wall of the shell and intersects the second side channel 1342.

Figure 17:
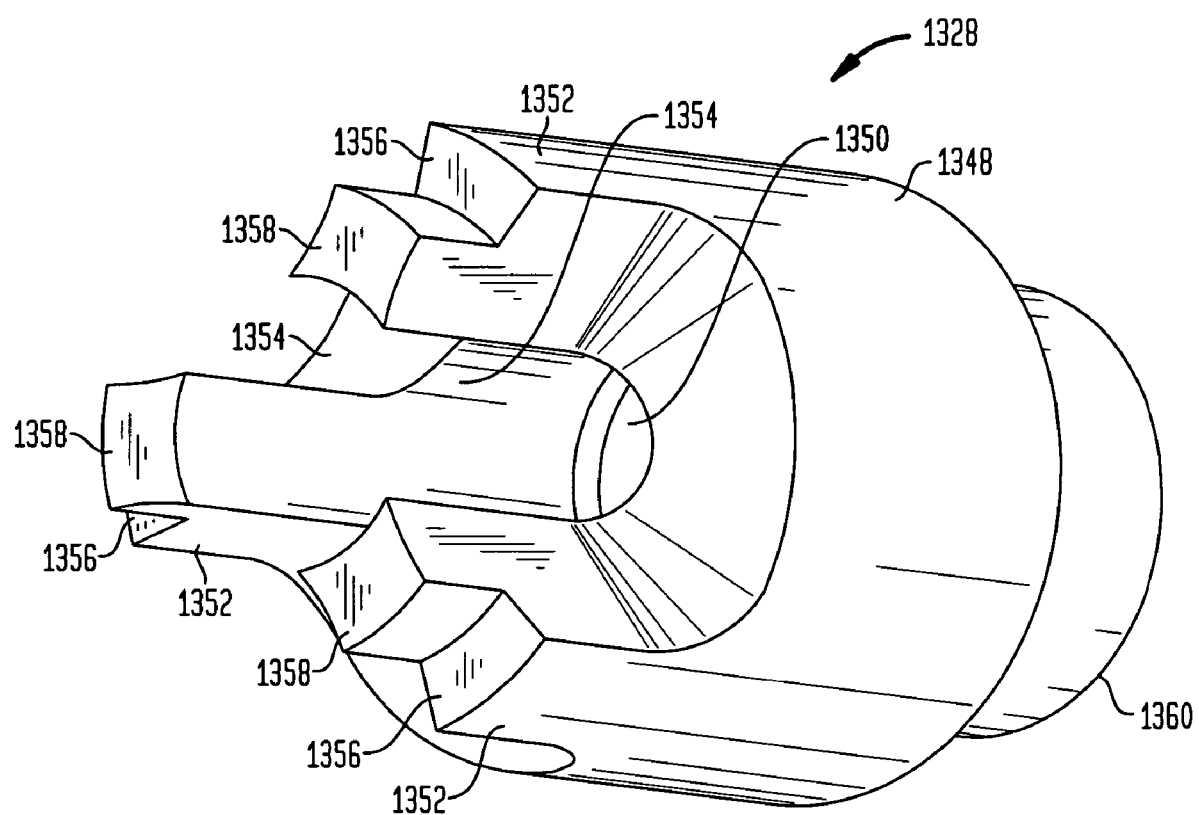
FIGS. 17 and 18 are perspective views depicting another structure used in the embodiment of FIGS. 14-16.

The distal mounting structure 1328 includes a solid cylindrical body 1348 with a central bore 1350 extending through the body and coaxial with the other periphery of the body. Three projections 1352 extend proximally from the body. Projections 1352 are spaced around the periphery of the body and define slots 1354 extending radially inwardly between them. Each projection 1352 has a stop surface 1356 facing in the proximal direction and a contact portion 1358 projecting slightly beyond the stop surface 1356 in the proximal direction (to be left as seen in FIG. 17). A skirt 1360 projects from the distal end of body 1348. Skirt 1360 defines a cylindrical exterior surface coaxial with bore 1350 and a frustoconical interior pocket 1362, also coaxial with bore 1350. Pocket 1362 is slightly narrower at its proximal end (at the juncture with body 1348) then at its open, distal end. Preferably, skirt 1360 tapers outwardly at an included angle of about 11°.

Figure 14:
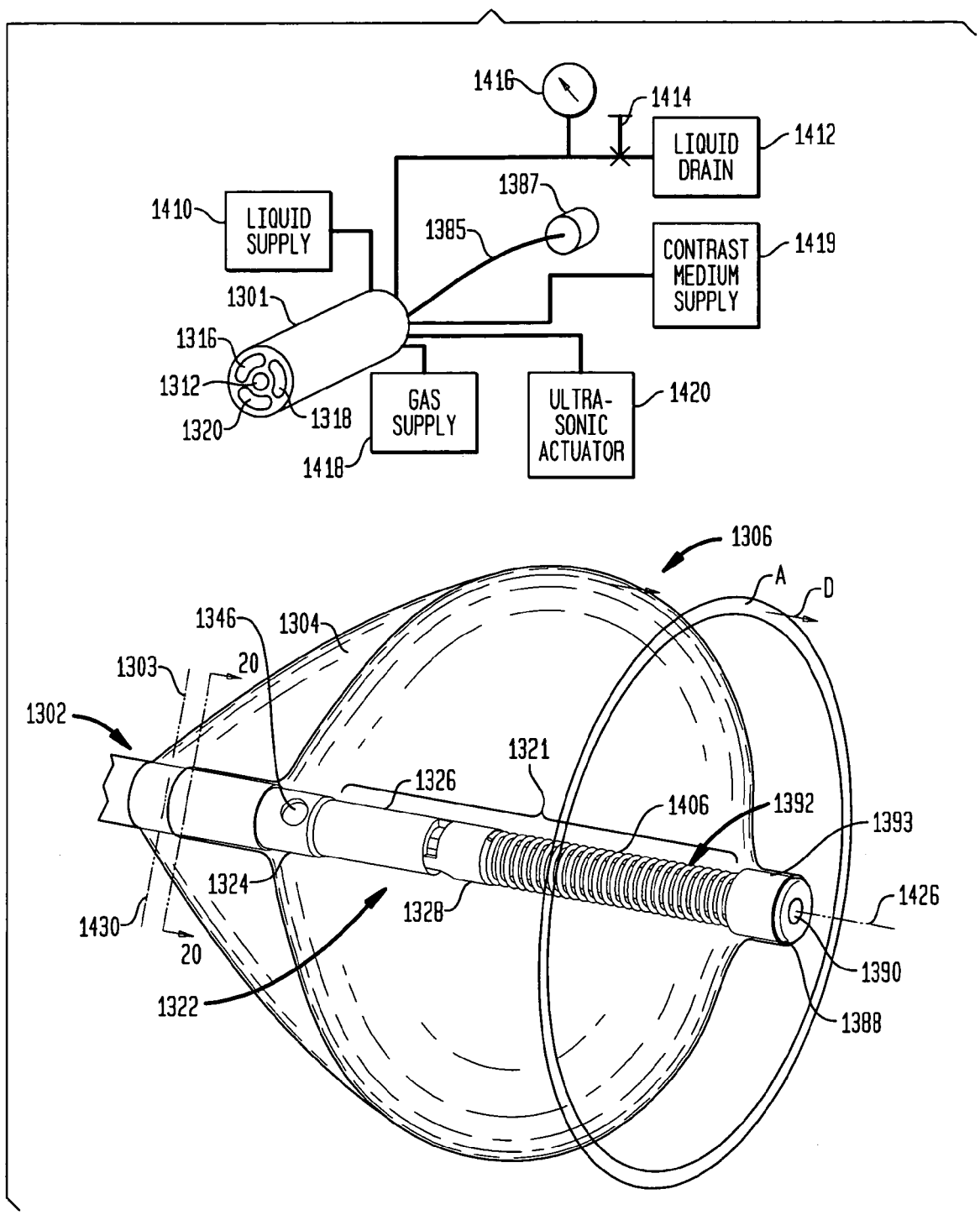
FIG. 14 is a diagrammatic, partially perspective view depicting apparatus according to another embodiment of the invention.
Figure 19:
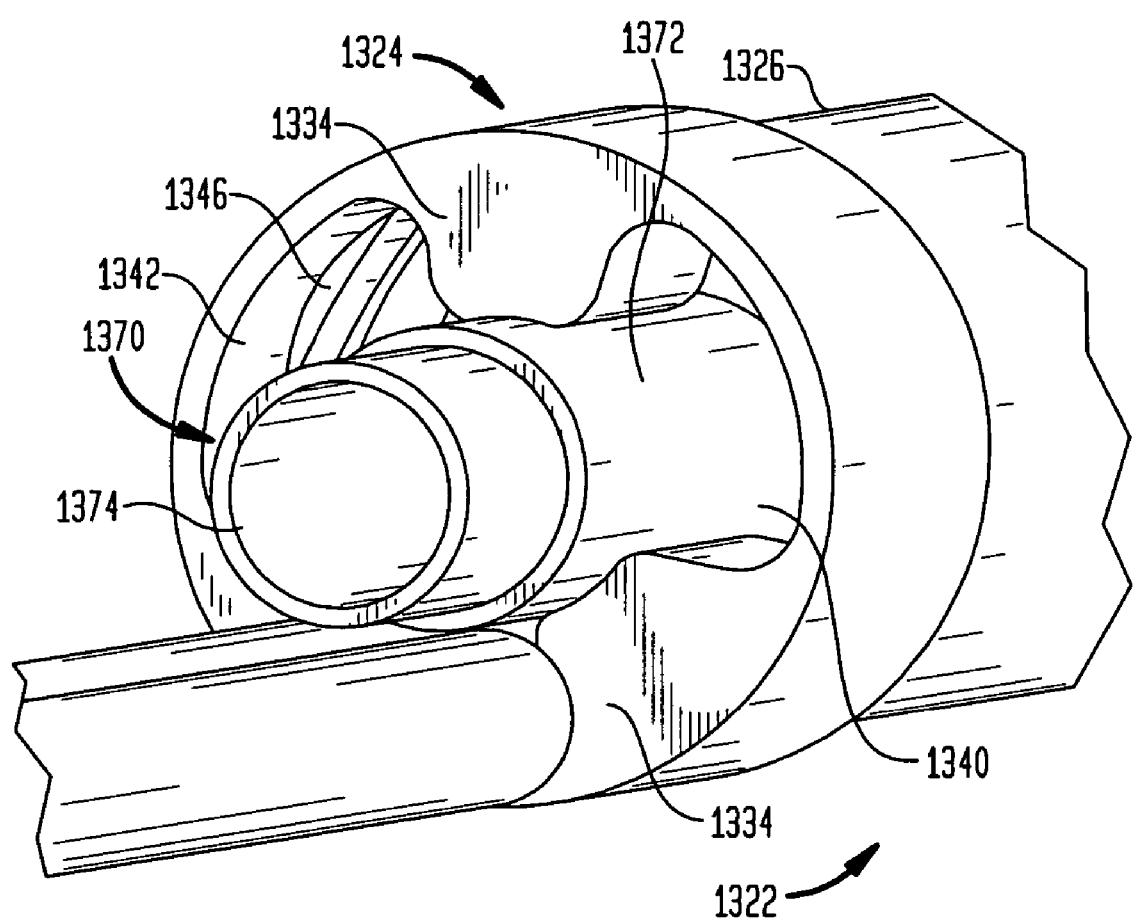
FIG. 19 is a fragmentary perspective view showing a portion of the structure depicted in FIG. 14.
Figure 21:
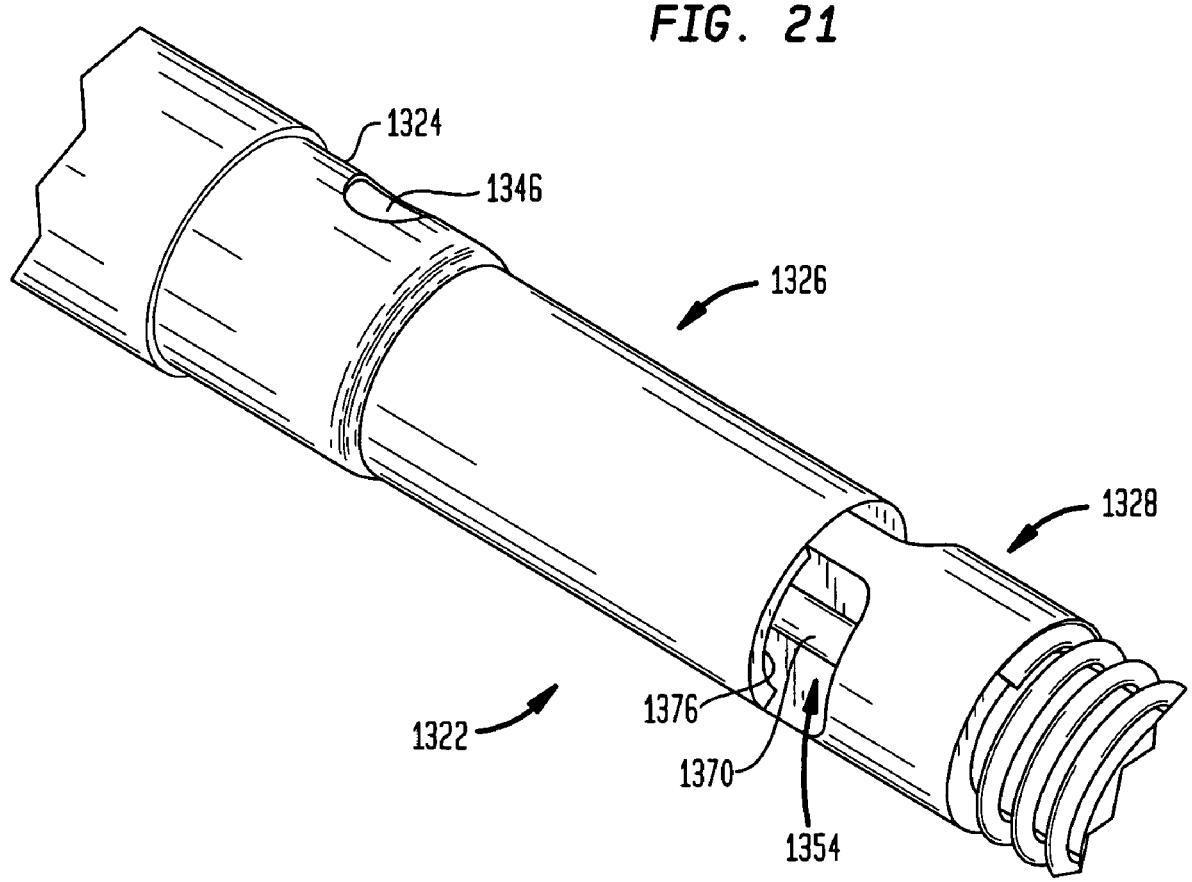
FIG. 21 is a fragmentary perspective view depicting a portion of the structure shown in FIGS. 14-20.

Tubular piezoelectric element 1326 has an exterior surface visible in FIGS. 14, 19, and 21 and an interior surface 1364 (FIG. 20). Electrically conductive metallic coatings (not shown) overlie both the exterior and interior surfaces of piezoelectric element. The piezoelectric element typically is formed from piezoelectric ceramic such as that sold under the commercial designation PZT-8. As best seen in FIGS. 19-21, piezoelectric element 1326 is engaged with the distal end of the proximal mounting structure 1324. The proximal end of the transducer is lodged within the cylindrical pocket 1336 at the distal end of the structure. The piezoelectric element is soldered or otherwise physically and electrically connected to the proximal mounting structure. Distal mounting structure 1328 is secured to the distal end of the piezoelectric element 1326. The distal end of the tubular piezoelectric element abuts the stop surfaces 1356 (FIG. 17) of the distal mounting structure. The contact portions 1358 of the projections on the distal mounting structure extend into the interior of the piezoelectric element. The distal mounting structure is electrically and mechanically bonded to the inside surface of the piezoelectric element as by soldering.

Figure 18:
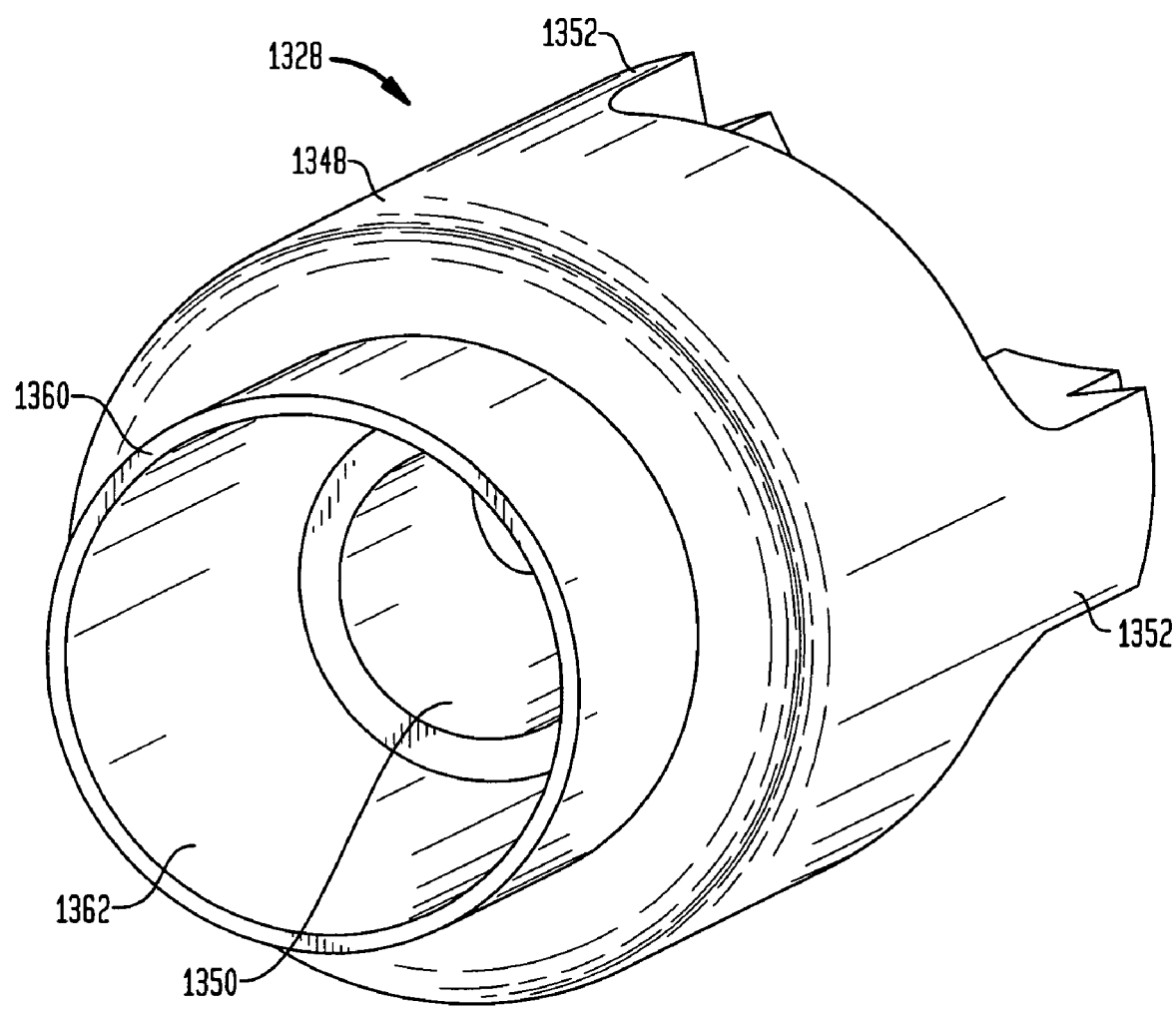

A thin-walled, electrically-conductive and preferably metallic tube 1370, referred to herein as the "inside tube," is supported by the ribs 1334 of the proximal end element, but electrically insulated from the proximal end element by a short hollow insulator 1372 formed from a dielectric material as, for example, a thin coating of polymer on the exterior surface of the inside tube. The inside tube extends through the interior of piezoelectric element 1326. The distal end of inside tube 1370 is engaged in the distal mounting structure 1328 (FIG. 21). The inside tube defines a bore 1374. The bore of the inside tube is aligned with and continuous with the bore 1350 (FIG. 18) of the distal mounting structure. The outside diameter of inside tube 1370 is substantially smaller than the inside diameter of the transducer element 1326. However, the proximal and distal mounting structures maintain tube 1370 substantially coaxial with transducer 1326. The exterior surface of tube 1370 and the interior surface 1364 (FIG. 20) of the transducer 1326 cooperatively define an annular passageway 1376 extending from the proximal end of the piezoelectric element to its distal end. Passageway 1376 communicates, at its proximal end, with the first channel 1326 in the proximal mounting structure and also with the second channel 1318 of the proximal mounting structure. At its distal end, the annular passageway inside piezoelectric transducer 1326 communicates with the slots 1354 in the proximal mounting structure. The entire emitter assembly 1322, including the proximal and distal mounting structures piezoelectric element and inside tube forms a rigidly connected unit.

The rigid transducer assembly 1322 is mounted to the distal end of the catheter 1302 so that the first channel 1340 in the proximal mounting structure (FIG. 16) is aligned with the first additional lumen 1316 of the catheter, whereas the second channel 1342 is aligned with the second additional lumen 1318 of the catheter. Thus, both the first and second additional lumens 1316 and 1318 of the catheter communicate with the annular passageway 1376 inside the piezoelectric element, whereas the second additional lumen 1318 communicates with port 1346 (FIGS. 19 and 15 and 16) through the second side channel 1342 of the proximal mounting structure. Inside tube 1370 is aligned with the principal lumen 1310 of the catheter so that the bore 1374 of the central tube communicates with the principal lumen. Slot 1344 of the proximal mounting structure is aligned with the third additional lumen 1320 of the catheter.

A small coaxial cable 1380 extends through the third additional lumen 1320 of the catheter. This coaxial cable has a first conductor in the form of a sheath 1382 and a central conductor 1384 separated from sheath 1382 by a dielectric jacket. Sheath 1382 is electrically connected to the proximal mounting structure 1324 within slot 1344. The jacket 1382 is electrically connected through the proximal mounting structure 1326 to the outside surface of piezoelectric element 1326. The central conductor 1384 extends into the annular passageway 1376 and is bonded to the inside tube 1370, so that the central conductor 1384 is electrically connected by inside tube 1370 and distal mounting structure 1328 to the inside surface of the piezoelectric element.

A pull wire 1385, most preferably a metallic wire, has a distal end fixed to the emitter assembly 1322 by welding or otherwise fixing the pull wire to the proximal mounting structure 1324. Pull wire 1385 extends through the third additional lumen 1320 to the proximal end 1301 of the catheter and is connected to a handle 1387 so that the physician can selectively pull or push on the pull wire during use. Typically, the handle is integrated with another handle (not shown) attached to the proximal end 1301 of the catheter, so that the physician can manipulate both the catheter and the guide wire. For example, the handle for the catheter may carry a separate knob for other manual control device so that the physician can manipulate the catheter by manipulating the handle and manipulate the guide wire by manipulating the knob or the control device.

The structural balloon 1306 (FIG. 14) is mounted on the catheter so that port 1346 communicates with the interior of this balloon adjacent the proximal end thereof and proximal to transducer 1326. The third additional lumen 1320 of the catheter preferably is isolated from the annular passageway 1376 and from the interior of the structural balloon 1306. For example, any portion of slot 1344, which is not occupied by portions of the coaxial cable 1380 extending through it may be filled with a bonding material such as an adhesive or a solder. Third peripheral lumen 1320 desirably communicates with the interior of reflector balloon 1304 (FIG. 14) through an opening (not shown) in the peripheral wall 1308 of the catheter.

Figure 22:
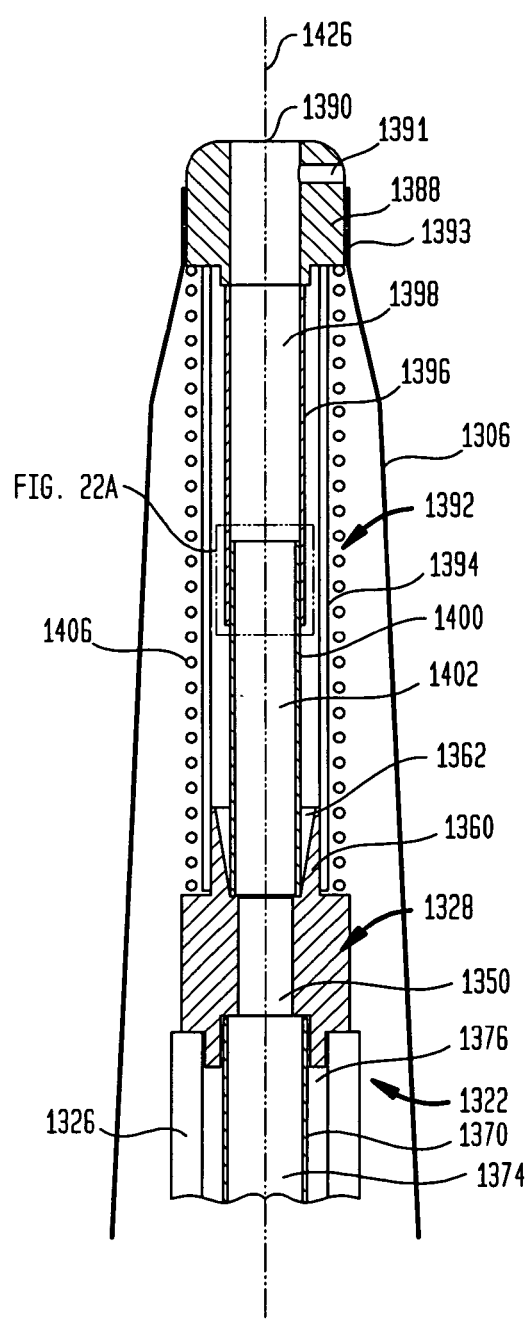
FIG. 22 is a diagrammatic sectional view depicting a portion of the structure shown in FIGS. 14-21 in a collapsed condition.

The structural balloon 1306 has a distal end fitting 1388. An extensible structure 1392 extends between the emitter assembler 1322 and the distal end fitting 1388. As best seen in FIG. 22, the distal end fitting 1388 includes a cylindrical outer surface. Structural balloon 1306 has a hollow cylindrical distal neck 1393, which closely fits over this outer surface and is bonded thereto by an adhesive. End fitting 1388 also includes a through bore extending between its proximal end and its distal end. The distal end of such through bore defining an outlet port opening 1390 just forward of the distal face of the balloon. The distal end fitting further includes one or more transverse bores 1391 (FIG. 22), which extend transverse to the central bore or outlet port opening 1390, and which also communicates with the exterior of the fitting.

Extensible structure 1392 includes a supple, distensible tube 1394 having its distal end connected to the distal end fitting 1388 and having its proximal end connected to emitter assembly 1322. In the arrangement shown, the proximal end of tube 1394 envelops the exterior of skirt 1360 on the distal mounting structure 1328. The extensible structure also includes a first engagement element in the form of a reinforcing tube 1396 fastened to the distal end fitting 1388 and having a bore 1398 communicating with the outlet port opening 1390. The extensible structure 1392 further includes a proximal reinforcing tube 1400. The proximal end tube 1400 is fixed in the seat 1362 of the distal mounting structure 1398. The proximal reinforcing tube, and emitter assembly 1322 cooperatively constitute a second engagement element. As seen in FIG. 22, there is clearance between the outside surface of proximal reinforcing tube 1400 and skirt 1360 adjacent the open distal end of the conical seat 1362. The distal end of proximal reinforcing tube 1400 is telescopically received within the bore 1398 of the distal reinforcing tube 1396.

Figure 22A:
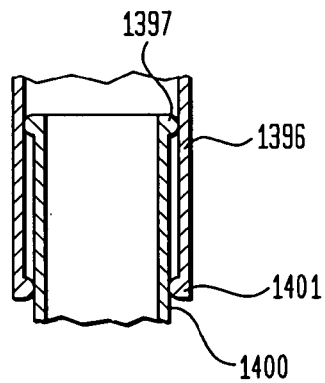
FIG. 22A is a fragmentary view on an enlarged scale of the area indicated in FIG. 22.

As shown in FIG. 22A, the distal end of proximal reinforcing tube 1400 has a small flange 1397 projecting outwardly, whereas the proximal end of distal reinforcing tube 1396 has a small inwardly-directed flange 1401. These features interlock with one another so that the reinforcing tubes cannot be disengaged from one another.

As will be appreciated with reference to FIG. 22, the structure provides a continuous passageway through the outlet port 1390 and the bore of distal end fitting 1380, through the bore 1398 of the distal reinforcing tube, through the bore 1402 of the proximal reinforcing tube and the bore 1350 of distal mounting structure 1350 into the bore 1374 of the inside tube 1370, which in turn communicates with the central, principal lumen 1312 of the catheter. As the principal lumen of the catheter extends to the proximal end of the catheter (FIG. 14), the structure provides a continuous passageway from the proximal end of the catheter through the emitter and balloon structures through the outlet port opening 1390 on the distal side of structural balloon 1306. This continuous passageway is sealed from the interior balloon 1306 and from the annular passageway 1376 inside the piezoelectric element 1326. The distensible tube 1394 blocks any leakage between the telescoping reinforcing tubes 1396 and 1400.

A coil spring 1406 surrounds the reinforcing tubes. The distal end of the coil spring bears on the distal end fitting 1388 and preferably is welded or otherwise securely attached to the distal end fitting 1388. The proximal end of spring 1406 bears on the distal mounting structure 1328 of the emitter assembly 1322. Spring 1406 is also securely attached to the distal mounting structure 1328 of the emitter assembly as by welding the spring to the mounting structure.

In the deflated, collapsed condition depicted in FIG. 22, spring 1406 is in a substantially relaxed condition. The extensible structure 1392 is in an extended state in which the distal ending fitting 1388 and the distal end of balloon 1306 are remote from the emitter assembly 1322. In this condition, also referred to as a disengaged condition, the distal reinforcing tube 1396 remote from the seat 1362 of the emitter assembly 1322. Also, the distal reinforcing tube covers only a small portion of the proximal reinforcing tube 1400. In this condition, the extensible structure 1392 can flex to a significant degree. The reinforcing tubes 1396 and 1394 are thin-walled structures. These tubes desirably have outside diameters on the order of 1-2 mm. Moreover, the tapered seat 1362 does not appreciably restrict flexing of the proximal reinforcing tube 1400. Further, there is a slight clearance between the outside of flange 1397 on proximal tube 1400 and the inside of distal tube 1396, which contributes to flexibility of the assembly. To further increase the flexibility of the assembly, the reinforcing tubes may have openings such as slots or holes in their walls.

In the deflated condition, the structural balloon 1306, as well as the reflector balloon 1304 are in a twisted condition so that they wrap gently around the extensible structure 1392 emitter assembly 1322 and the distal end of the catheter 1302. Thus, all of the structures at the distal end of the catheter form a slender assembly capable of passing through a bore of about 0.187 inches (4.74 mm) inside diameter in a guide sheath or other structure. This assembly is flexible due to the flexibility of the extensible structure. However, the extensible structure, and particularly the telescoped reinforcing tubes are substantially resistant to kinking. The catheter is also flexible. The entire assembly can be advanced and placed into a chamber of the heart, typically the left atrium in the manner discussed above. A guide wire (not shown) may be placed through the aforementioned continuous passageway including the central lumen of the catheter and the bores 1374, 1402, and 1398 of the aforementioned tubes, so that the guide wire extends out through the outlet bore 1390 at the distal end of the assembly.

The catheter and associated elements are used in cooperation with operating apparatus including a liquid supply unit 1410 arranged to supply a cool liquid under pressure and a liquid drain 1412 connected to the second peripheral lumen 1318 of the catheter at its proximal end. The liquid supply 1410, liquid drain 1412, or both desirably are equipped with devices for controlling pressure and flow rate of liquid as, for example, a throttling valve 1414 and a pressure gauge 1416 on the connection between the second lumen and the drain. The operating apparatus further includes a gas supply 1418 connected to the third peripheral lumen 1320, and a source 1419 of a contrast medium arranged for connection to the central lumen 1312. The operating apparatus also includes an ultrasonic actuator 1420 arranged to apply electrical energy at an ultrasonic frequency through the coaxial cable. The catheter has appropriate fittings (not shown) at its proximal end 1301 for making the connections to the operating apparatus. Typically, the catheter is provided as a disposable unit, whereas some or all of the elements of the operating apparatus are provided as a reusable unit.

Prior to insertion into a patient, the catheter and associated elements desirably are tested by actuating the liquid supply 1410 to pass the liquid through the first peripheral lumen and into the structural balloon 1306. Although some of the liquid will pass out of the structure balloon through the second peripheral lumen 1318, there is sufficient resistance to flow provided by the second lumen as well as throttling valve 1414 that the structure balloon fully inflates. As the balloon structure inflates, the structural balloon expands radially and contracts axially, causing the distal end of the balloon and the distal end fitting 1388 to move rearwardly or proximally toward the emitter assembly 1322, thereby compressing spring 1406. Moreover, the balloon untwists, causing the distal end fitting 1388 to rotate relative to the emitter structure 1322 about a central forward to rearward axis 1426. This twists the spring 1406 about axis 1426. Distal reinforcing tube 1396 slides rearwardly or proximally over the proximal reinforcing tube 1400, whereas the extensible tube 1394 collapses axially.

Figure 23:
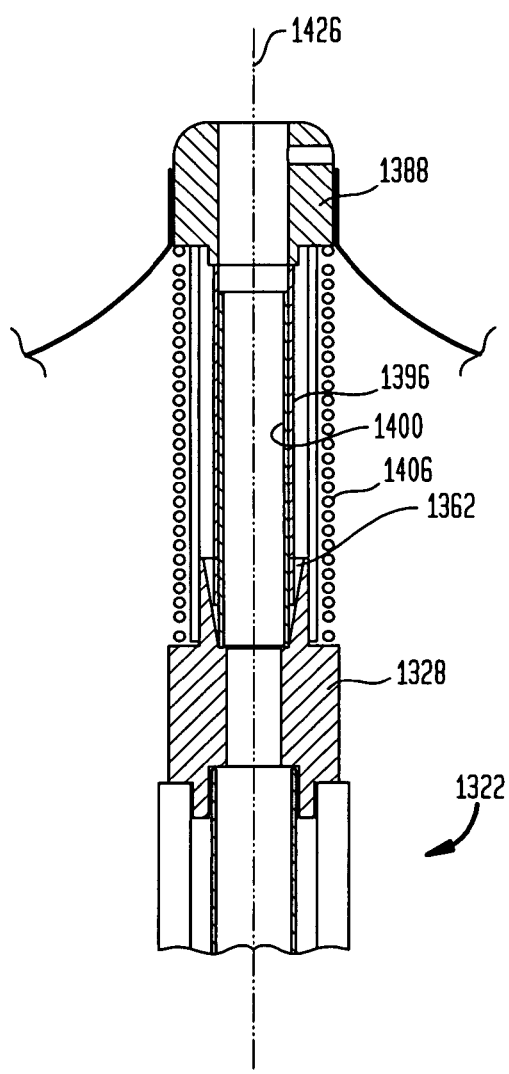
FIG. 23 is a view similar to FIG. 22, but depicting the same portion of the structure in an expanded condition.

In the fully inflated condition (FIG. 23), the reinforcing tubes and associated elements are in an engaged condition. In this engaged condition, distal reinforcing tube 1396 almost entirely encompasses the proximal reinforcing tube 1400. The tubes nested in this manner are quite rigid. The reinforcing tubes span a substantially shorter length in this condition, and structurally reinforce one another over substantially their entire lengths. In the engaged condition, any angular displacement permitted by the mutual clearance between the exterior of the proximal tube and the interior of the distal tube is minimized. Additionally, in the engaged condition, the proximal end of distal reinforcing tube 1396, is firmly engaged in the tapered, conical seat 1362 of the distal mounting structure 1328 on the emitter assembly 1322. This locks the telescoped tubes firmly in position relative to the emitter assembly. In this condition, the reinforcing structure 1321 including the extensible structure 1392 and emitter assembly 1322 is substantially rigid. This rigid structure 1321 is connected to the forward or distal end of the expansible balloon structure by a distal end fitting 1388 and is also connected to the expansible balloon structure adjacent the proximal end of the structural balloon 1306 (FIG. 14) and the adjacent regions of the catheter 1302. In this engaged condition, the distal or forward end of the expansible structure is rigidly held relative to the proximal end of the expansible balloon structure and relative to the emitter assembly.

The flowing liquid passes from the first peripheral lumen through the first channel 1340 of the proximal mounting structure and into the annular passageway 1376 inside the piezoelectric element. The fluid passes from passageway 1376 through the slots 1354 in the distal mounting structure 1328 into the interior of the structure balloon 1306. The fluid circulates through the interior of the structural balloon and passes out of the structural balloon port 1346, a second channel 1342 of the proximal mounting structure 1324 and the second peripheral lumen 1318. This process is continued for a sufficient time to sweep out air or other gases inside the structural balloon. Gas supply 1418 desirably is actuated to inflate reflector balloon 1304 with a gas.

While the balloon structure is in its inflated condition, the ultrasonic actuator 1420 is operated to supply electrical energy to ultrasonic element 1326 by way of the coaxial cable 1380 (FIGS. 19 and 20). This allows a final test of the electrical connections and piezoelectric element. The ultrasonic actuator 1420 should supply the electrical energy at a frequency precisely matched to the resonant of frequency of the piezoelectric element 1326. Different piezoelectric elements incorporated carried by different catheters will have slightly different resonant frequencies. The resonant frequency of the piezoelectric element 1326 may also vary depending upon the loading applied to it by the balloon structure, including the liquid within the structural balloon, as well as loading applied by structures external to the balloon structure. Preferably, the ultrasonic actuator 1420 includes a circuit (not shown) for monitoring electrical power reflected back from the ultrasonic actuator, as well as a frequency adjusting circuit, which is desirably arranged to vary the frequency of the applied electrical energy until the ratio of reflected power to apply the power is at a minimum. The frequency-varying circuit may operate automatically in response to a measure of the measured reflected power and a measure of the applied power. Alternatively, the frequency-varying circuit can be manually controlled in response to the same parameters. To simulate the loading that will be applied during use, the balloon structure desirably is immersed in a bath of an aqueous liquid during test operation. Thus, during test operation the actuator 1420 is adjusted to a frequency that closely matches the actual resonant frequency of piezoelectric element 1326 during use. After testing, the balloon structure is returned to its deflated condition. Any residual spaces inside the structural balloon are completely filled by substantially gas-free liquid.

After testing, the distal end of the catheter is advanced through the patient's vascular system, with the balloon structure in the collapsed or deflated condition, so as to position the ablation device within a chamber of the patient's heart. The flexibility of the device in the deflated condition, and the relatively small diameter of the device, facilitates this process. A guide wire (not shown) can be inserted through the continuous passageway and through the distal outlet port 1390 during this process. The guide wire may be removed after ablation device is advanced into the heart chamber.

Once the catheter is located in the heart chamber, the balloon structure is brought to its inflated condition by operating the liquid supply and liquid drain as discussed above to inflate the structural balloon 1306 and actuating the gas supply 1418 to inflate the reflector balloon 1304. As discussed above, the interface between the liquid-filled structure balloon 1306 and gas-filled reflector balloon 1304 is configured so as to focus ultrasonic waves emitted from piezoelectric element 1326 into an annular or ring-like ablation region A (FIG. 14) coaxial with the central axis 1426. That is, the interface directs the ultrasonic waves so that the energy converges into this ablation region. Stated another way, the ultrasonic intensity or (the power applied per unit area onto a plane perpendicular to the direction of propagation of the energy) is at a local maximum within the ablation region A. Thus, if one were to measure the energy intensity at various points along the direction of propagation D of the ultrasonic waves in the vicinity of the ablation region, such intensity would increase in the direction of propagation D of the energy inside structural balloon 1306 and over the distance, if any, from the structural balloon to the ablation region. The intensity would reach a local maximum within the ablation region A, and would progressively decrease with further travel in direction D away from the balloon assembly. At any point around the circumference of the ring-like focal region, the direction of propagation D has a component in the forward direction, parallel to axis 1426.

To provide proper focusing action, it is important to maintain the ultrasonic emitter assembly 1322 and particularly the piezoelectric element 1326 concentric with the structural balloon and particularly with the interface with the structural balloon and the reflector balloon. The rigid reinforcing structure 1321 serves to maintain such concentricity. The ring-like ablation region A is thus maintained in a well-defined, substantially unchanging spatial relationship with the ultrasonic emitter assembly 1322 and other components of the reinforcing structure and with the central axis 1426.

By manipulating the pull wire 1385 and the catheter, the physician can position the ablation device, including the balloons and ultrasonic emitter in a desired position relative to the heart chamber. The physician can cause the rigid reinforcing structure, including the emitter assembly 1322 and extensible element 1392 to turn and thus swing axis 1426. This turning motion is accompanied by bending of those portions of catheter 1302 near the distal end of the catheter. Because the pull wire is connected to the rigid reinforcing structure itself, at a point inside of the expansible balloon structure, the balloon structure and the reinforcing structure tend to pivot about a pivot axis schematically indicated at 1430 (FIG. 14) close to the proximal end of the expansible structure or actually inside of the expansible structure. This facilitates positioning of the expansible structure. Only a relatively limited length, from the pivot axis to the forward or distal end of the expansible structure (at distal end fitting 1388) needs to swing inside the limited space within the heart chamber. By contrast, in an otherwise comparable device where the pull wire is affixed to catheter proximal to the expansible structure, the expansible structure will tend to swing about a pivot axis further to the rear and hence further from the distal end of the expansible structure.

Also, because the pull wire is attached to the emitter assembly, it provides an additional safety feature. In the event of a structural failure in the catheter or balloons, the emitter assembly and those portions of the catheter and balloons remaining attached to the emitter assembly can be retrieved from within the patient's heart by pulling the pull wire or, in the alternative, can be kept in place by holding the pull wire until the same can be surgically removed in an emergency open-heart procedure. Further, the distal end fitting 1388 is connected to the emitter assembly by the welded spring 1406 and by the interlocked flanges 1397 and 1401 on the reinforcing tubes 1396 and 1400 (FIG. 22A). Thus, despite the failure of any other structural elements, distal end fitting 1388 remains securely attached to the pull wire by the welded spring 1392 and the bonded components of the emitter assembly 1322.

In the manner discussed above, the physician can rotate the catheter and thus rotate the expansible structure and the pivot axis 1430 about the central axis 1426. Therefore, by adjusting the pull wire and rotating the catheter, the physician can bring the expansible structure and the central axis to essentially any desired orientation and location within the heart. Here again, the position of the expansible structure can be monitored by the physician using a contrast medium injected from contrast medium supply 1419 (FIG. 14). To form a lesion in the form of a complete loop or a substantial portion of a loop, the physician will bring the apparatus to an orientation similar to that shown in FIG. 1, referred to herein as a "normal" disposition. In this normal distribution, at least a substantial portion of the ring-like ablation region A is disposed within or in close proximity to the wall of the heart. The orientation of the axis 1426 and ablation region A are depicted schematically in FIG. 24. In the normal disposition, the plane of the ablation region A is substantially parallel to a plane P defined by that portion of the heart wall lying closest to the ablation region. Thus, most or all of the ablation region A lies within or close to the heart wall. The physician can operate the ultrasonic actuator 1420 (FIG. 14) so as to excite the piezoelectric element and cause the device to emit ultrasonic waves and ablate a loop-like lesion L in the heart wall, encompassing all or a substantial portion of a loop extending around the axis 1426. As mentioned above, such a loop-like lesion can be formed around the ostium OS of a pulmonary vein or around another anatomical structure.

Figure 24:
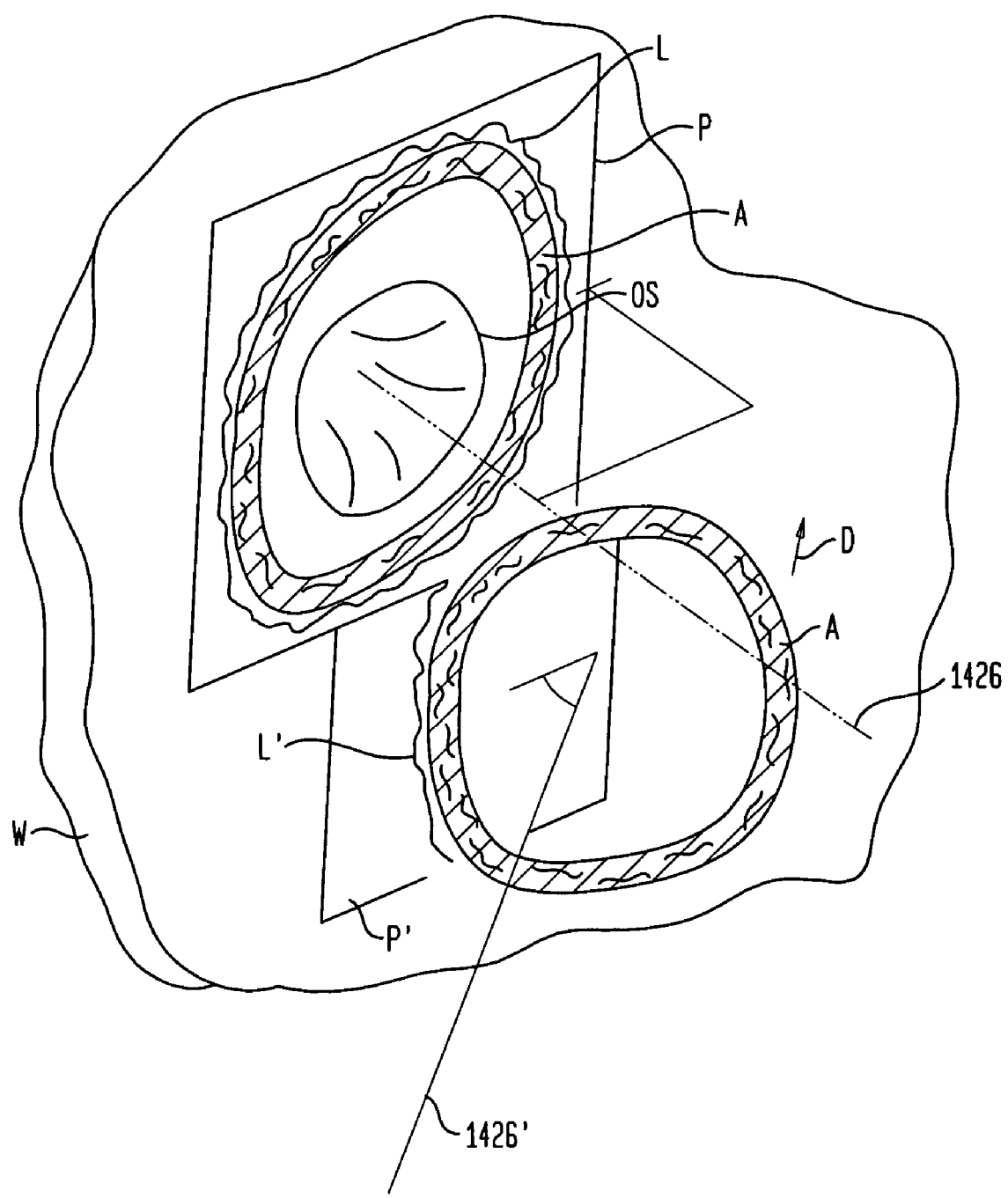
FIG. 24 is a schematic view depicting certain geometrical relationships between the structures of FIGS. 14-23 and a portion of the heart wall during a method in accordance with one embodiment of the invention.

Alternatively or additionally, the physician may bring the ablation device to a canted disposition, also schematically depicted in FIG. 24. In the canted disposition, the plane of the ring-like ablation region is not parallel to a theoretical plane P', defined by that portion of the heart wall tissue closest to the ablation region. In such canted disposition, the axis 1426 of the ablation device is not perpendicular to the theoretical plane, but instead lies at another angle, to this theoretical plane, most typically an oblique angle. In this canted disposition, ablation region A' is close to or within the heart wall over only a small portion of the circumference of the ablation region. If the physician actuates the ultrasonic actuation source and causes the ablation device to emit ultrasonic waves while the device is in this canted disposition, ultrasonic waves will again be focused in the entirety of the ablation or focal region A. However, ablation will occur only where the ablation or focal region A is within or in close proximity to the heart wall. Thus, a lesion L' will be formed only along a relatively small arcuate region approximating a straight line.

The energy directed into other portions of the ablation region A', which lie remote from the heart wall, will pass forwardly, in propagation directions D. The stray ultrasonic waves will pass into the blood within the heart. However, the intensity of the ultrasonic waves diminishes rapidly with distance in the propagation direction, beyond the ablation focal region A'. Moreover, the ultrasonic absorptivity of blood is relatively low, and the blood within the heart is typically moving and is thermally conductive. Therefore, the ultrasonic waves passing into the blood typically will not heat the blood to a degree sufficient to cause coagulation. Some of the ultrasonic waves passing in the forward direction, beyond the ablation region A, may impinge on portions of the heart wall remote from the ablation region. However, because the ultrasonic intensity diminishes with distance in the forward direction, those portions of the heart wall remote from the ablation region A' typically will not be heated to a degree sufficient to cause unintended ablation of those regions.

During the course of a treatment, the physician can use the normal and canted dispositions as desired, and in any order. Because the disposition of the ablation device is established without reliance on engagement between the device and the pulmonary vein ostium or other anatomical structures, the loop-like and linear lesions can be placed where desired. It has been proposed that atrial fibrillation can be treated successfully by forming lesions surrounding the ostia of the pulmonary veins in combination with linear lesions. Such a combination of lesions can be achieved by use of the canted and normal dispositions. Preferably, the ablation device is moved between dispositions while the expanded structure remains in its expanded condition. Thus, where the expansible structure includes balloons, as discussed above, the balloons remain inflated while the device is maneuvered. Once again, the ability to inject contrast medium while the balloons remain in their inflated condition, and without using a separate catheter for such introduction, is advantageous.

When the piezoelectric element is actuated to emit ultrasonic waves, it will also generate heat. Preferably, the liquid supply 1410 (FIG. 1) and liquid drain 1412 are operated to continually circulate the aqueous liquid through the ablation device. As mentioned above in connection with the initial inflation of the structural balloon, the aqueous liquid passes from the supply 1410 through first side lumen 1316 of the catheter, through the first channel 1340 of the proximal mounting structure and into the annular channel 1376 (FIGS. 20 and 21) within the piezoelectric element 1326. The fluid passing within the piezoelectric element passes through the channels 1354 of the distal mounting element, into the structural balloon 1306 and ultimately passes out of the structural balloon through port 1346 (FIG. 21), second channel 1342 of the proximal mounting structure and the second peripheral lumen 1318 of the catheter, whereupon it passes to the drain. This circulation is achieved without need for a separate catheter for liquid circulation and without occupying the central lumen of the catheter with the circulating liquid. The circulating liquid effectively removes heat from the piezoelectric element.

As mentioned above, both the first channel 1340 and the second channel 1342 communicate with the annular channel 1376 inside the piezoelectric element. Therefore, some portion of the circulating liquid may pass from the proximal end of the annular channel back into the second channel 1342 and to the drain, without passing through the entire annular channel. However, this effect is minimal. In a variant, a blocking wall (not shown) can be provided so as to close the second channel distal to port 1346. Such a blocking wall may be formed integrally with the proximal mounting structure 1324, as a part of the piezoelectric element or as a separate element inserted between the piezoelectric element and the proximal mounting structure.

Figure 25:
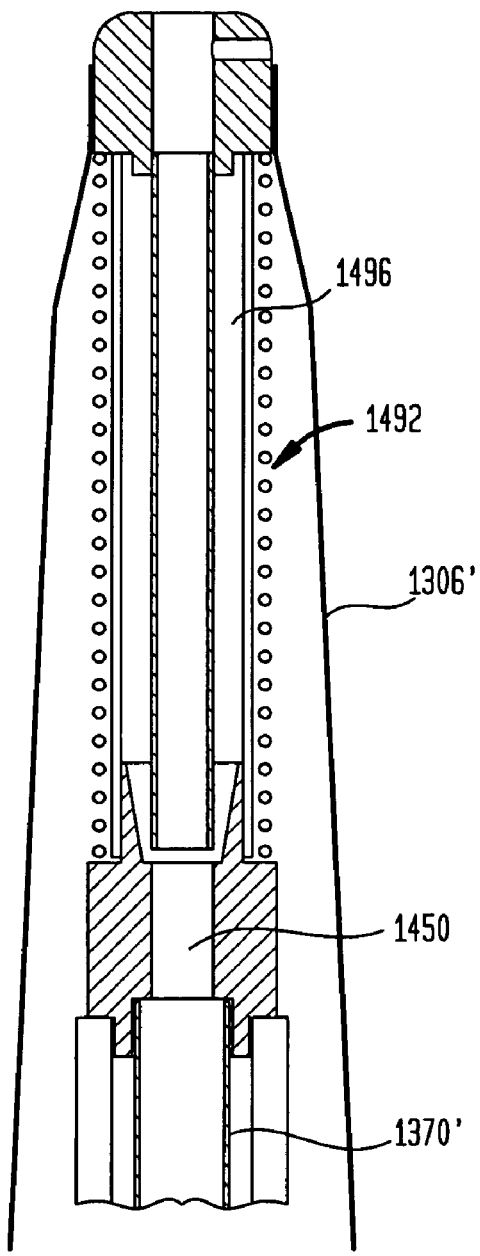
FIGS. 25 and 26 are views similar to FIGS. 22 and 23, but depicting apparatus according to yet another embodiment of the invention.
Figure 26:
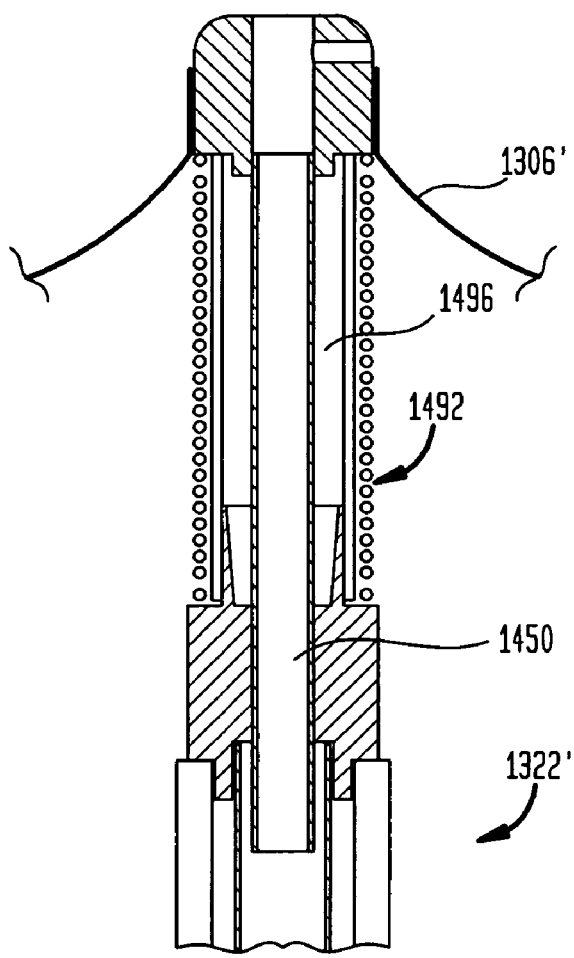

Numerous variations and combinations of the features discussed above can be employed. For example, in the variant depicted in FIGS. 25 and 26, the extensible structure 1492 includes a reinforcing tube 1496 which can be telescopically received inside the emitter assembly 1322' when the expansible structure is in its expanded condition, as when the structural balloon 1306' is in its inflated condition (FIG. 26). In the particular structure illustrated, the reinforcing tube 1496 fits through the bore 1450 of the distal mounting structure of the emitter assembly and is telescopically received within the inside tube 1370. When the expansible structure is collapsed, and hence balloon 1306' is deflated, the reinforcing tube 1496 is partially or fully withdrawn from the inside tube 1370', from bore 1450, or both. Here again, the structure provides reinforcement against kinking, but allows flexibility in the deflated, extended condition and also cooperates with the emitter assembly, so as to form a passageway extending through the expandable balloon structure.

Other extensible structures are disclosed in co-pending PCT International Application No. PCT/US03/28578 and the corresponding co-pending U.S. patent application Ser. No. 10/635,170, published as US/2004/0054362-A1, the disclosure of which is incorporated by reference herein, as well as in the '257 application.

The preferred extensible structures in these applications include engagement elements which reinforce the expansible structure and form a rigid structure when the expansible structure is in its expanded condition. In one arrangement, the engagement elements include a tubular distal engagement element which extends proximally from the distal end of the expansible structure or balloon. A coil spring is disposed inside of this tubular engagement element. A proximal engagement element includes a main portion, a stem having a diameter smaller than the diameter of the main portion and a bulbous tip at the proximal end of the stem. The bulbous tip is engaged inside the distal engagement element at all times. When the expansible structure is in its collapsed condition and the extensible structure is in its extended condition, only the bulbous tip remains engaged inside the distal engagement element. In this disengaged condition, the distal engagement element can pivot around the bulbous portion of the stem so that the structure can flex. When the expansible structure is expanded, the distal element is forced proximally, so that the main portion of the proximal element enters into the distal element and the distal element is forced to a coaxial alignment with the proximal element. In this engaged condition, the elements form a rigid reinforcing structure. An extensible tube may extend from the proximal element through the interior of the coil spring, so as to provide a continuous passageway for the purposes discussed above herein. In a variant of this structure according to a feature of the present invention, the engagement elements may be provided with interlocking features such as an inwardly-projecting flange on the distal engagement element having a diameter slightly smaller than the diameter of the bulbous tip. Such a flange prevents the distal engagement element from moving distally beyond the bulbous tip on the proximal engagement element, and thus serves the same function as the interlocking flanges 1397 and 1401 discussed above with reference to FIG. 22A.

The structures which provide for circulation of the cooling liquid may be varied. Merely by way of example, the port 1346 (FIGS. 15 and 16) of the proximal mounting structure may be replaced by one or more slots similar to the slots 1354 (FIG. 17) in the distal mounting structure. Conversely, the slots of the distal mounting structure may be replaced by a port, as used in the proximal mounting structure discussed above. Also, it is not essential that the second peripheral lumen of the catheter communicate with the interior of the structural balloon through a feature of the proximal mounting structure. For example, where the distal end of the catheter projects into the interior of the structural balloon, the catheter itself may be provided with a port or slots to provide communication with the second lumen. In a further variant, one or both of the mounting structures may be omitted. For example, the proximal mounting structure may be omitted if the distal end of the catheter itself incorporates a port. In such an arrangement, one of the additional lumens of the catheter may communicate directly with the interior of the tubular piezoelectric element, whereas another additional lumen of the catheter may communicate directly with the interior of the structural balloon. Also, although it is highly advantageous to have a continuous passageway extending through the ablation device in its expanded condition, the same can be omitted as, for example where it is acceptable to use a separate catheter for injection of the contrast medium. Also, although the reinforcing structure 1321 discussed above provides important advantageous in stiffening the expansible structure and assuring the ablation region lies in a predictable location, the same can be omitted with corresponding loss of function.

In the embodiment discussed above with reference to FIGS. 14-23, the interface between the inside tube 1370 and the liquid in the annular passageway 1376 has some reflectivity for ultrasound, so that at least some of the ultrasonic waves directed radially inwardly from the inside surface of the tubular piezoelectric element will be reflected at this interface and directed radially outwardly to reinforce the useful ultrasonic waves emitted at the outside surface of the piezoelectric element. As disclosed in the aforementioned '512 publication, and as further described in U.S. Patent Publication US 2003/0013968 A1, the disclosure of which is hereby incorporated by reference herein, a highly reflective interface may be provided by forming a tube as a dual-walled structure with an gas-filled space between the walls.

Further, certain features of the embodiments discussed above, as, for example, the use of a normal and canted disposition, can be applied with ablation devices which use forms of energy other than ultrasonic as, for example, ablation devices which apply light, radio frequency or other forms of energy.

Figure 27:
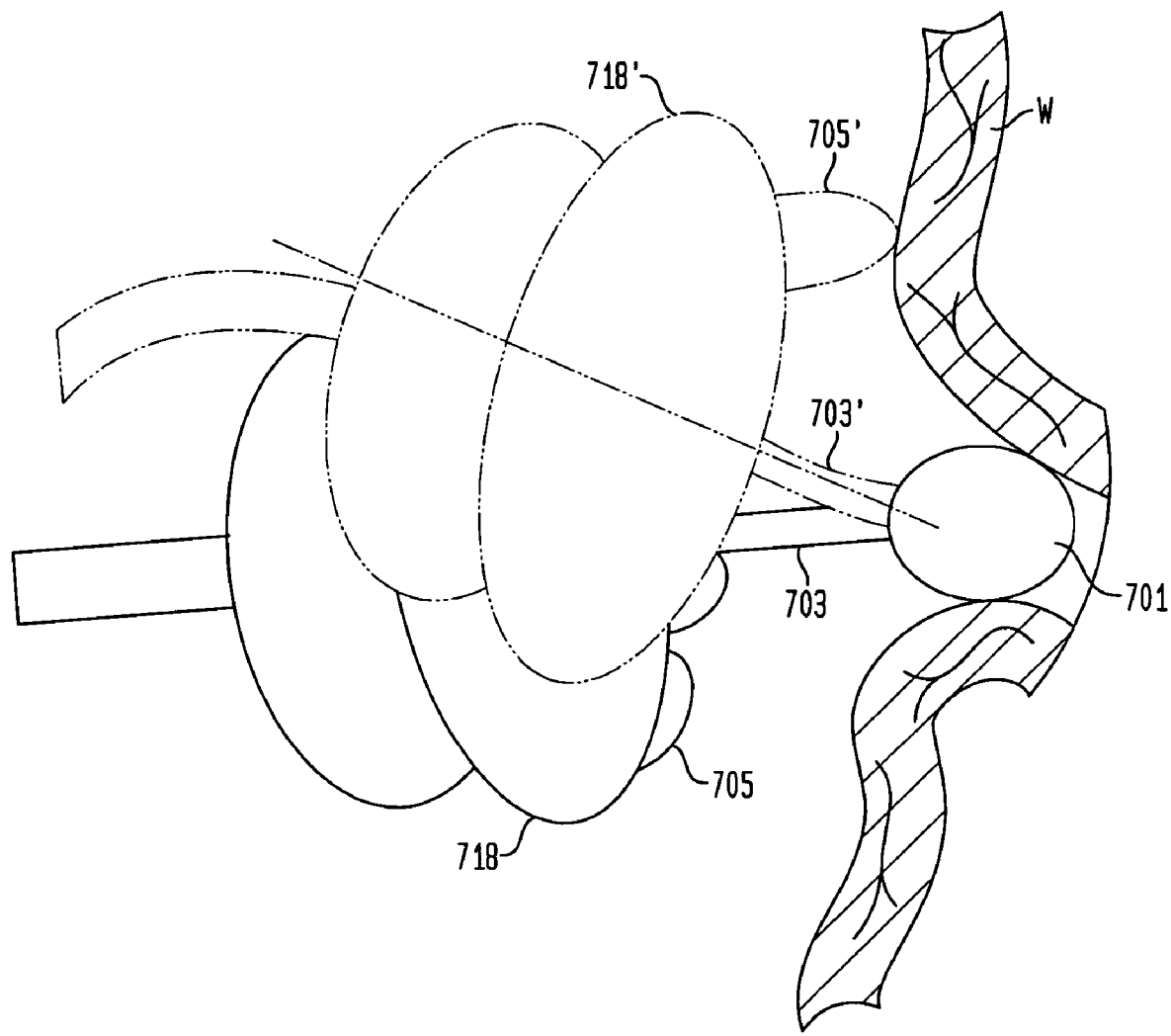
FIG. 27 is a schematic elevational view depicting apparatus according to yet another embodiment of the invention.

In apparatus according to a further embodiment of the invention, (FIG. 27), the insertable structure may incorporate a guide element 701 adapted to engage a portion of the anatomy as, for example, the ostium of the pulmonary vein, distal to or forward of the ablation device 718. The guide element may be linked to the ablation device by a bendable or deformable element 703 which can be deformed in any of the ways discussed above with reference to deforming the catheter, so that the disposition of the ablation device relative to the heart wall W may be controlled as, for example, by bending the link 703 to the position indicated in broken lines at position 703', so as to move the ablation device to the position indicated in broken lines at 718'. The guide element 701 or the link 703 may be provided with a port for emitting a contrast medium in the manner discussed above.

In yet another variant, one or more independently inflatable structures 705 may be provided on the distal or forward surface of the ablation unit itself, so that the ablation element may be tilted relative to the heart wall and positioned relative to the heart by inflating one or more of the inflatable structures, as indicated at 705'. These additional inflatable structures can be positioned in a region of the distal wall which will bear on the wall of the heart or other anatomical structure, but which does not serve to transmit appreciable amounts of the ultrasonic waves from the reflective interface to the heart wall. Alternatively, the additional reflective structures 705 may be liquid-inflatable balloons which are adapted to transmit the ultrasonic waves so that the ultrasonic waves can be transmitted through these structures.

As discussed above, the ablation device can be positioned selectively within the heart and brought to the desired disposition relative to the heart wall regardless of the configuration of the ostium and pulmonary vein. This enhances the ability of the device to form a loop-like ablated region within the heart wall surrounding the pulmonary vein.

Additionally, an ablation device which focuses the ultrasonic waves into a relatively large loop-like region having a loop diameter $D_A$ (FIG. 1) of about 25 mm or more, and preferably about 25-30 mm, also tends to provide better results than a device forming a smaller-diameter ablation region as, for example, about 20 mm. While the smaller loop diameters as, for example, 20 mm or so, provide a loop diameter sufficient to encompass the ostium in some subjects, the use of loop diameters within the preferred range increases the probability that the loop diameter will be sufficient to encompass the ostium, even where the subject has a widely flared or noncircular ostium or other a typical shape. Significantly larger loop diameters require significantly larger balloon diameters, which make the task of threading the device into the heart and removing it from the heart more difficult.

Figure 39:
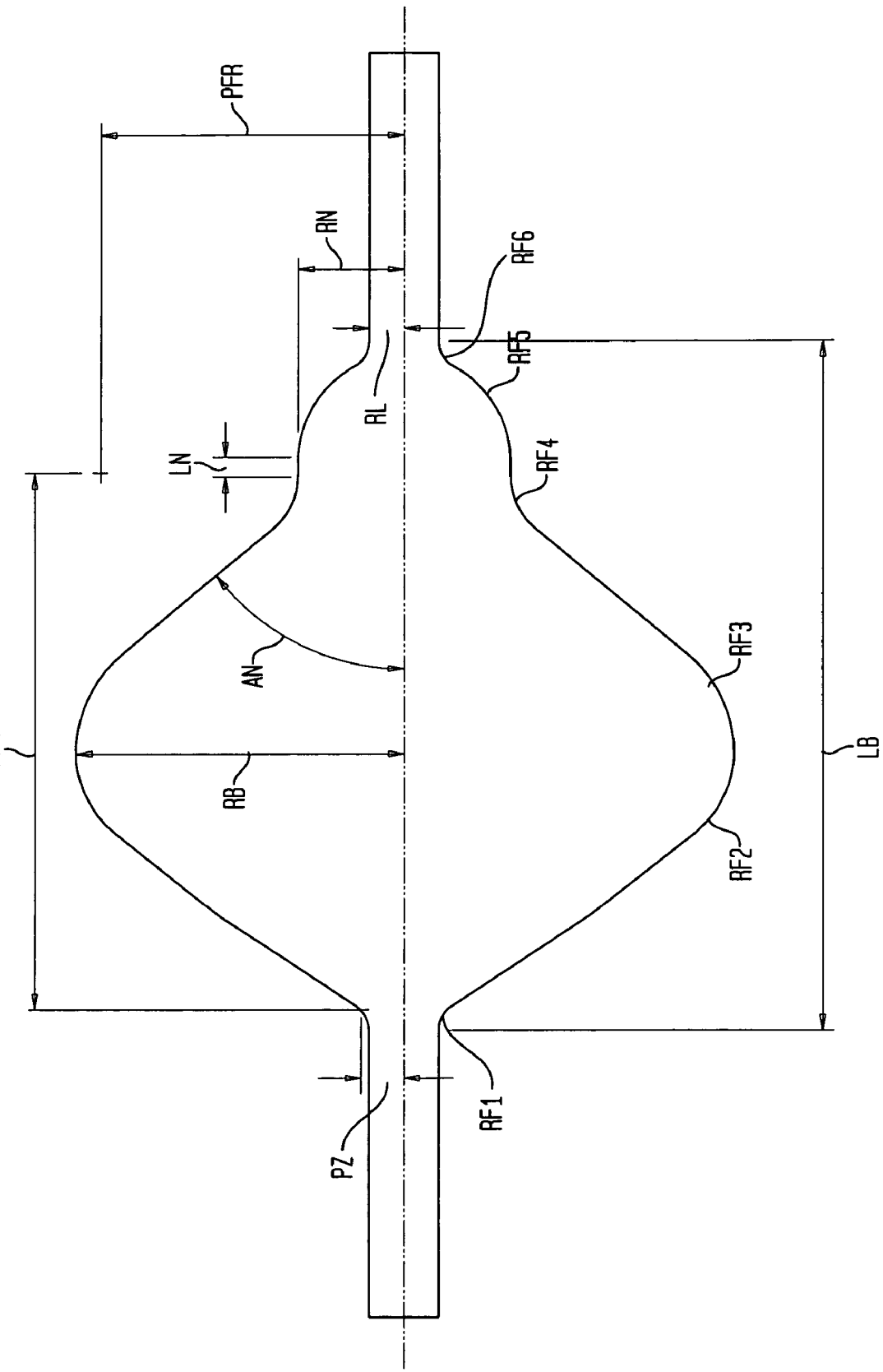
FIG. 39 is a diagrammatic sectional view depicting exemplary balloon dimensions

A loop diameter of about 30 mm can be provided using an ablation unit with a structural balloon of about 32 mm maximum diameter in the inflated condition. One example of a suitable structural balloon is depicted in FIG. 39 with exemplary dimensions as shown in Table I, below. This balloon has a "nipple" or projection 731 on its distal side, which can be engaged with the ostium of the pulmonary vein during positioning. Such a nipple can be used in conjunction with the other positioning systems discussed herein. However, where a steering system is provided for controlling the disposition of the ablation device, it is desirable to omit the nipple and to make the balloons and associated structures as short as practicable in the proximal-to-distal or forward-to-rearward dimension. For example, one suitable structural balloon which provides a 25 mm loop diameter has a maximum diameter of 28 mm in the inflated condition, and has a length of only 26 mm. This balloon does not have a nipple.

TABLE I

| Dimension Name | Dimension Indicator (FIG. 39) | Value |
|---|---|---|
| Balloon length | (LB) | 35.0000 mm |
| Balloon radius | (RB) | 16.0000 mm |
| Lumen radius | (RL) | 1.6890 mm |

TABLE I-continued

| Dimension Name | Dimension Indicator (FIG. 39) | Value |
| --- | --- | --- |
| Parabola focus height | (PFH) | 27.0000 mm |
| Parabola focus radius | (PFR) | 15.0000 mm |
| Parabola zero | (PZ) | 2.4600 mm |
| Transducer height | (HT) | 9.0000 mm |
| Nipple section length | (LN) | 1.3700 mm |
| Nipple radius | (RN) | 5.0000 mm |
| Nipple angle | (AN) | 52.3200 degree |
| Fillet #1 radius | (RF1) | 1.6700 mm |
| Fillet #2 radius | (RF2) | 5.7900 mm |
| Fillet #3 radius | (RF3) | 5.7900 mm |
| Fillet #4 radius | (RF4) | 3.0000 mm |
| Fillet #5 radius | (RF5) | 5.0000 mm |
| Fillet #6 radius | (RF6) | 2.0000 mm |

Figure 28:
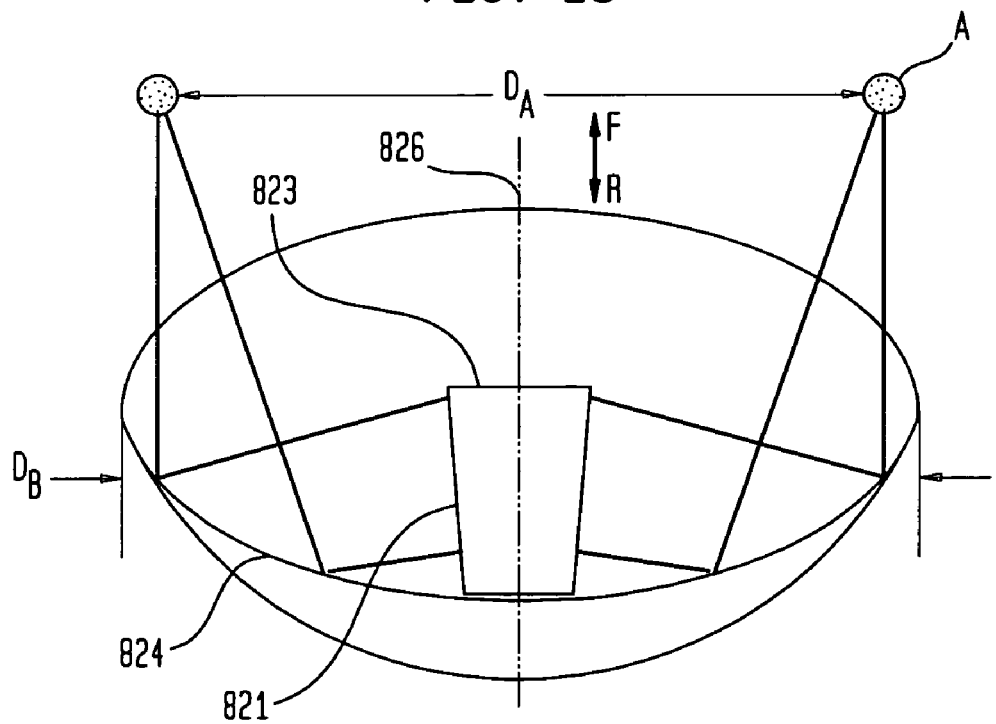
FIG. 28 is a schematic view depicting a portion of apparatus according to yet another embodiment of the invention.

As seen in FIG. 28, the loop diameter $D_A$ can be increased by directing the ultrasonic waves from emitter 823 rearwardly, as well as radially outwardly away from axis 826. Such rearward direction may be provided by an emitting element 823 in a conical or other shape having a circumferential wall 821 which slopes outwardly, away from the central axis 826 in the forward direction. The rearwardly directed ultrasonic waves impinge on the active reflective surface 824 and are reflected outwardly, away from the axis to a greater degree than would be the case for purely radially-directed ultrasonic waves. Thus, the ratio of the loop diameter $D_A$ of the ablation region A to the diameter $D_B$ of balloon or other structure providing the reflective interface can be increased.

In a further variant, the rearwardly and outwardly directed ultrasonic waves can be provided by a cylindrical emitter configured as a series of cylindrical bands spaced along the axis and operated as a phased array.

Figure 29:
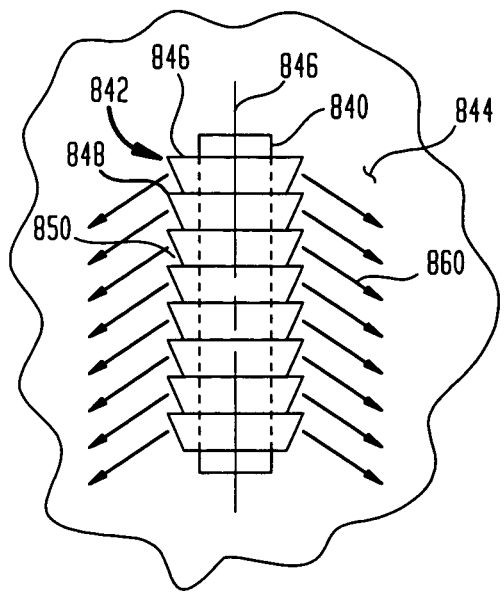
FIG. 29 is an elevational view depicting apparatus according to a still further embodiment of the invention.
Figure 30:
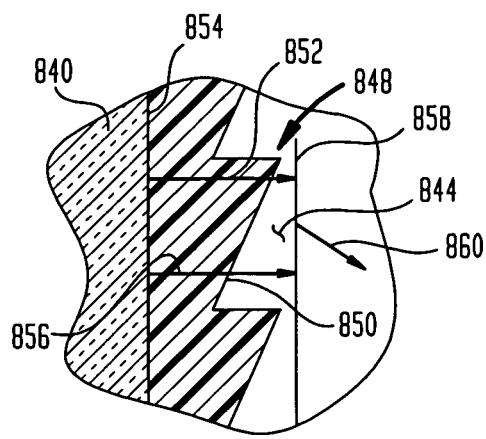
FIG. 30 is a fragmentary view on an enlarged scale of a portion of the apparatus shown in FIG. 29.

In a further variant depicted in FIG. 29, a cylindrical transducer 840 having a central axis 846 may be equipped with an annular Fresnel lens 842 coaxial with the transducer. The lens is formed from a material such as a solid polymer, metal, ceramic or the like in which the speed of sound is greater than the speed of sound in the liquid 844 used to fill the balloon surrounding the transducer. The Fresnel lens includes a series of annular rings 846 each having a relatively thick portion 848 at its distal edge and a relatively thin portion 850 at its proximal edge. As shown in detail in the sectional view of FIG. 30, an ultrasonic wave 852 traveling from the surface 854 of transducer 840 through the thick portion 848 of a ring traverses a relatively long distance through the material of the lens and a relatively short distance through the liquid 844 to reach a location 858 beyond the lens, at a given radial distance from the central axis of the transducer. Conversely, a wave 856 traveling through a thin portion of the ring travels through a relatively short distance in the material of the lens and through a relatively long distance in liquid 844 to reach the same radial location 858. The two waves start from surface 854 in phase with one another. When they reach radial location 858, wave 852 is advanced in phase relative to wave 856 so that the two waves merge to form a combined wave 860 directed rearwardly. The rearwardly directed waves 860 can be reflected as described above.

Figure 31:
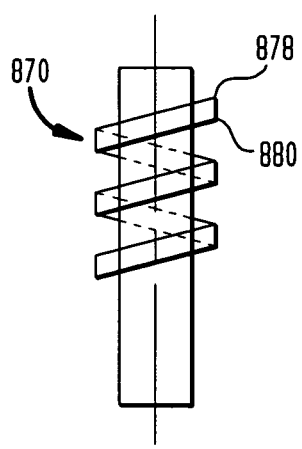
FIG. 31 is a view similar to FIG. 29, but depicting apparatus according to a further embodiment of the invention.

The Fresnel lens can be varied in numerous ways. For example, it is not essential to have the Fresnel lens in contact with the surface of the transducer. Also, the rings constituting the lens need not contact one another and indeed can be spaced apart from one another so that regions between the spaced rings constitute portions of the lens with zero thickness. Also, the rings can be replaced by successive terms of a helix 870 (FIG. 31) coaxial with the transducer. At each location around the circumference of the cylindrical transducer, adjacent turns of the helix act in the same way as adjacent rings. The helix desirably has non-uniform thickness in the axial direction, so that each turn of the helix has a relatively thick portion 878 at the distal edge of the turn and a relatively thin portion 880 towards the proximal edge of the turn. In a further variant (not shown) a helix having spaced apart turns or a lens formed from spaced apart rings may have rings or turns of uniform thickness, so that the lens is formed solely by portions having zero thickness (portions between rings or turns) and portions of a given, uniform thickness. Such a lens will diffract a portion of the ultrasound in the rearward direction and a portion of equal strength in the forward direction. The diffraction or ultrasound-directing properties of an annular Fresnel lens defined by spaced-apart rings or by the turns of a helix can be varied by changing the spacing between the turns or rings as, for example, by compressing or stretching the helix 870. Annular Fresnel lenses as discussed above can be used in connection with reflective or other focusing elements as in the combinations above or can be used independently as, for example, to project a collimated, generally conical beam of ultrasound around the axis the transducer.

Figure 33:
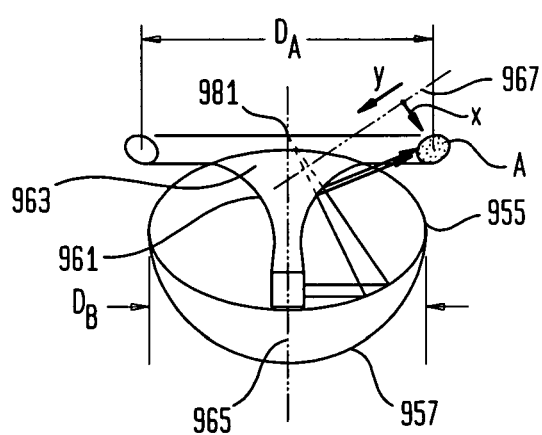
FIG. 33 is a view similar to FIG. 32, but depicting apparatus according to yet another embodiment of the invention.

In a further embodiment, shown in FIG. 33, the transducer 951 is disposed within a structural balloon 955, which again is filled with a liquid and directs ultrasonic waves outwardly to a first reflective interface formed by a wall separating the interior of the structural balloon from the interior of a reflective balloon 957, which is filled with a gas. The shape of the reflective interface 953 is selected so that the reflected ultrasound is directed forwardly or distally and radially inwardly to a second reflective interface 961 defined by the liquid filled structural balloon 955 and a gas-filled auxiliary reflector balloon 963. The ultrasound is reflected forwardly and radially outwardly at interface 961. Most preferably, the second reflective interface 961 is configured as a hyperboloid of revolution about the central axis 965 of the device. That is, surface defining second reflecting interface 961 has a generatrix defined by the equation $(X^2/A^2)-(Y^2/B^2)=1$ where A and B are constant; X is distance from an axis 967 and Y is axial distance from an origin point along an axis 967 disposed at an oblique angle to the central axis of the balloon structure. The generatrix is the curve which, when rotated around the central axis 965 of the emitter, forms the surface. The hyperboloid further focuses the ultrasonic waves as well as reflecting them outwardly into an ablation region A. For example, where the first reflective interface 953 is arranged to focus the ultrasonic waves at a point 981 on the central axis 965, the second reflective interface 961 refocuses the energy to an annular focal region in the ring-like ablation zone A. The use of an auxiliary reflective balloon tends to "throw" via ultrasound outwardly and thus aids in forming an ablation region A, having a larger diameter $D_A$ using a reflective structure having the relatively small balloon diameter $D_B$.

Figure 32:
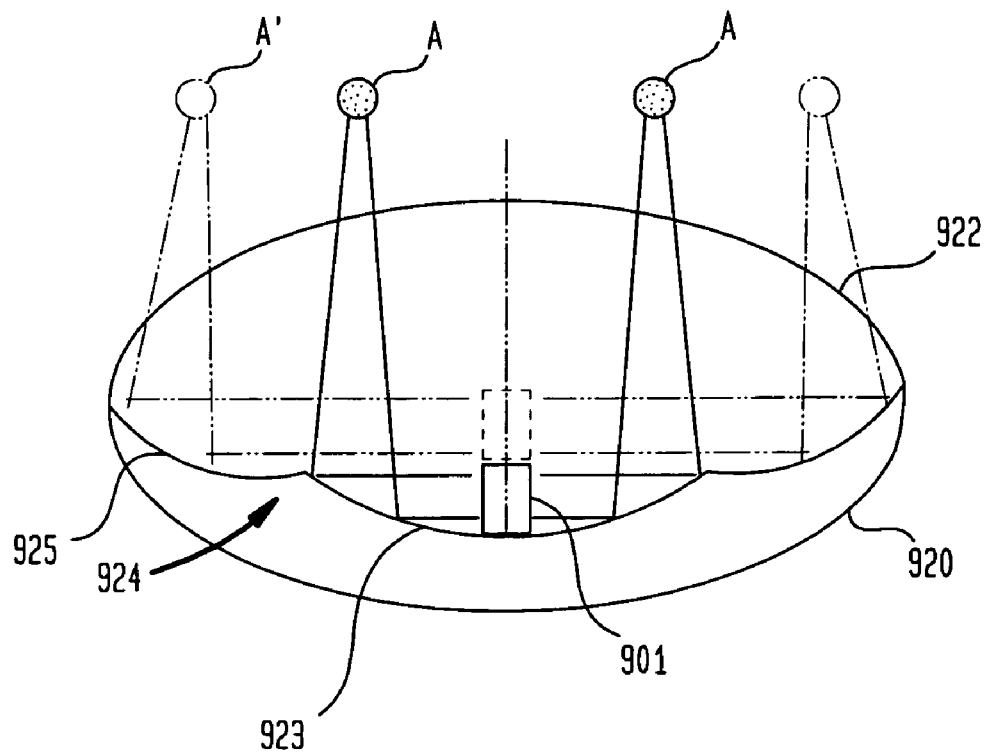
FIG. 32 is a schematic diagram depicting apparatus according to yet another embodiment of the invention.

As seen in FIG. 32, a reflective surface 924 such as that defined by a common wall between balloons 922 and 920 may be provided as a series of multiple reflective regions 923 and 925 distributed in the axial or forward-to-rearward direction. The emitter 901 may be moved forwardly and rearwardly so as to selectively direct the ultrasonic waves onto one or another of these regions and thereby direct the ultrasonic waves into a first loop-like region A, shown in solid lines, or onto a second region A' of larger diameter, shown in broken lines. Alternatively, an elongated emitter may be provided in two independently actuatable zones so that when one zone is actuated, the energy is directed onto region 923; whereas when another zone is actuated, the energy is directed onto region 925 of the reflective surface. This arrangement provides for selection of loop diameters during use.

Figure 34:
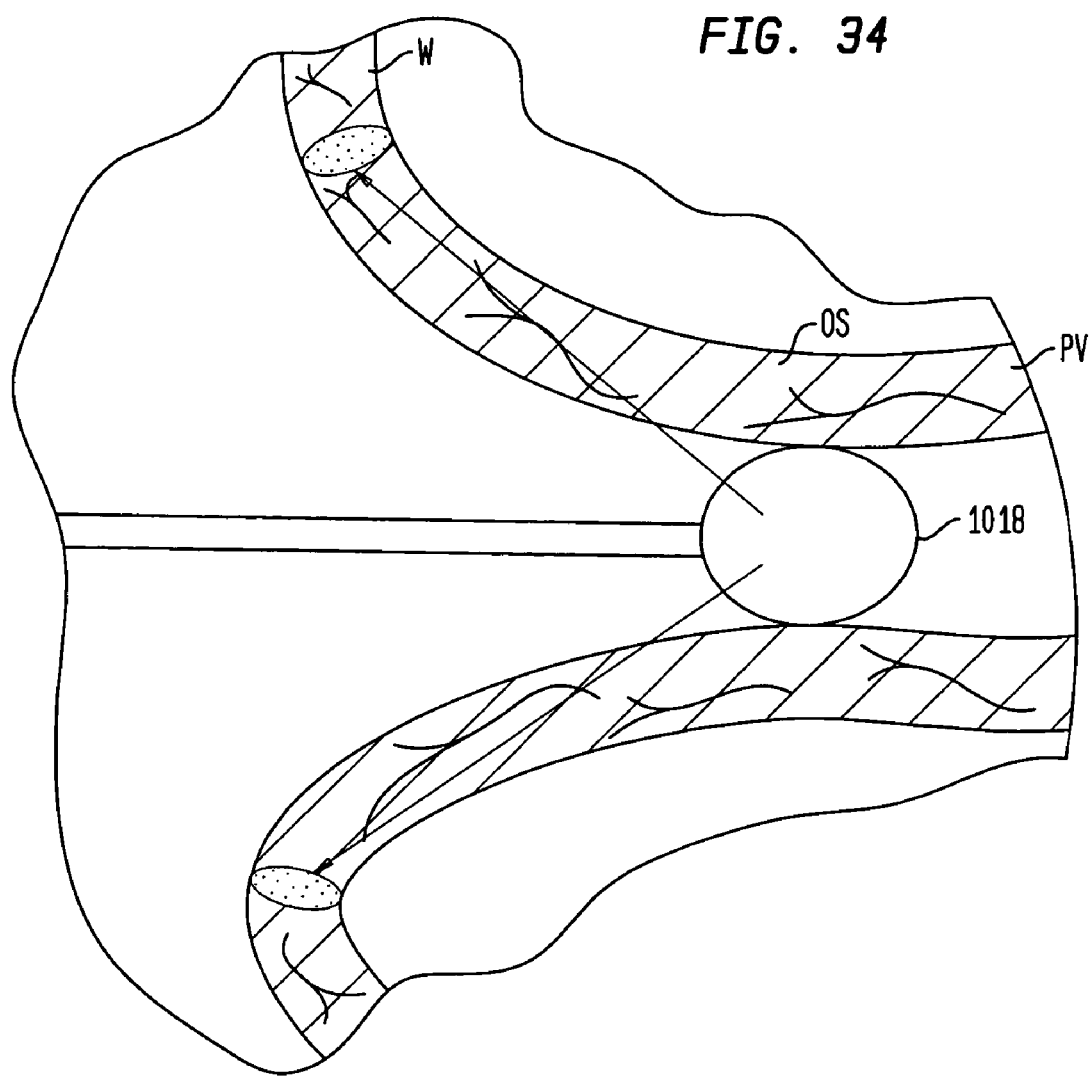
FIG. 34 is a fragmentary schematic view depicting apparatus according to a still further embodiment of the invention.

In the arrangements discussed above, the ultrasonic waves are directed generally forwardly in a direction from the interior of the heart toward the pulmonary vein or other blood vessel to be circumscribed by the ablation region. In the variant shown in FIG. 34, the ablation device 1018 is configured to direct ultrasonic waves rearwardly, in the direction from the blood vessel toward the heart and onto a ring-like region of the heart wall W encircling the pulmonary vein PV or ostium OS.

For example, the ablation structures discussed herein can be adapted to direct to the ultrasonic waves rearwardly by reversing the distal and proximal ends of such structures.

An ablation element (FIG. 35) in accordance with a further embodiment of the invention includes transducer 1102 and a balloon structure defining a first reflective interface 1104 and a second reflective interface 1106 spaced apart from the first reflective interface. The first and second reflective interfaces are both in the form of surfaces of revolution about the central axis of 1108. As in the embodiments discussed above, the first reflective interface 1104 may be formed by an interface between a structural balloon 1110 and a first reflective balloon 1112, the structural balloon being filled with a liquid such as an aqueous liquid and the first reflective balloon being filled with a gas. The second reflective interface 1106 may be formed by an interface between the structural balloon 1110 and a second reflector balloon 1114, also filled with a gas. The two reflective interfaces converge with one another, but do not meet, so that there is a small portion of the wall of the structural balloon forms an exit window 1114, extending around the central axis 1108. The second reflective interface 1106 may be in the form of a surface of revolution of an exponential curve such that the radial distance $R_{1108}$ from the central axis 1108 any point on the curve is equal to $e^z+C$ where z is the axial distance from an origin point to the point on the surface 1106 and C is a constant. The first reflective interface 1104 slopes forwardly and radially outwardly; it may be in the form of a cone or other surface of revolution about central axis 1108. The converging reflective interfaces define an annular channel 1151 having an entry 1153 surrounding transducer 1102 and an annular exit at window 1114. The reflective interfaces 1104 and 1102 converge with one another toward the exit of the channel, and concentrate sound waves emanating from transducer 1102 into a small area as the sound waves pass from the transducer to exit window 1114. Thus, sound waves passing outwardly from the transducer or repeatedly reflected between the two interfaces so that they ultimately reach the exit window. The converging interfaces, thus concentrate the ultrasonic waves into a small band of ultrasonic waves exiting through the exiting window 1114 into the ablation region. Convergent surfaces other than exponential and conical surfaces can be used.

Figure 35:
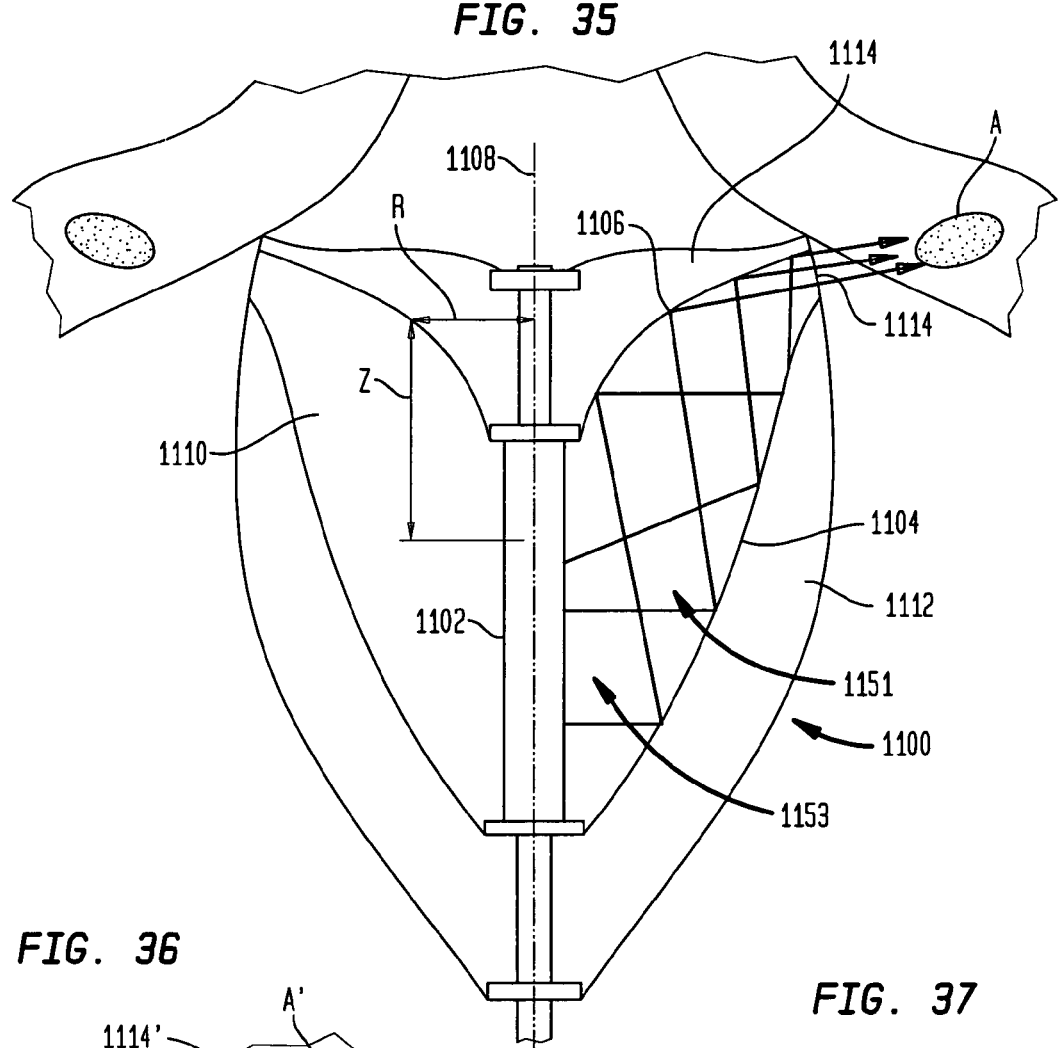
FIG. 35 is a diagrammatic sectional view depicting apparatus to yet another embodiment of the invention.
Figure 36:
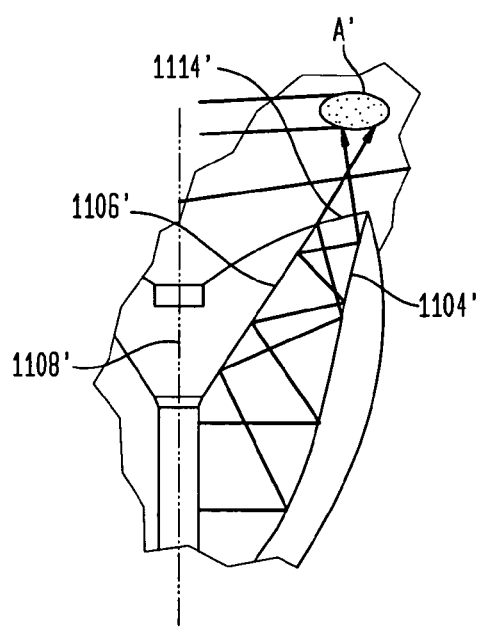
FIG. 36 is a fragmentary, diagrammatic sectional view depicting apparatus according to yet another embodiment of the invention.

Depending upon the exact configuration of the converging surfaces will direct the ultrasonic waves exiting through the window outwardly and forwardly. The device shown in FIG. 35 directs the ultrasonic waves nearly radially, outwardly. However, as shown in FIG. 36, where the exit window 1114' forms a portion of the distal wall of the ablation device and where the converging reflective services 1106' and 1104' are oriented closer to parallel with a forward to rearward axis 1108' of the device, the ultrasonic waves will be directed substantially forwardly so as to ablate region A' almost directly in front of the device. In a variant of the structures shown in FIGS. 22 and 23, the structural balloon 1110 of FIG. 35 is omitted and the exit window at 1114 is simply left open to the surroundings. The space within the channel surrounding the transducer is filled with blood or other bodily fluids or by an anatomically-compatible fluid introduced into the area surrounding the transducer as, for example, saline solution.

Figure 37:
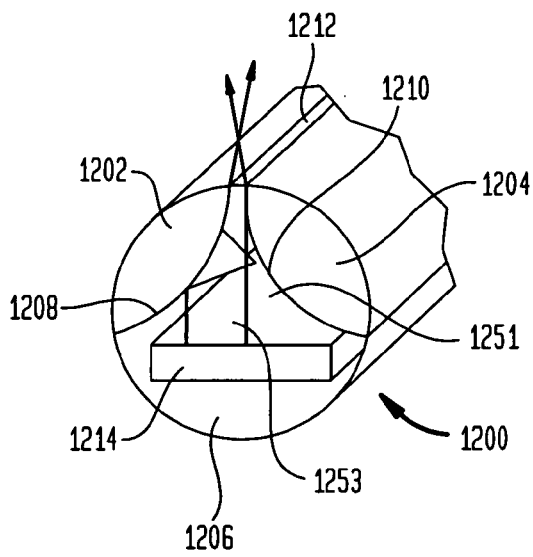
FIG. 37 is a diagrammatic, partially sectional, partially perspective view depicting apparatus according to a still further embodiment of the invention.

The concept of a sonic or ultrasonic concentrator defined at least in part by gas-filled structures forming reflective interfaces is not limited to ablation of ring-like region. For example, as seen as FIG. 37 an elongated catheter 1200 has gas-filled regions 1202 and 1204 and a liquid-filled region 1206 extending lengthwise along the catheter. Gas-filled region 1202 defines a first reflective interface 1208 with the liquid-filled region whereas gas-filled region 1204 defines a second reflective interface 1210 with the liquid-filled region. These reflective interfaces converge with one another but do not meet one another, so that a portion of the liquid-filled region disposed between the converging interfaces extends to the exterior of the catheter and defines an exit window 1212. Thus, the reflective interfaces define a channel 1251 having a wide entry 1253 and a narrow exit at window 1212. The exit window is generally in the form of a strip or slit extending lengthwise along the catheter. A planar, slab like transducer 1214 also extends lengthwise along the catheter. As seen in FIG. 37, ultrasonic waves directed from the face of the planar transducer impinge on the reflective interfaces 1208 and 1210 and is repeatedly reflected by the interfaces so that the ultrasonic energy is concentrated into the slit-like exit window. Such a structure can be used, for example, to ablate a strip-like region of tissue.

Figure 38:
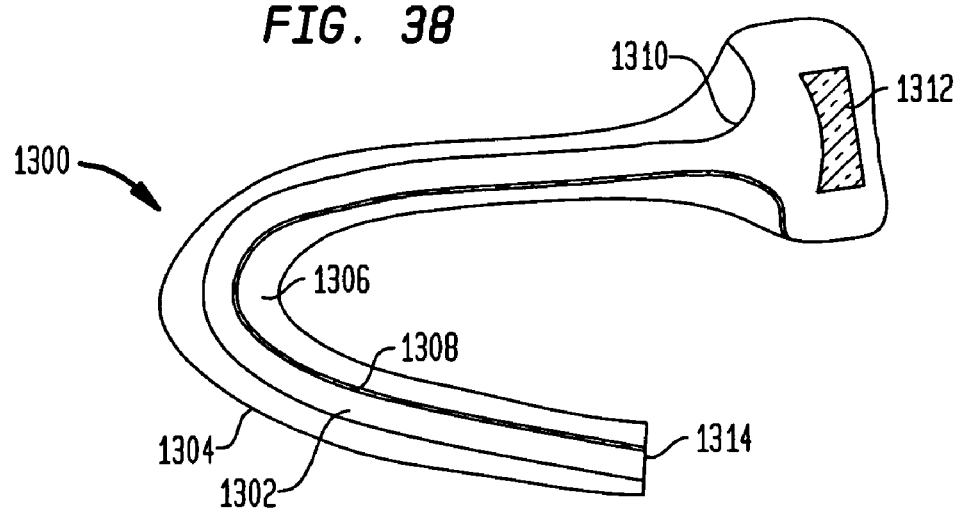
FIG. 38 is a diagrammatic sectional view depicting apparatus according to yet another embodiment of the invention.

In yet another embodiment, an elongated catheter 1300 (FIG. 38) includes a central lumen 1302 filled with a liquid. The catheter includes an outer sheath 1304 surrounding the central lumen and defining an annular space 1306 between the wall 1308 of the central lumen and the exterior of the catheter. The space 1306 is filled with a gas so as to define a single tubular reflective interface at the wall 1308 of the central lumen, forming a tubular channel. Such a catheter serves as a flexible wave guide for ultrasonic waves. The reflective interface 1308 may also define a convergent horn-like structure 1310 at the proximal or entry end of the wave guide. Ultrasonic waves from a transducer 1312 is concentrated by the convergent horn and travels through the wave guide to an exit opening 1314 at the distal end of the structure.

As discussed above, in ablation of the heart wall for treatment of atrial fibrillation, the ablation region desirably extends through the heart wall, rather than through the wall of the pulmonary vein. However, the ablation region may extend in the ostium or even through a proximal region of the pulmonary vein. However, it is preferred to keep the ablation region out of the pulmonary vein and at as large a diameter as possible, so as to minimize scarring and stenosis of the pulmonary vein. Imaging modalities other than fluoroscopy can be used, such as conventional x-ray imaging, CT or MR imaging. Also, contrast media other than x-ray contrast media can be employed. Ultrasonic ablation devices other than the specific balloon structures discussed above can be used. Also, the techniques can be used with non-ultrasonic ablation devices.

As discussed in the aforementioned co-pending applications, the techniques used for pulmonary vein ablation also can be applied to ablation of other anatomical structures for other therapeutic purposes.

As these and other variations and combinations of the features discussed above can be utilized without departing from the present invention as defined by the claims, the foregoing description of the preferred embodiment should be taken by way of illustration rather than by way of limitation of the invention.

The invention claimed is:

1. A method of applying ultrasonic energy to cardiac tissue comprising:
providing a catheter having an ultrasonic transducer and a structural balloon, the structural balloon sandwiched between first and second reflective balloons to form a first reflective interface at an interface between the structural balloon and the first reflective balloon and a second reflective interface at an interface between the structural balloon and the second reflective balloon, the second reflective interface spaced apart from and directed towards the first reflective interface so as to form a window therebetween;
inserting the catheter in a heart of a mammalian subject and inflating the structural balloon and the first and second reflective balloons so that the window is aligned with a preselected region of cardiac tissue; and
actuating the ultrasonic transducer to emit ultrasonic energy, the first and second reflective interfaces directing the ultrasonic energy through the window and into the preselected region of the cardiac tissue.

2. A method as claimed in claim 1 further comprising injecting a contrast medium, wherein the contrast medium is an x-ray contrast medium.

3. A method as claimed in claim 1 further comprising injecting a contrast medium, wherein the contrast medium is injected into an atrium of the heart.

4. A method as claimed in claim 3 wherein the step of injecting contrast medium includes injecting the medium so that the medium advances forwardly.

5. A method as claimed in claim 4 further comprising the step of maintaining the catheter at least partially abutting a cardiac wall during the step of injecting the contrast medium.

6. A method as claimed in claim 5 wherein the step of injecting a contrast medium includes obtaining one or more images while the catheter abuts the cardiac wall.

7. A method as claimed in claim 5 further comprising the step of retracting the catheter away from the cardiac wall after injecting the contrast medium.

8. A method as claimed in claim 7 wherein the step of injecting a contrast medium includes obtaining one or more images after retracting the catheter.

9. A method as claimed in claim 1 further comprising injecting a contrast medium outside of the structural balloon.

10. A method as claimed in claim 9 wherein the catheter has a central axis, and the step of injecting a contrast medium includes introducing the contrast medium through a port in a wall of the structural balloon adjacent the central axis.

11. A method as claimed in claim 9 wherein the catheter has a central axis, and the step of injecting a contrast medium includes introducing the contrast medium through an outlet port of a tubular stylet communicating with the atrium adjacent the central axis.

12. A method as claimed in claim 1 further comprising injecting a contrast medium on a distal side of the catheter.

13. A method as claimed in claim 1 wherein providing a catheter comprises providing the catheter in which the first and second reflective interfaces converge towards one another.

* * * * *